(12) United States Patent
Rinsch et al.

(10) Patent No.: US 9,980,980 B2
(45) Date of Patent: *May 29, 2018

(54) COMPOUNDS, COMPOSITIONS AND METHODS FOR PROTECTING BRAIN HEALTH IN NEURODEGENERATIVE DISORDERS

(71) Applicant: Amazentis SA, Ecublens (CH)

(72) Inventors: Christopher L. Rinsch, Morges (CH); Philippe V. Dupraz, Crissier (CH)

(73) Assignee: Amazentis SA (CH)

(*) Notice: Subject to any disclaimer, the term of this patent is extended or adjusted under 35 U.S.C. 154(b) by 36 days.

This patent is subject to a terminal disclaimer.

(21) Appl. No.: 14/584,581

(22) Filed: Dec. 29, 2014

(65) Prior Publication Data

US 2015/0196577 A1    Jul. 16, 2015

Related U.S. Application Data

(63) Continuation of application No. 12/842,750, filed on Jul. 23, 2010, now Pat. No. 8,933,217.

(60) Provisional application No. 61/228,374, filed on Jul. 24, 2009.

(51) Int. Cl.
| | |
|---|---|
| A61K 31/7048 | (2006.01) |
| A61K 31/7024 | (2006.01) |
| C07H 13/08 | (2006.01) |
| C07H 15/18 | (2006.01) |
| C07H 15/26 | (2006.01) |
| A61K 31/352 | (2006.01) |
| A61K 31/357 | (2006.01) |
| A61K 31/57 | (2006.01) |
| A61K 36/185 | (2006.01) |
| C07D 493/04 | (2006.01) |
| C07D 493/22 | (2006.01) |
| A23K 20/111 | (2016.01) |
| A23L 33/10 | (2016.01) |
| A23L 33/105 | (2016.01) |

(52) U.S. Cl.
CPC ........ *A61K 31/7048* (2013.01); *A23K 20/111* (2016.05); *A23L 33/10* (2016.08); *A23L 33/105* (2016.08); *A61K 31/352* (2013.01); *A61K 31/357* (2013.01); *A61K 31/57* (2013.01); *A61K 31/7024* (2013.01); *A61K 36/185* (2013.01); *C07D 493/04* (2013.01); *C07D 493/22* (2013.01); *C07H 13/08* (2013.01); *C07H 15/18* (2013.01); *C07H 15/26* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,236,940 A | 8/1993 | Audiau et al. |
| 6,423,365 B1 | 7/2002 | Nair |
| 6,576,271 B2 | 6/2003 | Nair et al. |
| 6,656,914 B2 | 12/2003 | Nair et al. |
| 6,676,978 B1 | 1/2004 | Nair |
| 6,958,164 B2 | 10/2005 | Dutta-Roy |
| 2006/0211635 A1 | 9/2006 | Seeram et al. |
| 2006/0269629 A1 | 11/2006 | Bates et al. |
| 2008/0214656 A1 | 9/2008 | Lim et al. |
| 2008/0318877 A1 | 12/2008 | Seeram et al. |
| 2009/0053340 A1 | 2/2009 | Crosbie et al. |
| 2009/0123584 A1 | 5/2009 | O'Kennedy et al. |

FOREIGN PATENT DOCUMENTS

| | | |
|---|---|---|
| CA | 2653305 A1 | 11/2006 |
| JP | 2009-102288 A | 5/2009 |
| WO | WO-2005/072760 A1 | 8/2005 |
| WO | WO-2005/089066 A2 | 9/2005 |
| WO | WO-2005/097106 A1 | 10/2005 |
| WO | WO-2006/022502 A1 | 3/2006 |
| WO | WO-2006/084033 A1 | 8/2006 |
| WO | WO-2006/124956 A1 | 11/2006 |
| WO | WO-2006/127832 A2 | 11/2006 |
| WO | WO-2008/080162 A2 | 7/2008 |
| WO | WO-2009/031023 A2 | 3/2009 |

OTHER PUBLICATIONS

Abe, I. et al., Ellagitannins and hexahydroxyphenoyl esters as inhibitors of vertebrate squalene epoxidase, *J Nat Prod.*, 64:1010-1014 (2001).

Aviram, M. et al., Pomegranate phenolics from the peels, arils, and flowers are antiatherogenic: studies in vivo in atherosclerotic apolipoprotein E-deficient (E0) mice and in vitro in cultured macrophages and lipoproteins, *J Agric Food Chem.*, 56:1148-1157 (2008).

Chung, S.-K. et al., "A Prolyl Endopeptidase-Inhibiting Oxidant from *Phyllanthus ussurensis*", *Arch. Pharm. Res.*, 26(12):1024-1028 (Korea, 2003).

Hartman, R.E. et al., Pomegranate juice decreases amyloid load and improves behavior in a mouse model of Alzheimer's disease, *Neurobiol Dis.*, 24:506-515 (2006).

Kumar, S. et al., Protective effects of *Punica granatum* seeds extract against aging and scopolamine induced cognitive impairments in mice, *Afr J Tradit Complement Altern Med.*, 6:49-56 (2008).

Jun, M et al., Plant phenolics as beta-secretase (BACE1) inhibitors. *Food Sci Biotechnol* 15: 617-624 (2006).

Kwak, H-M. et al., Beta-secretase (BACE1) inhibitors from pomegranate (*Punica granatum*) husk, *Arch Pharm Res.*, 28:1328-1332 (2005).

(Continued)

*Primary Examiner* — Eric Olson
(74) *Attorney, Agent, or Firm* — Foley Hoag LLP

(57) ABSTRACT

Aspects of the invention relate to compounds, extracts and compositions thereof, and methods of using of the same, to treat neurodegenerative disorders and/or improve brain health. In certain embodiments, said compounds are pomegranate flavonoids.

32 Claims, 33 Drawing Sheets

(56) References Cited

OTHER PUBLICATIONS

Lansky, E. P. et al., "*Punica granatum* (pomegranate) and its potential for prevention and treatment of inflammation and cancer", *Journal of Ethnopharmacology*, 109:177-206 (Elsevier Ireland Ltd., 2006).

Lee, H.-J. et al., "β-Secretase (BACE1) Inhibitors from Sanguisorbae Radix", *Arch. Pharm. Res.*, 28(7):799-803 (Korea, 2005).

Lee, S.-H. et al., "Plant Phenolics as Prolyl Endopeptidase Inhibitors", *Arch. Pharm. Res.*, 30(7):827-833 (Korea, 2007).

Loren, D.J. et al., Maternal dietary supplementation with pomegranate juice is neuroprotective in an animal model of neonatal hypoxic-ischemic brain injury, *Pediatric Res.*, 57:858-864 (2005).

Martin, K. R. et al., "Development of a novel pomegranate standard and new method for the quantitative measurement of pomegranate polyphenols", *J. Sci. Food Agric.*, 89:157-162 (Society of Chemical Industry, USA, 2009).

Miranda, S. et al., The role of oxidative stress in the toxicity induced by amyloid-beta peptide in Alzheimer's disease. *Prog Neurobiol* 62: 633-648 (2000).

Rock, W. et al., Consumption of Wonderful variety pomegranate juice and extract by diabetic patients increases paraoxonase 1 association with high-density lipoprotein and stimulates its catalytic activities, *J Agric Food Chem.*, 56:8704-8713 (2008).

Sayre, L. M. et al., "Oxidative Stress and Neurotoxicity", *Chem. Res. Toxicol.*, 21:172-188 (American Chemical Society, 2008).

Seeram, N. et al., "Rapid large scale purification of ellagitannins from pomegranate husk, a by-product of the commercial juice industry", *Separation and Purification Technology* (Elsevier B.V., 2004).

Wang, KJ et al., New phenolic constituents from *Balanaphora polyandra* with radical-scavenging activity. *Chem. Biodiversity.* 3:1317-1324 (2006).

Yang, F. et al., "Curcumin Inhibits Formation of Amyloid β Oligomers and Fibrils, Binds Plaques, and Reduces Amyloid In Vivo", *J. Biol. Chem.*, 280(7):5892-5901 (JBC Papers in Press, USA, Feb. 18, 2005).

Extended European Search Report for related European application EP 10802978.6, dated Jan. 24, 2013.

Examination Report from related European application EP 10802978.6 dated Mar. 24, 2014.

Examination Report from related European application EP 10802978.6 dated Sep. 8, 2014.

Office Action from related Chinese application CN 201180067142.4 dated Jul. 3, 2014.

Office Action from related Japanese application 2012-521844 dated Aug. 26, 2014.

Search Report and Written Opinion generated by the Hungarian Patent Office for related Singapore patent application No. 201200477-6 dated May 29, 2014.

Third-party observation and prior-art disclosure from related Canadian patent application No. 2,768,963 filed Apr. 16, 2014.

Third-party observation filed in related European regional application EP 10802978.6.

Alzheimer's Disease, Merck Manual Online Edition, [retrieved on Jun. 8, 2012]. Retrieved from the Internet http://www.merckmanuals.com/home/print. Revision Feb. 2008, 14 pages.

Byrn et al., Solid-State Chemist of drugs, Chapter 11, 1999, 11 pages.

Fuhrman et al., "Pomegranate juice polyphenols increase recombinant paraoxonase-1 binding to high-density lipoprotein: studies in vitro and in diabetic patients," Nutrition, 26(4): 359-366 2010.

Full text of Impax Laboratories v. Aventis Pharmaceuticals, (Oct. 3, 2006) pp. 1-8.

Gove et al., Webster's Third New International Dictionary, 1963, p. 1798.

Johanningsmeier et al., "Pomegranate as a functional food and nutraceutical source," Annu Rev Food Sci Technol, 2: 181-201 (2011).

Jurenka, "Therapeutic Applications of Pomegranate (*Punica granatum* L.): A Review," Alt Med Rev, 13(2): 128-144 (2008).

Korean Search Report for International Application No. UAE/P/0079/2012, dated Mar. 30, 2017.

Lei et al., "Evidence of anti-obesity effects of the pomegranate leaf extract in high-fat diet induce obese mice," Int J Obesity, 31: 1023-1029 (2007).

Transmissible Spongiform Encephalopathies, [retrieved on Dec. 21, 2011]. Retrieved from the Internet http://www.minds.nih.gov. updated on Oct. 4, 2011.

Shukla, M. et al., "Bioavailable constituents/metabolites of pomegranate (*Punica granatum* L) preferentially inhibit COX2 activity ex vivo and IL-1beta-induced PGE2 production in human chondrocytes i n vitro," J Inflamm, 5(9):1-10 (2008).

Figure 12

| Fraction | Molecular Mass (Da) | IC$_{50}$ (µM) | Name |
|---|---|---|---|
| A3J | 783 | 10 | Punicalin |
| A1D | 785 | 11 | Pedunculagin |
| W12 | 1084 | 6 | Punicalagin |
| A3I | 786 | 9.3 | Compound A |
| A3G | 786 | 6.8 | Tellimagrandin |
|  | 368 | 65 | Corilagin |

| Eluent | Volume | Fraction | Flow (ml/min) |
|---|---|---|---|
| Water | 1.5 L | 1767-1 | 15 – 20 |
| Water/MeOH 8:2 | 400 ml | 1767-2 | |
| Water/MeOH 6:4 | 400 ml | 1767-3 | |
| Water/MeOH 4:6 | 400 ml | 1767-4 | |
| Water/MeOH 2:8 | 400 ml | 1767-5 | |
| MeOH | 200 ml | 1767-6 | |

Extract 1767 Subfractions HPLC Profiles

Compound A

Chemical Formula: $C_{34}H_{26}O_{22}$
Molecular Weight: 786,56

HPLC profiles of the resulting extracts

| Time (second) | % Water+0.1% Tri Fluoro Acetic acid (TFA) | % Acetonitril | Flow (ml/min) |
|---|---|---|---|
| 0:00 | 95 | 5 | 1 |
| 35:00 | 70 | 30 | |
| 50:00 | 40 | 60 | |
| 55:00 | 40 | 60 | |
| 60:00 | 0 | 100 | |
| 63:00 | 0 | 100 | |
| 65:00 | 95 | 5 | |
| 74:00 | 95 | 5 | | ns
COMPOUNDS, COMPOSITIONS AND METHODS FOR PROTECTING BRAIN HEALTH IN NEURODEGENERATIVE DISORDERS

RELATED APPLICATION

This application is a continuation of U.S. patent application Ser. No. 12/842,750, filed Jul. 23, 2010, which claims the benefit of priority to U.S. Provisional patent application Ser. No. 61/228,374, filed Jul. 24, 2009.

BACKGROUND

Neurodegenerative disorders and brain health are among the major emerging public health challenges facing our aging society. Alzheimer's disease (AD) is by far the most prevalent of the neurodegenerative disorders. Several aging pathologies, such as Parkinson's disease, Huntington's disease and ALS, are known to share some pathophysiology with Alzheimer's disease, including aberrant protein folding and oxidative stress. Sayre, L. M., G. Perry, et al. (2008). "Oxidative stress and neurotoxicity." *Chem Res Toxicol* 21(1): 172-88.

In addition to selective neuronal degeneration, AD is characterized pathologically by the presence of two hallmark lesions in the brain: extracellular senile plaques (SP) and intraneuronal neurofibrillary tangles (NFT). SP contain amyloid-β (Aβ) peptides, primarily Aβ(1-42); whereas, NFT are composed mainly of the microtubule-associated protein Tau in the form of paired helical filaments. The pathophysiology of AD is also characterized by increased production of soluble peptides of Amyloid Beta—peptides Aβ(1-40) and Aβ(1-42). Some recent findings suggest that neuronal toxicity and compromised synaptic transmission may be due to increased production of soluble oligomers of Aβ.

A need exists for compounds and compositions that treat neurodegenerative disorders and/or improve brain health. Ideally, such compounds would have good pharmaceutical properties, such as solubility, bioavailability and/or few side effects.

SUMMARY

Certain aspects of the invention relate compounds, extracts and compositions thereof, and methods of using them to treat neurodegenerative disorders and/or improve brain health. In certain embodiments, said compounds are pomegranate flavonoids. In certain embodiments, said compounds, extracts, and/or compositions may be used for the treatment, management or prevention of a disease or condition associated with the damage induced by fibril formation, or the increased risk of fibril formation.

In one aspect, the invention relates to a composition comprising a compound or extract of the invention, such as a pharmaceutical composition, a nutraceutical formulation, a medical food (also known as dietary food for special medical purpose), a functional food, a food additive, or a dietary supplement (also known as phytomedical product), comprising one or more anti-aggregation compounds of the invention. The compositions may also contain an additional therapeutic agent, or may be administered in combination with another therapeutic compound. Other aspects of the invention relate to packaged products containing the above-mentioned compositions and a label and/or instructions for use in preventing aggregation in a patient at risk, for the treatment of a disease or condition associated with damage to the brain associated with typical aging diseases and/or for preventing and/or managing associated cell death.

Additional aspects, embodiments, and advantages of the invention are discussed below in detail. Moreover, the foregoing information and the following detailed description are merely illustrative examples of various aspects and embodiments of the invention, and are intended to provide an overview or framework for understanding the nature and character of the claimed aspects and embodiments. The accompanying drawings are included to further understanding of the various aspects and embodiments, and are incorporated in and constitute a part of this specification. The drawings, together with the remainder of the specification, serve to explain principles and operations of the described and claimed aspects and embodiments. Various aspects of at least one embodiment are discussed below with reference to the accompanying figures. The figures are provided for the purposes of illustration and explanation and are not intended as a definition of the limits of the invention.

BRIEF DESCRIPTION OF THE FIGURES

FIG. 12 depicts molecules identified in the extracts as bioactive as well as their $IC_{50}$ values for inhibiting aggregation of $A\beta_{25-35}$.

All subfractions were assayed at 30 μg/mL. Subfractions 1767-2 and 1767-3 exhibit the highest activities; as they also display high similarities in their HPLC profile, they were pooled for further fractionation and analysis.

Figure 24:
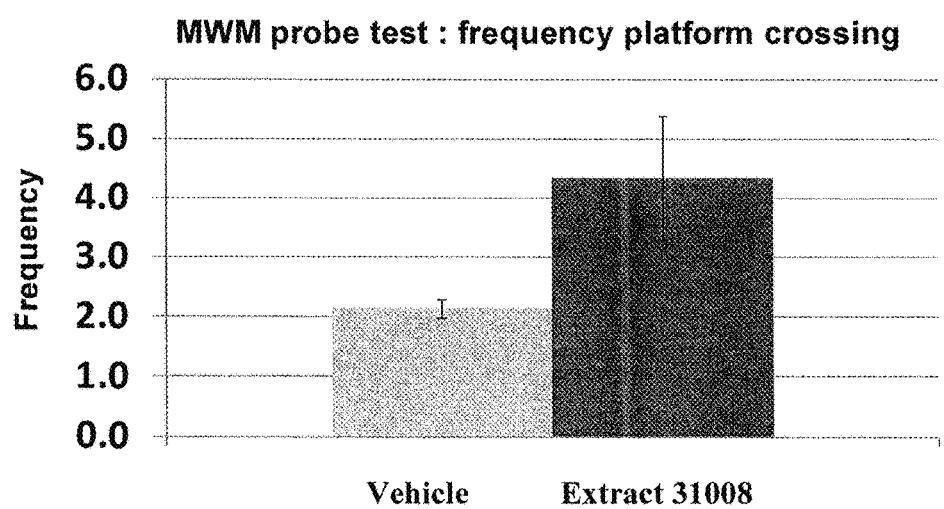

FIG. 24 depicts the result of the Morris Water Maze probe test at the end of a 3-month treatment period with a pomegranate extract 31008 in a mouse AD model (administration beginning at four months).

Figure 25:
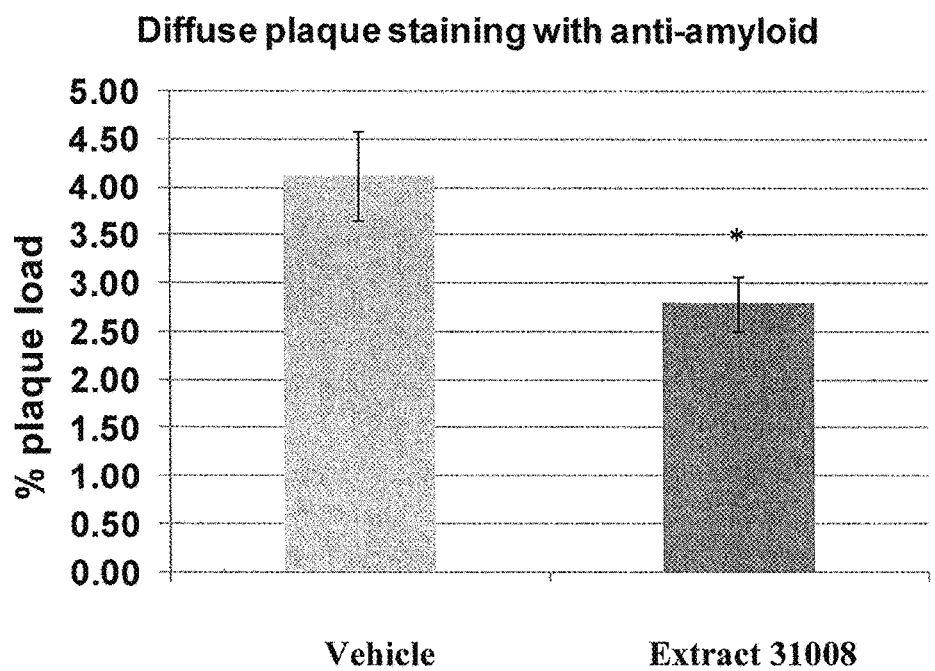

FIG. 25 depicts the results of mouse brain section staining for diffuse amyloid plaques at the end of a 3-month treatment period with a pomegranate extract 31008 in a mouse AD model (administration beginning at four months).

Figure 26:
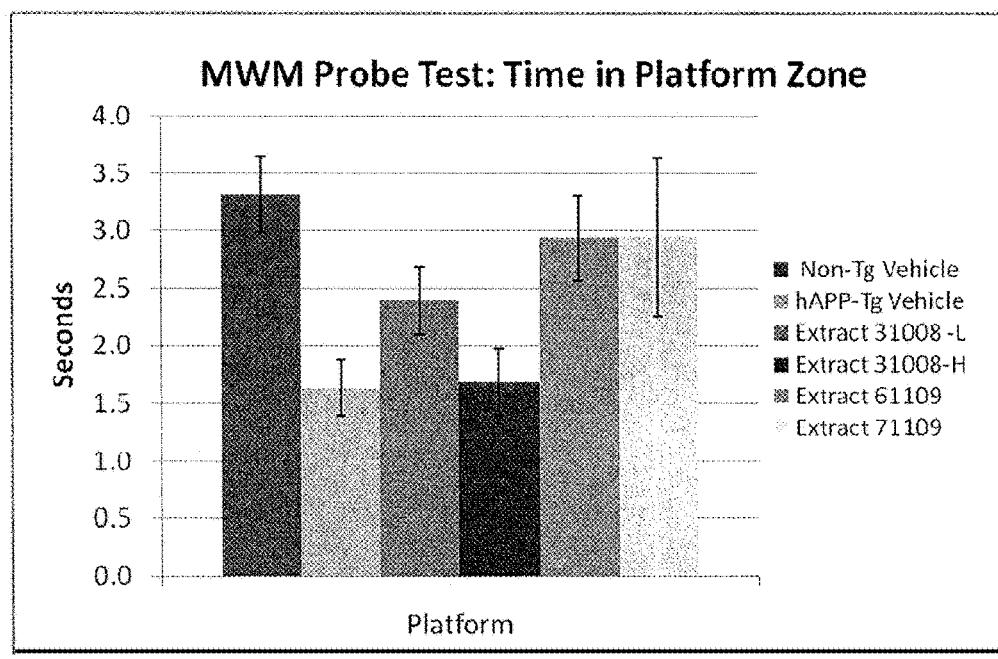

FIG. 26 depicts the result of the Morris Water Maze probe test at the end of a 3-month treatment period with punicalagin or pomegranate extract 31008 (at two different doses, low and high), extract 61109 and extract 71109, in a mouse AD model (administration beginning at two months).

Figure 27:
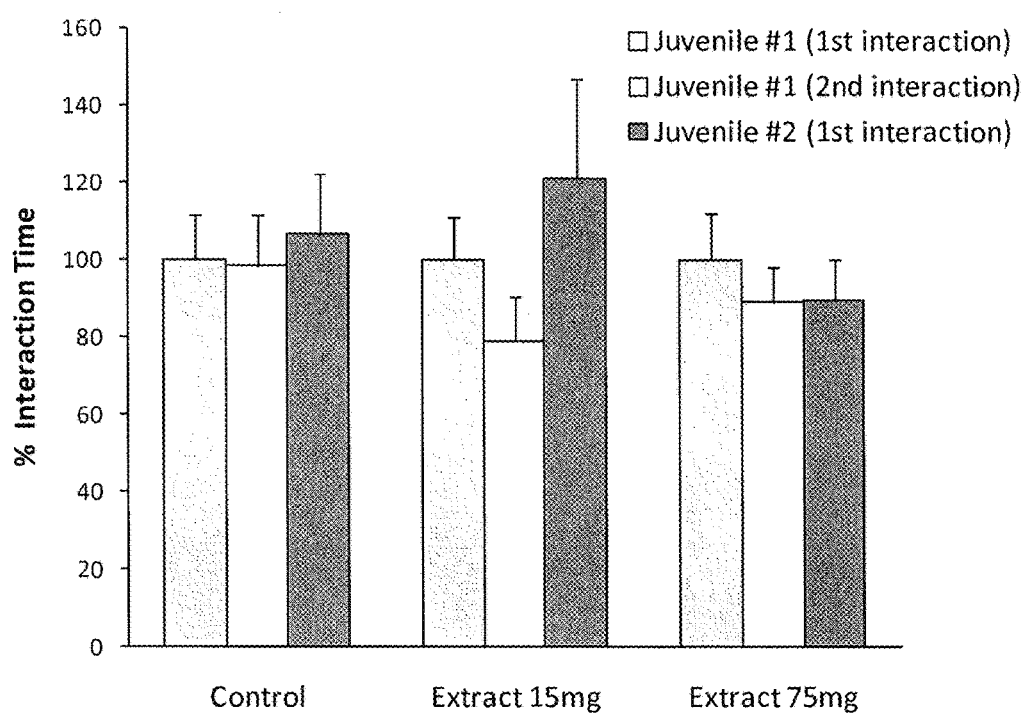

FIG. 27 depicts results of a social recognition study with aged rats (wherein the extract is 31008).

Figure 28:
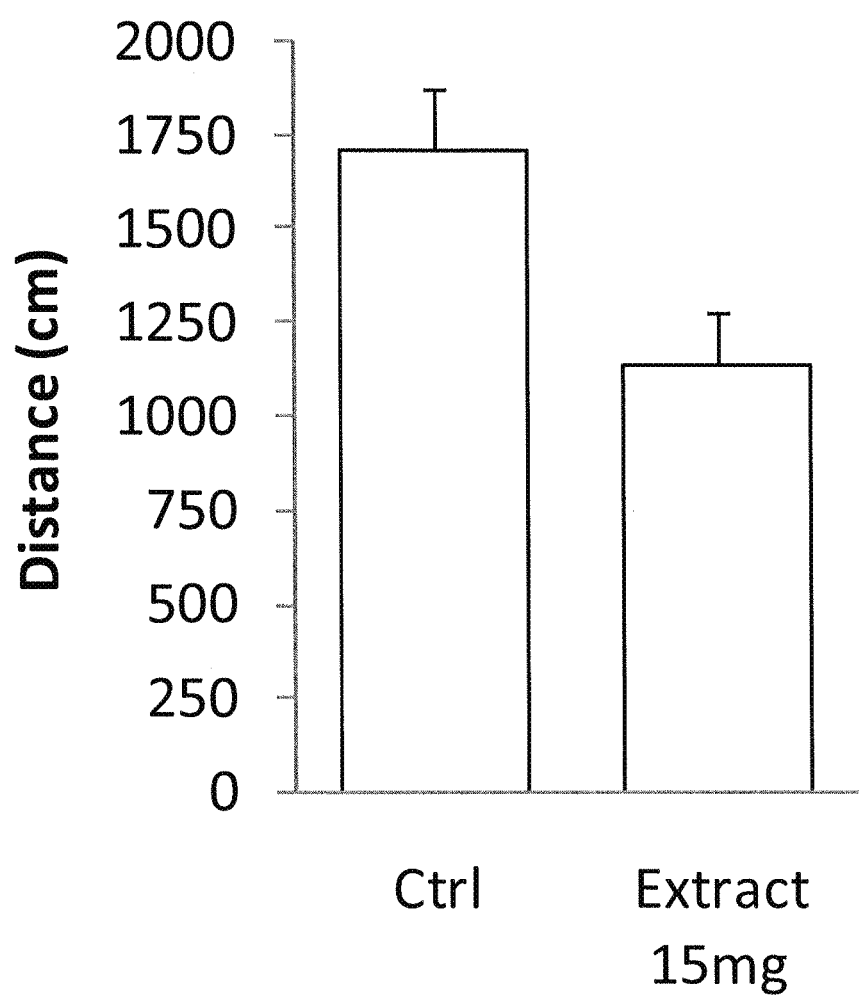

FIG. 28 depicts results of a Morris Water Maze reversal test with aged rats (wherein the extract is 31008 and the dosing is 30 μg·mL).

Figure 29:
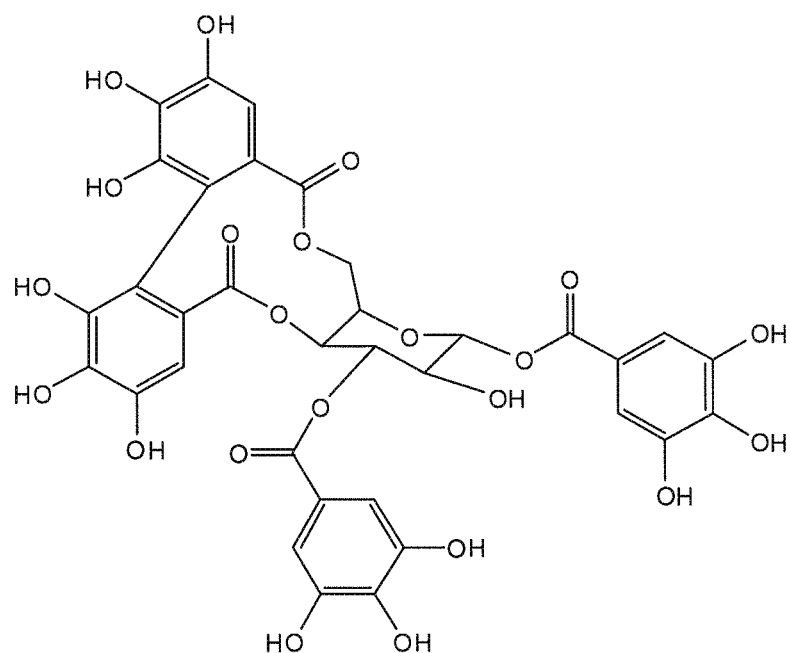

FIG. 29 depicts Compound A.

Figure 30:
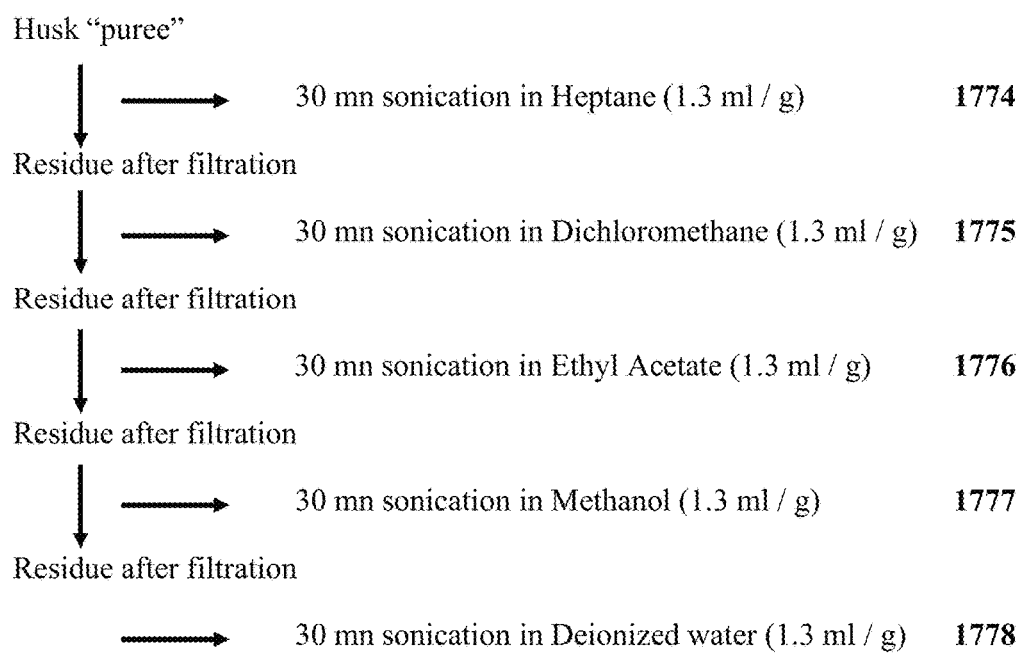
Figure 30:
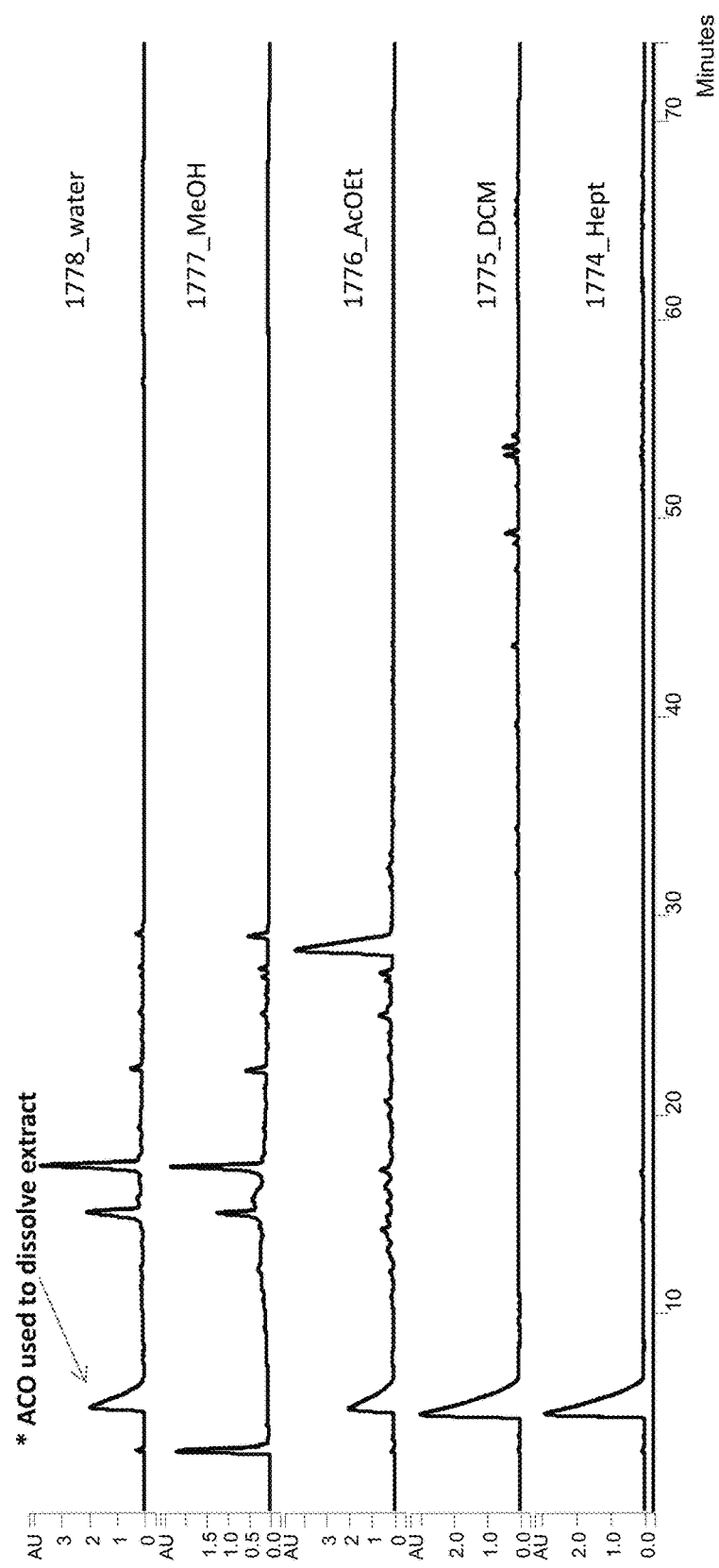

FIG. 30 depicts a flowchart showing an ultra sound assisted sequential pomegranate husk extraction by various solvent endowed with increasing polarity; and HPLC profiles of the resulting extracts. These profiles were obtained from a Varian analytic HPLC equipped with a Diode Array Detector (DAD) using a 250×4.6 mm, Ø0.5 mm "XRS pursuit" diphenyl column. The solvent and gradient used are shown in FIG. 31.

Figure 31:
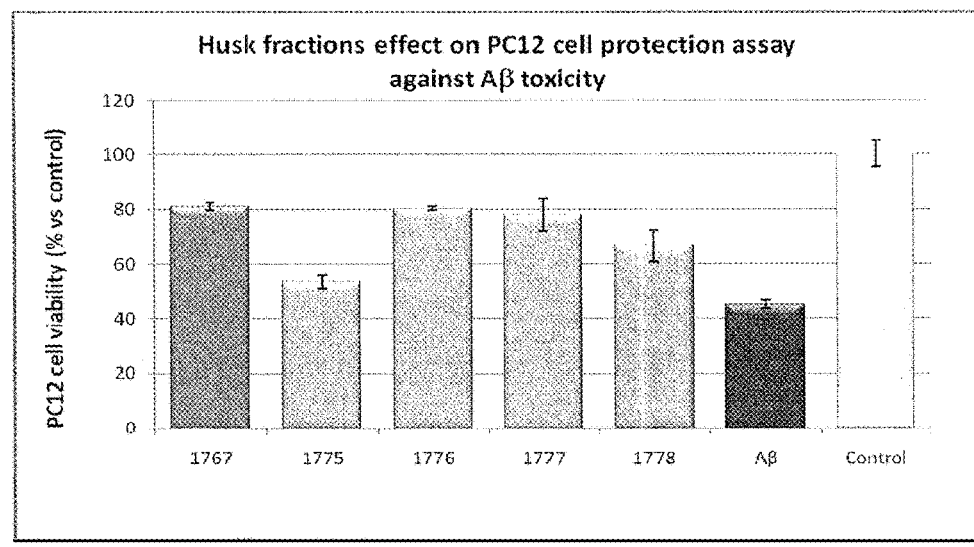

FIG. 31 depicts the solvent and gradient used in to obtain the HLPC traces; and a graph showing the bioactivity of husk subfractions on PC12 cell survival against Aβ toxicity. All subfractions were assayed at 500 μg/mL. Fraction 1776 exhibits the highest activity and very interesting HPLC profile, distinct of that of 1777 and 1778 whose major peaks look like Punicalagin. This result may suggest that another compound, different from punicalagin may be able to protect PC12 cells from Aβ-induced toxicity. Therefore 1776 was selected for further fractionation. Tellimagrandin was identified in extract fraction 1776.

DETAILED DESCRIPTION

Certain aspects of the invention relate to compounds (as well as extracts and compositions containing the same) and methods for effective administration of said compounds, extracts or compositions to a subject in need thereof.

Amyloidosis

In certain embodiments, the compounds inhibit protein folding that causes Aβ peptide aggregation (i.e., amyloid plaque formation).

A number of incurable, ageing-related or degenerative diseases have been linked to a generic and fundamental pathogenic process of protein or peptide misfolding and aggregation called "amyloidosis". These include Alzheimer's, Parkinson's and Huntington's diseases and type II diabetes. The amyloid deposits present in these diseases consist of particular peptides that are characteristic for each of these diseases but regardless of their sequence the amyloid fibrils have a characteristic β-sheet structure and share a common aggregation pathway. In each disease, a specific protein or peptide misfolds, adopts β-sheet structure and oligomerizes to form soluble aggregation intermediates en route to fibril formation ultimately forming insoluble amyloid fibres, plaques or inclusions. These insoluble forms of the aggregated protein or peptide form by the intermolecular association of β-strands into β-sheets. Recent evidence suggests that the soluble amyloid oligomers may be the principal cause of neurotoxicity.

The amyloidoses are defined as diseases in which normally soluble proteins accumulate in various tissues as insoluble deposits of fibrils that are rich in β-sheet structure and have characteristic dye-binding properties. Although the specific polypeptides that comprise the deposits are different for each amyloidosis, the disorders have several key features in common. The most prominent of these is the ability of proteins that are highly soluble in biological fluids to be gradually converted into insoluble filamentous polymers enriched in β-pleated sheet conformation.

Furthermore, they tend to form by a similar molecular mechanism (by the intermolecular association of β-strands into extended β-sheets), so they tend to share a similar molecular structure and a common ability to bind certain dyes, such as Congo Red and Thioflavin T.

These diseases and disorders, which are collectively referred to herein as "amyloid-related diseases", fall into two main categories: (a) those which affect the brain and other parts of the central nervous system; and (b) those which affect other organs or tissues around the body.

Examples of amyloid-related diseases which fall under these two categories are listed in the following two sections; however, many other examples of rare, hereditary amyloid-related diseases are known which are not included here, and additional forms of amyloid-related disease are likely to be discovered in future.

Neurodegenerative Diseases Associated with Amyloidosis

Many different neurodegenerative diseases are associated with the misfolding and aggregation of a specific protein or peptide in a particular part of the brain, or elsewhere in the central nervous system, depending on the specific disease. Examples of such diseases follow.

Various forms of Alzheimer's disease (AD) as well as Down's syndrome, hereditary cerebral hemorrhage with amyloidosis (HCHWA, Dutch type), cerebral amyloid angiopathy, and possibly also mild cognitive impairment and other forms of dementia are associated with the aggregation of a 40/42-residue peptide called β-amyloid, Aβ(1-40) or Aβ(1-42), which forms insoluble amyloid fibres and plaques in the cerebral cortex, hippocampus or elsewhere in the brain, depending on the specific disease. Alzheimer's disease is also associated with the formation of neurofibrillary tangles by aggregation of a hyperphosphorylated protein called tau, which also occurs in frontotemporal dementia (Pick's disease).

Parkinson's disease (PD), dementia with Lewy bodies (DLB), and multiple system atrophy (MSA) are associated with the aggregation of a protein called α-synuclein, which results in the formation of insoluble inclusions called "Lewy bodies". Huntington's disease (HD), spinal and bulbar muscular atrophy (SBMA, also known as Kennedy's disease), dentatorubral pallidoluysian atrophy (DRPLA), different forms of spinocerebellar ataxia (SCA, types 1, 2, 3, 6 and 7), and possibly several other inheritable neurodegenerative diseases are associated with the aggregation of various proteins and peptides that contain abnormally expanded glutamine repeats (extended tracts of polyglutamine). Creutzfeldt-Jakob disease (CJD), bovine spongiform encephalopathy (BSE) in cows, scrapie in sheep, kuru, Gerstmann-Straussler-Scheinker disease (GSS), fatal familial insomnia, and possibly all other forms of transmissible encephalopathy are associated with the self-propagating misfolding and aggregation of prion proteins.

Amyotrophic lateral sclerosis (ALS), and possibly also some other forms of motor neuron disease (MND) are associated with the aggregation of a protein called superoxide dismutase.

Familial British dementia (FBD) and familial Danish dementia (FDD), respectively, are associated with aggregation of the ABri and ADan peptide sequences derived from the BRI protein.

Hereditary cerebral hemorrhage with amyloidosis (HCHWA, Icelandic type) is associated with the aggregation of a protein called cystatin C.

Systemic Diseases Associated with Amyloidosis

In addition to the neurodegenerative diseases listed above, a wide variety of systemic ageing-related or degenerative diseases are associated with the misfolding and aggregation of a particular protein or peptide in various other tissues around the body (i.e., outside of the brain). Examples of such diseases follow.

Type II Diabetes (also known as adult-onset diabetes, or non-insulin dependent diabetes mellitus) is associated with the aggregation of a 37-residue peptide called the islet amyloid polypeptide (IAPP, or "amylin"), which forms insoluble deposits that are associated with the progressive destruction of insulin-producing $\beta$ cells in the islets of Langerhans within the pancreas.

Dialysis-related amyloidosis (DRA) and prostatic amyloid are associated with the aggregation of a protein called $\beta_2$-microglobulin, either in bones, joints and tendons in DRA, which develops during prolonged periods of hemodialysis, or within the prostate in the case of prostatic amyloid.

Primary systemic amyloidosis, systemic AL amyloidosis and myeloma-associated amyloidosis are associated with the aggregation of immunoglobulin light chain (or in some cases immunoglobulin heavy chain) into insoluble amyloid deposits, which gradually accumulate in various major organs such as the liver, kidneys, heart and gastrointestinal (GI) tract.

Reactive systemic AA amyloidosis, secondary systemic amyloidosis, familial Mediterranean fever and chronic inflammatory disease are associated with the aggregation of serum amyloid A protein, which forms insoluble amyloid deposits that accumulate in major organs such as the liver, kidneys and spleen; Senile systemic amyloidosis (SSA), familial amyloid polyneuropathy (FAP) and familial amyloid cardiomyopathy (FAC) are associated with the misfolding and aggregation of different mutants of transthyretin protein (TTR), which form insoluble inclusions in various organs and tissues such as the heart (especially in FAC), peripheral nerves (especially in FAP) and gastrointestinal (GI) tract. Another form of familial amyloid polyneuropathy (FAP, type II) is associated with the aggregation of apolipoprotein AI in the peripheral nerves; Familial visceral amyloidosis and hereditary non-neuropathic systemic amyloidosis are associated with misfolding and aggregation of various mutants of lysozyme, which form insoluble deposits in major organs such as the liver, kidneys and spleen.

Finnish hereditary systemic amyloidosis is associated with aggregation of a protein called gelsolin in the eyes (particularly in the cornea).

Fibrinogen $\alpha$-chain amyloidosis is associated with aggregation of the fibrinogen A $\alpha$-chain, which forms insoluble amyloid deposits in various organs, such as the liver and kidneys.

Insulin-related amyloidosis occurs by the aggregation of insulin at the site of injection in diabetics.

Medullary carcinoma of the thyroid is associated with the aggregation of calcitonin in surrounding tissues.

Isolated atrial amyloidosis is associated with the aggregation of atrial natriuretic peptide (ANP) in the heart.

Various forms of cataract are associated with the aggregation of $\gamma$-crystallin proteins in the lens of the eyes.

Pathogenic Mechanism of Amyloid-Related Diseases

While all of the amyloid-related diseases share the common pathogenic process of amyloidosis, the precise molecular mechanisms by which this generic process of protein/peptide misfolding and aggregation is linked to the progressive degeneration of affected tissues is unclear. In some cases, including many of the systemic amyloid-related diseases, it is thought that the sheer mass of insoluble protein or peptide simply overwhelms the affected tissues, ultimately leading to acute organ failure. In other cases, including most of the neurodegenerative diseases listed above, the symptoms of disease develop with the appearance of only very small aggregates. Therefore, it has been suggested that the insoluble deposits are inherently toxic and might cause the progressive destruction of cells, for example by causing inflammation and oxidative stress, or by directly interfering with cell membranes or other cellular components or processes.

Recently, it has been established that the specific proteins and peptides involved in at least some of these amyloid-related diseases form various soluble oligomeric species during their aggregation, which range in size from dimers and trimers to much larger species comprising tens or even hundreds or thousands of protein or peptide monomers. Moreover, the oligomers are inherently toxic to cells in vitro in the absence of insoluble aggregates, and they appear to share a common structural feature as they can all be recognized by the same antibody despite the fact that they may be formed by proteins or peptides with very different amino acid sequences.

The molecular structure of these toxic soluble oligomers is not known and the precise mechanism by which they kill cells is also unclear, but several theories have been proposed. According to one theory, called the "channel hypothesis," the oligomers form heterogeneous pores or leaky ion channels, which allow ions to flow freely through cell membranes, thereby destroying their integrity which ultimately causes cell death. Alternatively, or additionally, the oligomers may form protofibrils that kill cells by a similar or different mechanism.

Regardless of the precise pathogenic mechanism, however, an overwhelming amount of evidence has now been accumulated which suggests that the general process of protein/peptide aggregation is the primary cause of these and possibly other amyloid-related diseases.

The present invention relates to chemical compounds, extracts and compositions which are inhibitors of amyloid-related toxicity and, as such, will be useful in the treatment of amyloid-related diseases and disorders.

Early Detection of Amyloid-Related Diseases and Disorders

It is always desirable to detect diseases early in their progress. Early detection enables early treatment which has generally been proven to yield a higher success rate in treating various diseases. Recently, it has been discovered that analyzing peoples' eyes, and in particular the lenses of the eyes, can yield indications of various types of diseases. For example, measurements taken of light scattering within the eye has been shown to provide useful diagnostic information to detect and monitor the progress of diseases such as Alzheimer's disease. US Patent Application Publication No. 2008/0088795 and U.S. Pat. No. 7,107,092; both of which are hereby incorporated by reference in their entirety. In addition, changes in the brain measured with MRI and PET scans, ELISA assays, and diffraction-enhanced imaging (DEI), alone or combined with memory tests and detection of risk proteins in body fluids, may also lead to earlier and more accurate diagnosis of Alzheimer's.

Compounds of the Invention

One aspect of the invention relates to compounds s which when administered lead to the treatment or prevention of neurodegenerative disorders and/or the improvement of brain health. As discussed in more detail below, in certain embodiments the administration of the compound results in fewer depositions of amyloid fibrils in the brains of animals fed compositions which comprise one or more compounds of the invention; and resulted in an increase or restoration of memory in the animals fed the compositions comprising one or more compounds of the invention.

For example, compounds of the invention include Punicalin, Punicalagin, Pedunculagin, Tellimagrandin, Corilagin, Granatine A, Granatine B, Terminalin, Gallagyldilactone, and Compound A, as well as pharmaceutically acceptable salts, biologically active metabolites, solvates, hydrates, prodrugs, enantiomers or stereoisomers thereof.

The present invention also relates to a pure and isolated compound, or a pharmaceutically acceptable salt, biologically active metabolite, solvate, hydrate, prodrug, enantiomer or stereoisomer thereof; wherein the compound is represented by formula I:

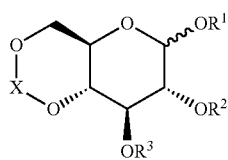

I wherein independently for each occurrence
X is

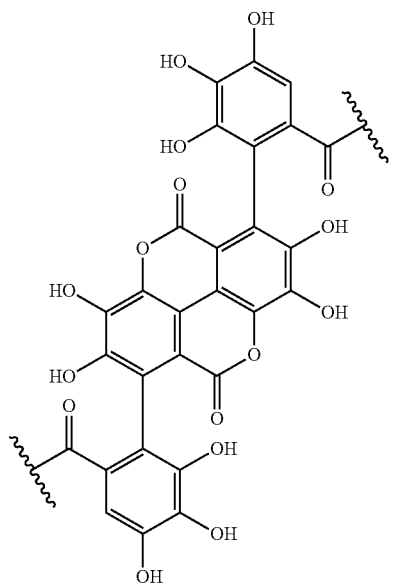

and

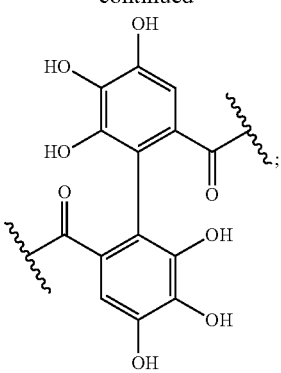

and $R^1$, $R^2$ and $R^3$ are each independently hydrogen, alkyl, aralkyl, alkylcarboxy, or a sugar; or $R^1$ is hydrogen, alkyl, aralkyl, alkylcarboxy,

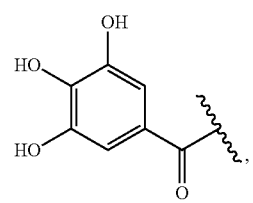 [SMILES: *C(=O)c1cc(O)c(O)c(O)c1]

or a sugar, $R^2$ is hydrogen or

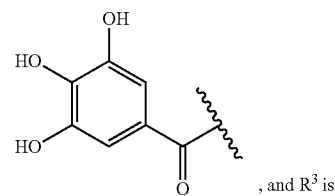

, and $R^3$ is

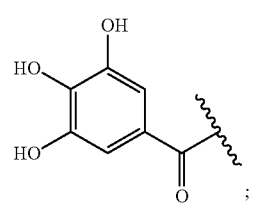

;

or $R^1$ is hydrogen, alkyl, aralkyl, alkylcarboxy, or a sugar, and $R^2$ and $R^3$ taken together are In certain embodiments, the present invention relates to any one of the aforementioned compounds, wherein X is

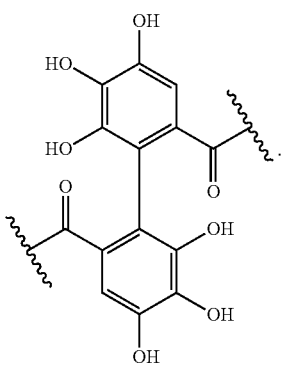 [SMILES: *C(=O)c1cc(O)c(O)c(O)c1-c1c(C(*)=O)cc(O)c(O)c1O]

In certain embodiments, the present invention relates to any one of the aforementioned compounds, wherein X is

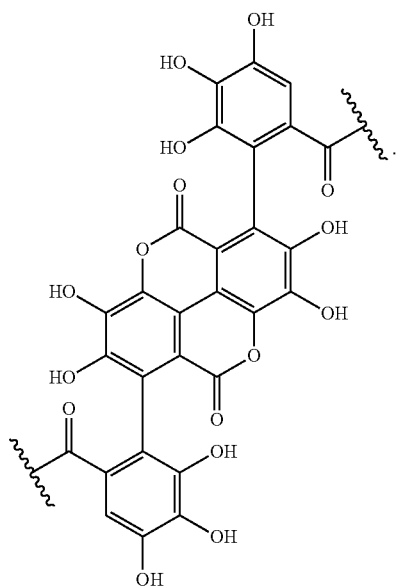 [SMILES: *C(=O)c1cc(O)c(O)c(O)c1-c1c(O)c(O)c2oc(=O)c3c(-c4c(C(*)=O)cc(O)c(O)c4O)c(O)c(O)c4oc(=O)c1c2c43]

In certain embodiments, the present invention relates to any one of the aforementioned compounds, wherein X is

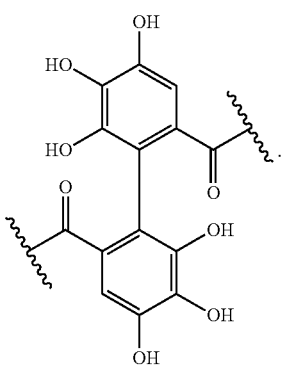 [SMILES: *C(=O)c1cc(O)c(O)c(O)c1-c1c(C(*)=O)cc(O)c(O)c1O]

In certain embodiments, the present invention relates to any one of the aforementioned compounds, wherein $R^1$ is hydrogen.

In certain embodiments, the present invention relates to any one of the aforementioned compounds, wherein $R^1$ is a sugar selected from the group consisting of allose ("All"), altrose ("Alt"), arabinose ("Ara"), erythrose, erythrulose, fructose ("Fru"), fucosamine ("FucN"), fucose ("Fuc"), galactosamine ("GalN"), galactose ("Gal"), galloyl-β-glucose, glucosamine ("GlcN"), glucosaminitol ("GlcN-ol"), glucose ("Glc"), glyceraldehyde, 2,3-dihydroxypropanal, glycerol ("Gro"), propane-1,2,3-triol, glycerone ("1,3-dihydroxyacetone"), 1,3-dihydroxypropanone, gulose ("Gul"), idose ("Ido"), lyxose ("Lyx"), mannosamine ("ManN"), mannose ("Man"), psicose ("Psi"), quinovose ("Qui"), quinovosamine, rhamnitol ("Rha-ol"), rhamnosamine ("RhaN"), rhamnose ("Rha"), ribose ("Rib"), ribulose ("Rul"), rutinose, sialic acid ("Sia" or "Neu"), sorbose ("Sor"), tagatose ("Tag"), talose ("Tal"), tartaric acid, erythraric/threaric acid, threose, xylose ("Xyl"), or xylulose ("Xul").

In certain embodiments, the present invention relates to any one of the aforementioned compounds, wherein $R^2$ is hydrogen.

In certain embodiments, the present invention relates to any one of the aforementioned compounds, wherein $R^2$ is a sugar selected from the group consisting of allose ("All"), altrose ("Alt"), arabinose ("Ara"), erythrose, erythrulose, fructose ("Fru"), fucosamine ("FucN"), fucose ("Fuc"), galactosamine ("GalN"), galactose ("Gal"), galloyl-β-glucose, glucosamine ("GlcN"), glucosaminitol ("GlcN-ol"), glucose ("Glc"), glyceraldehyde, 2,3-dihydroxypropanal, glycerol ("Gro"), propane-1,2,3-triol, glycerone ("1,3-dihydroxyacetone"), 1,3-dihydroxypropanone, gulose ("Gul"), idose ("Ido"), lyxose ("Lyx"), mannosamine ("ManN"), mannose ("Man"), psicose ("Psi"), quinovose ("Qui"), quinovosamine, rhamnitol ("Rha-ol"), rhamnosamine ("RhaN"), rhamnose ("Rha"), ribose ("Rib"), ribulose ("Rul"), rutinose, sialic acid ("Sia" or "Neu"), sorbose ("Sor"), tagatose ("Tag"), talose ("Tal"), tartaric acid, erythraric/threaric acid, threose, xylose ("Xyl"), or xylulose ("Xul").

In certain embodiments, the present invention relates to any one of the aforementioned compounds, wherein $R^3$ is hydrogen.

In certain embodiments, the present invention relates to any one of the aforementioned compounds, wherein $R^3$ is a sugar selected from the group consisting of allose ("All"), altrose ("Alt"), arabinose ("Ara"), erythrose, erythrulose, fructose ("Fru"), fucosamine ("FucN"), fucose ("Fuc"), galactosamine ("GalN"), galactose ("Gal"), galloyl-β-glucose, glucosamine ("GlcN"), glucosaminitol ("GlcN-ol"), glucose ("Glc"), glyceraldehyde, 2,3-dihydroxypropanal, glycerol ("Gro"), propane-1,2,3-triol, glycerone ("1,3-dihydroxyacetone"), 1,3-dihydroxypropanone, gulose ("Gul"), idose ("Ido"), lyxose ("Lyx"), mannosamine ("ManN"), mannose ("Man"), psicose ("Psi"), quinovose ("Qui"), quinovosamine, rhamnitol ("Rha-ol"), rhamnosamine ("RhaN"), rhamnose ("Rha"), ribose ("Rib"), ribulose ("Rul"), rutinose, sialic acid ("Sia" or "Neu"), sorbose ("Sor"), tagatose ("Tag"), talose ("Tal"), tartaric acid, erythraric/threaric acid, threose, xylose ("Xyl"), or xylulose ("Xul").

In certain embodiments, the present invention relates to any one of the aforementioned compounds, wherein $R^1$, $R^2$ and $R^3$ are each independently hydrogen, alkyl, aralkyl, alkylcarboxy, or a sugar.

In certain embodiments, the present invention relates to any one of the aforementioned compounds, wherein $R^1$, $R^2$ and $R^3$ are hydrogen.

In certain embodiments, the present invention relates to any one of the aforementioned compounds, wherein $R^1$ is hydrogen, alkyl, aralkyl, alkylcarboxy,

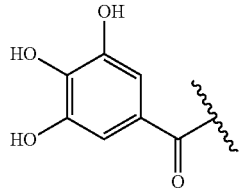

or a sugar, $R^2$ is hydrogen or

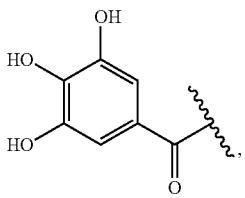 [SMILES: *C(=O)c1cc(O)c(O)c(O)c1]

and $R^3$ is

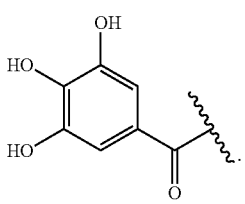 [SMILES: *C(=O)c1cc(O)c(O)c(O)c1]

In certain embodiments, the present invention relates to any one of the aforementioned compounds, wherein $R^1$ is hydrogen, $R^2$ is

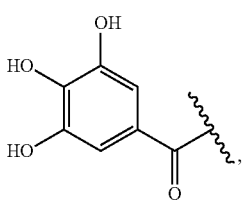 [SMILES: *C(=O)c1cc(O)c(O)c(O)c1]

and $R^3$ is

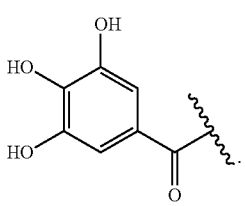 [SMILES: *C(=O)c1cc(O)c(O)c(O)c1]

In certain embodiments, the present invention relates to any one of the aforementioned compounds, wherein $R^1$ is

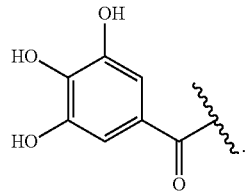

In certain embodiments, the present invention relates to any one of the aforementioned compounds, wherein $R^1$ is

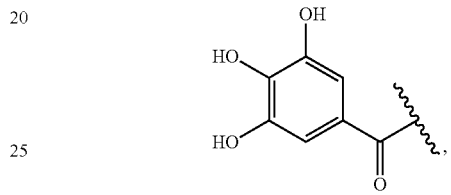

$R^2$ is hydrogen, and $R^3$ is

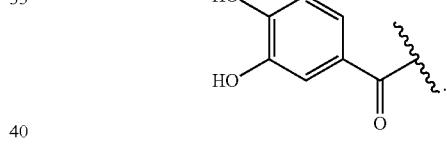

In certain embodiments, the present invention relates to any one of the aforementioned compounds, wherein $R^1$ is hydrogen, alkyl, aralkyl, alkylcarboxy, or a sugar, and $R^2$ and $R^3$ taken together are

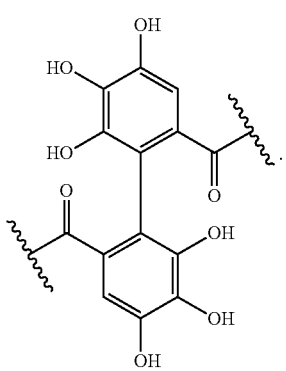 [SMILES: *C(=O)c1cc(O)c(O)c(O)c1-c1c(C(*)=O)cc(O)c(O)c1O]

In certain embodiments, the present invention relates to any one of the aforementioned compounds, wherein $R^1$ is hydrogen, and $R^2$ and $R^3$ taken together are

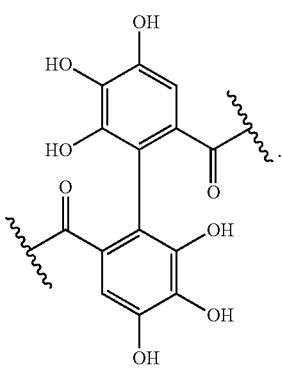 [SMILES: *C(=O)c1cc(O)c(O)c(O)c1-c1c(C(*)=O)cc(O)c(O)c1O]

The invention also encompasses multimers of formula I, such as dimers in which two monomers of the formula are bonded as described in Reed, J. D., C. G. Krueger, et al. (2005). "MALDI-TOF mass spectrometry of oligomeric food polyphenols." *Phytochemistry* 66(18): 2248-63. The dimers are naturally occurring dimers of ellagitannins; their detailed structures are not fully elucidated, but they contain the basic structural backbone identified in this invention. Trimers, tetramers and larger oligomers are also encompassed in the present invention. In otherwords, multimers with, for example, two, three, four, five, six, seven, eight, nine, ten, or more repeats are encompased in the present invention.

Certain compounds of the invention which have acidic substituents may exist as salts with pharmaceutically acceptable acids or bases. Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Exemplary pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds of the invention and their salts may exist in more than one crystal form and the present invention includes each individual crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Exemplary pro-drugs release an hydroxyl of a compound of the invention wherein the free hydrogen of a hydroxyl is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$) alkoxycarbonyloxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

A compound may be isolated and extracted (i.e., separated from the compounds with which it naturally occurs), or it may be synthetically prepared (i.e., manufactured using a process synthesis) so that in any cases the level of contaminating compounds or impurities does not detract from or adversely effect to the effectiveness of the compound of the invention.

Certain compounds of the invention may be extracted from natural sources such as *Punica granatum* juice, leaves, bark, pericarp, or peel. Lansky, E. P. and R. A. Newman (2007). "*Punica granatum* (pomegranate) and its potential for prevention and treatment of inflammation and cancer." *J Ethnopharmacol* 109(2): 177-206. Some of the compound may also be isolated from Walnuts, *Euscaphis japonica, Geum japonicum* Thunb. var. *chinense*, Blackberries (*Rubus* sp.), *Juglans regia, Pimenta dioica, Quercus, Acer, Cornus officinalis, Emblica officinalis* (amla), *Terminalia chebula* Retz, and *Terminalia catappa* L, as well as other similar species.

For example, Punicalin, Punicalagin, Pedunculagin and Tellimagrandin have been previously isolated and characterized. Tanaka, K., G. Nonaka, et al. (1986). "Tannins and Related Compounds. XLI. 1) Isolation and Characterization of Novel Ellagitannins, Punicacorteins A, B, C, and Punigluconin from the bark of *Punica granatum* L." *Chem. Pharm. Bull* 34(2): 656-663; Tanaka, K., G. Nonaka, et al. (1986). "Tannins and Related Compounds. XLI. 1). Revision of the Structures of Punicalin and Punicalagin, and Isolation and Characterization of 2-O-Galloylpunicalin from the Bark of *Punica granatum* L." *Chem. Pharm. Bull* 34(2): 650-655; and Satomi, H., K. Umemura, et al. (1993). "Carbonic anhydrase inhibitors from the pericarps of *Punica granatum* L." *Biol Pharm Bull* 16(8): 787-90.

In certain embodiments, the compound of the invention is at least about 1% pure up to about 99% pure. In certain embodiments, the compound of the invention is at least about 10% pure. In certain embodiments, the compounds is at least about 20% pure. In certain embodiments, the compounds is at least about 30% pure. In certain embodiments, the compounds is at least about 40% pure. In certain embodiments, the compounds is at least about 50% pure. In certain embodiments, the compounds is at least about 60% pure. In certain embodiments, the compounds is at least about 70% pure. In certain embodiments, the compounds is at least about 80% pure. In certain embodiments, the compounds is at least about 90% pure. In certain embodiments, the compounds is at least about 95% pure. In certain embodiments, the compounds is at least about 99% pure. In certain embodiments, such extracts which contain one or more compounds of the invention at any of the aforementioned purities may be also suitable for use as or in functional foods and dietary supplements. Such extracts are discussed more fully below.

Figure 1:
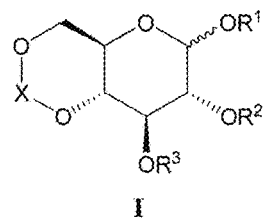
FIG. 1 depicts selected compounds of the invention.
Figure 2:
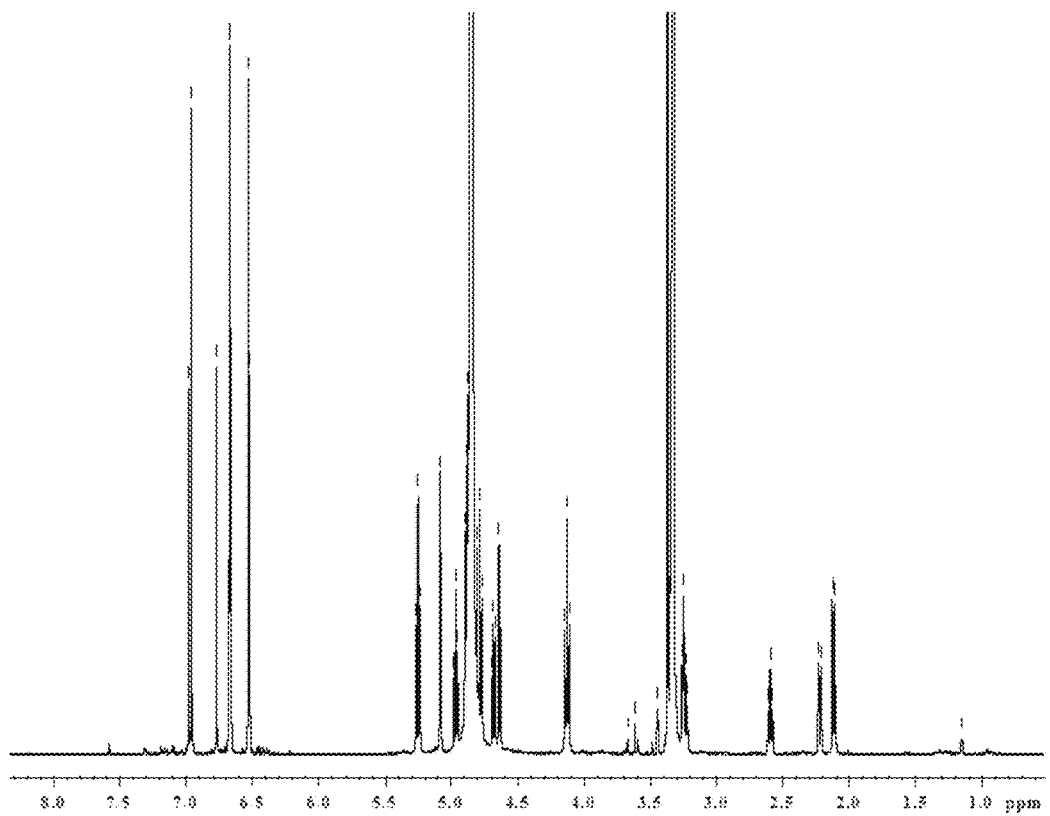
FIG. 2 depicts the $^1$H NMR spectrum of Punicalagin.
Figure 3:
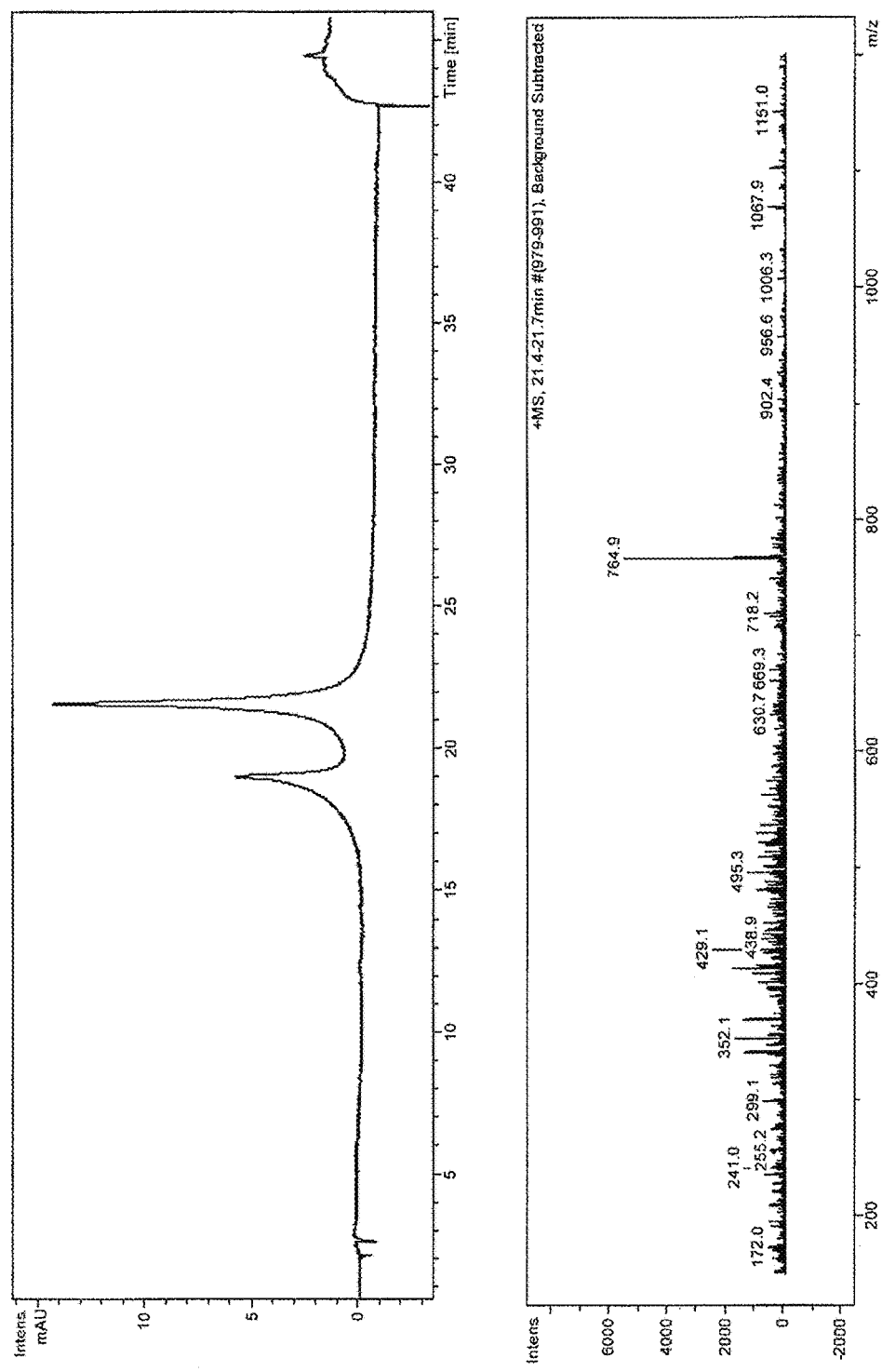
FIG. 3 depicts the mass spectrum of Punicalagin.

One aspect of the invention relates to a compound, or a pharmaceutically acceptable salt, biologically active metabolite, solvate, hydrate, prodrug, enantiomer or stereoisomer thereof, which generates the spectra in FIGS. 2 and 3.

Figure 4:
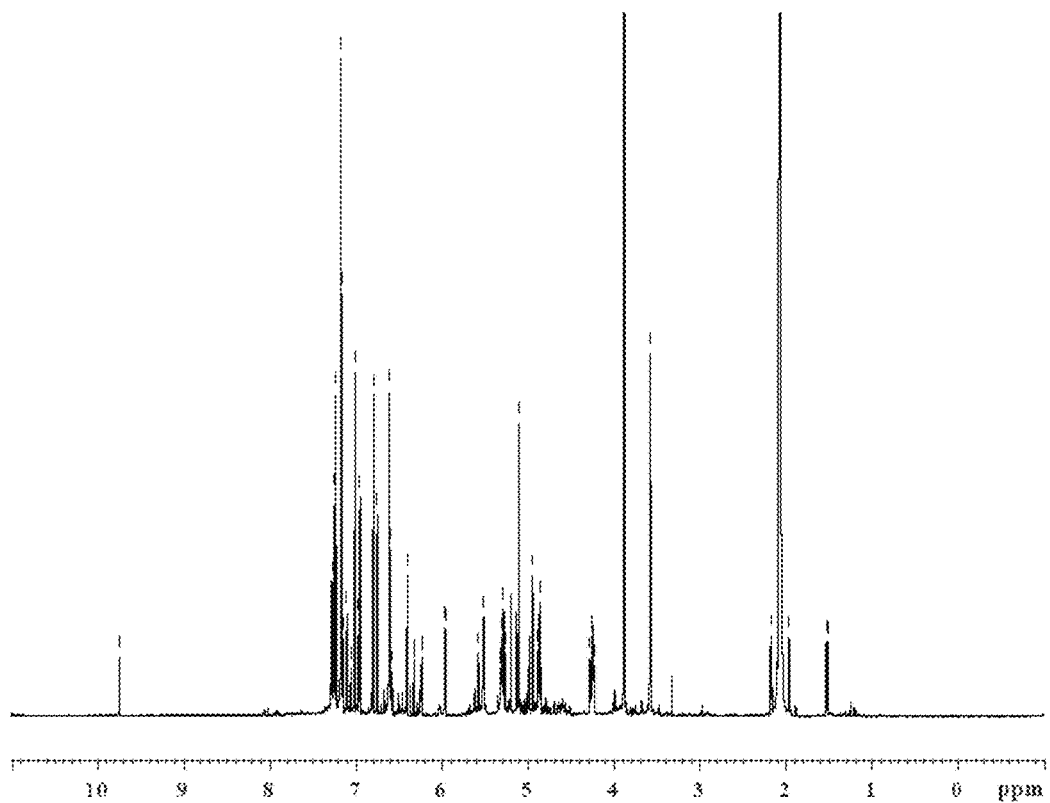
FIG. 4 depicts the $^1$H NMR spectrum of Punicalin.
Figure 5:
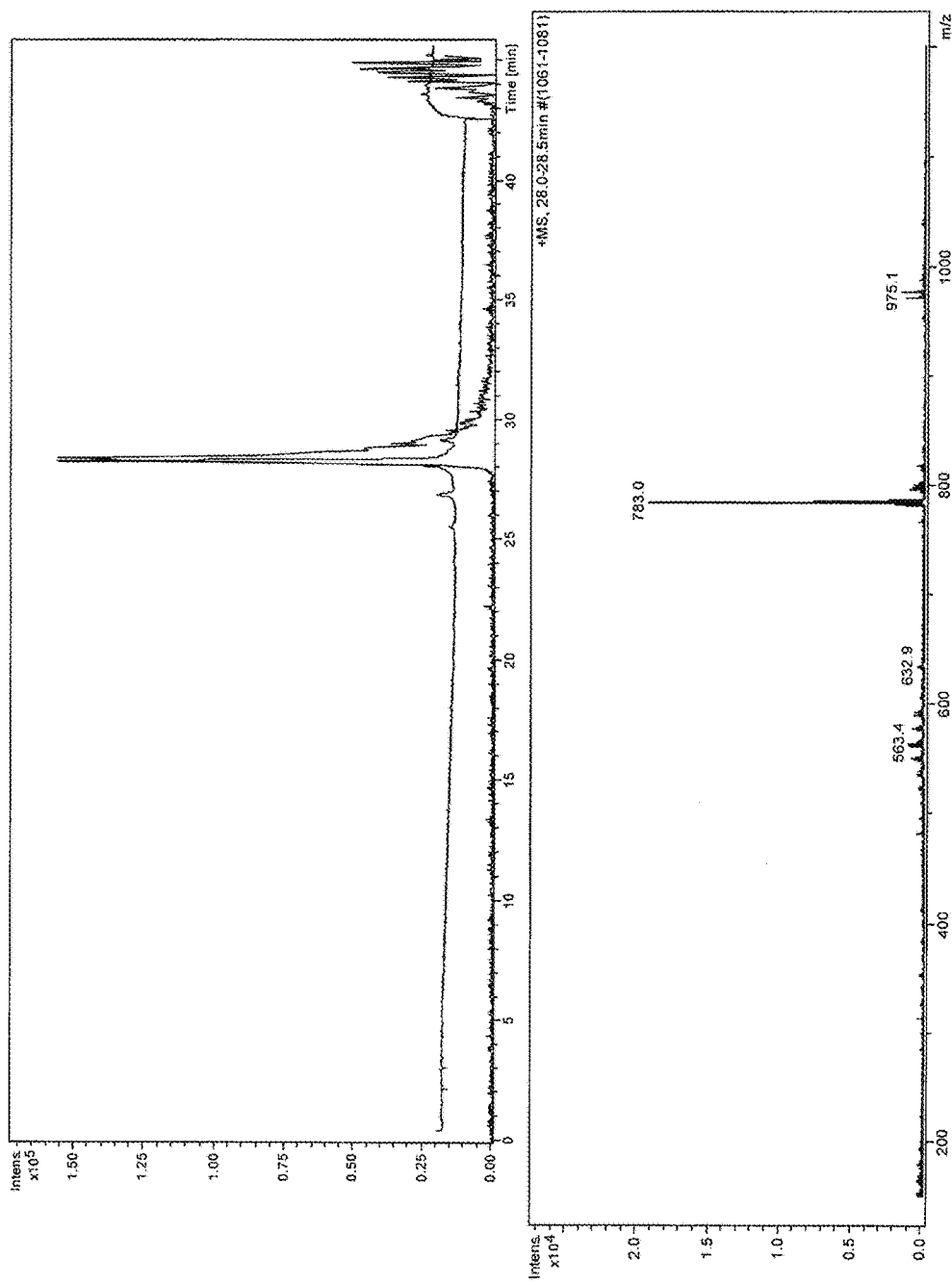
FIG. 5 depicts the mass spectrum of Punicalin.

One aspect of the invention relates to a compound, or a pharmaceutically acceptable salt, biologically active metabolite, solvate, hydrate, prodrug, enantiomer or stereoisomer thereof, which generates the spectra in FIGS. 4 and 5.

Figure 6:
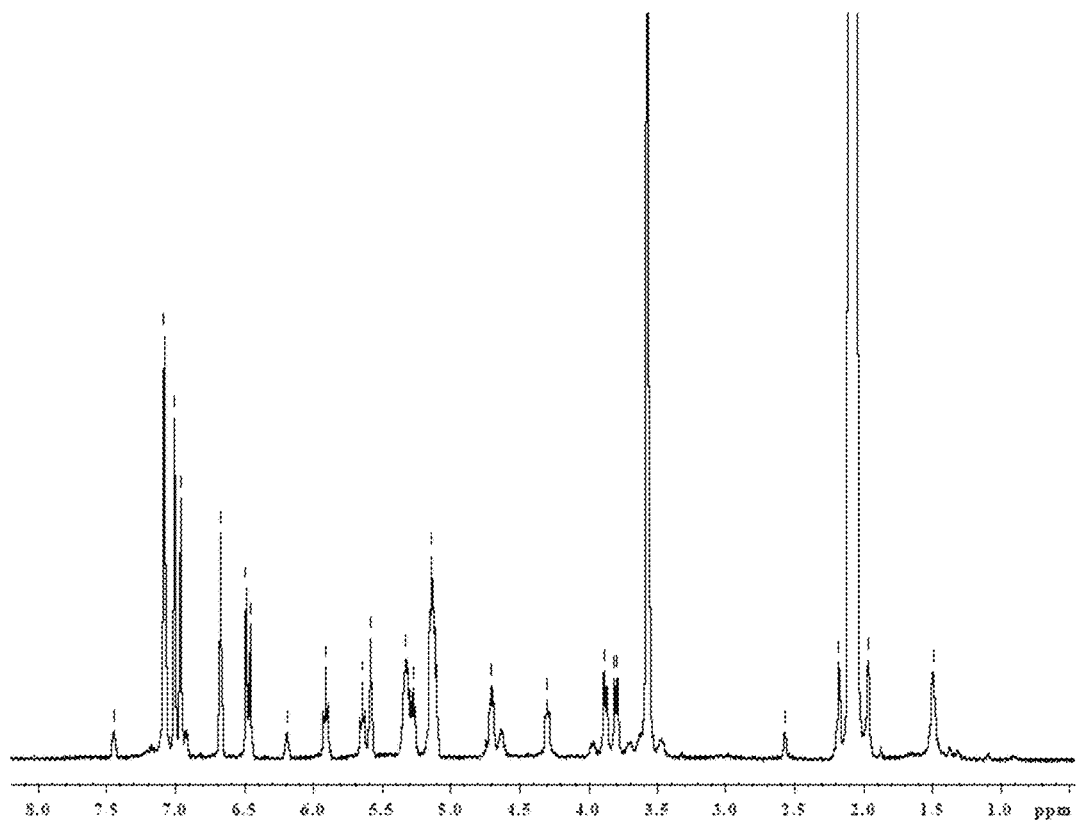
FIG. 6 depicts the $^1$H NMR spectrum of Tellimagrandin.
Figure 7:
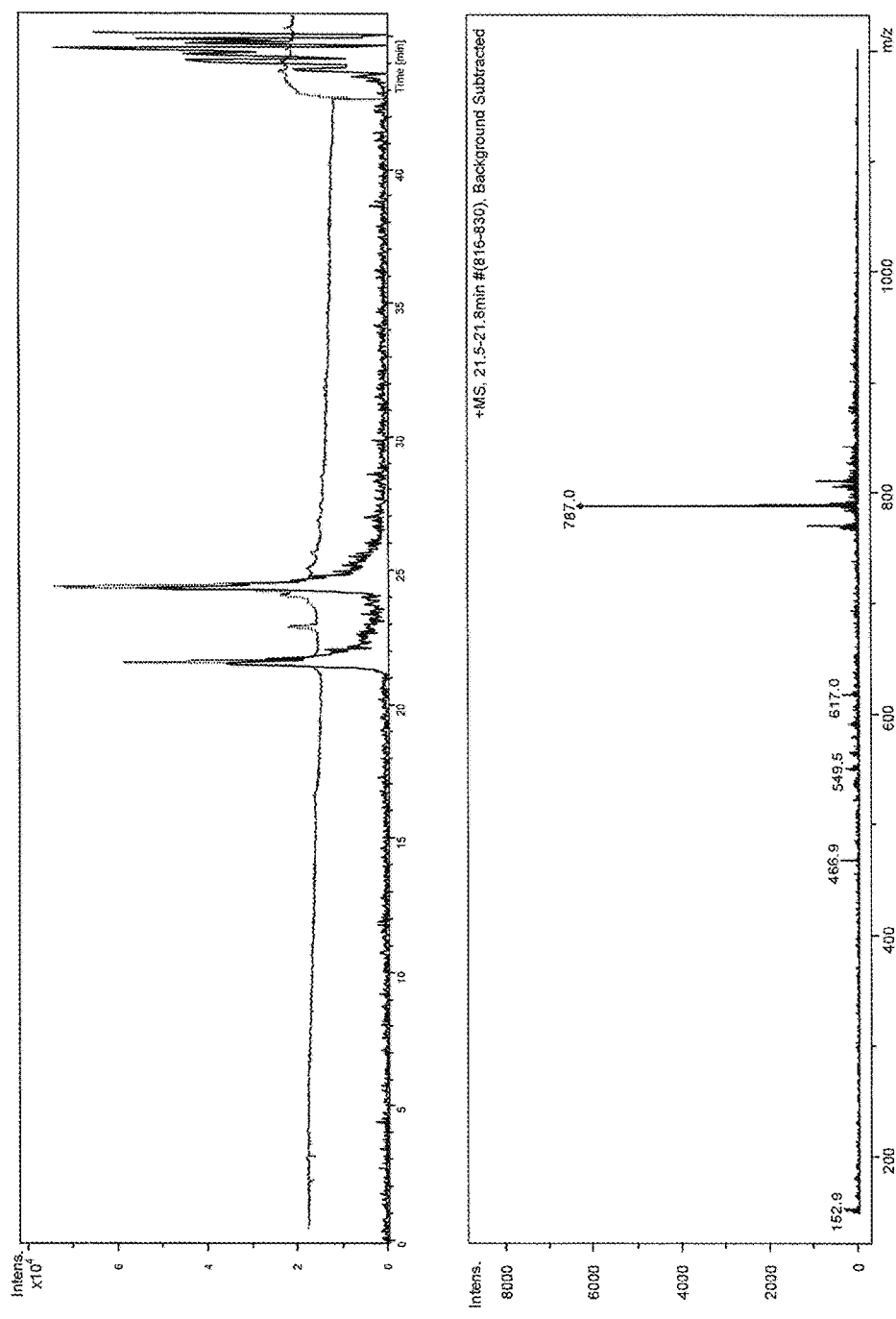
FIG. 7 depicts the mass spectrum of Tellimagrandin.

One aspect of the invention relates to a compound, or a pharmaceutically acceptable salt, biologically active metabolite, solvate, hydrate, prodrug, enantiomer or stereoisomer thereof, which generates the spectra in FIGS. 6 and 7.

Figure 8:
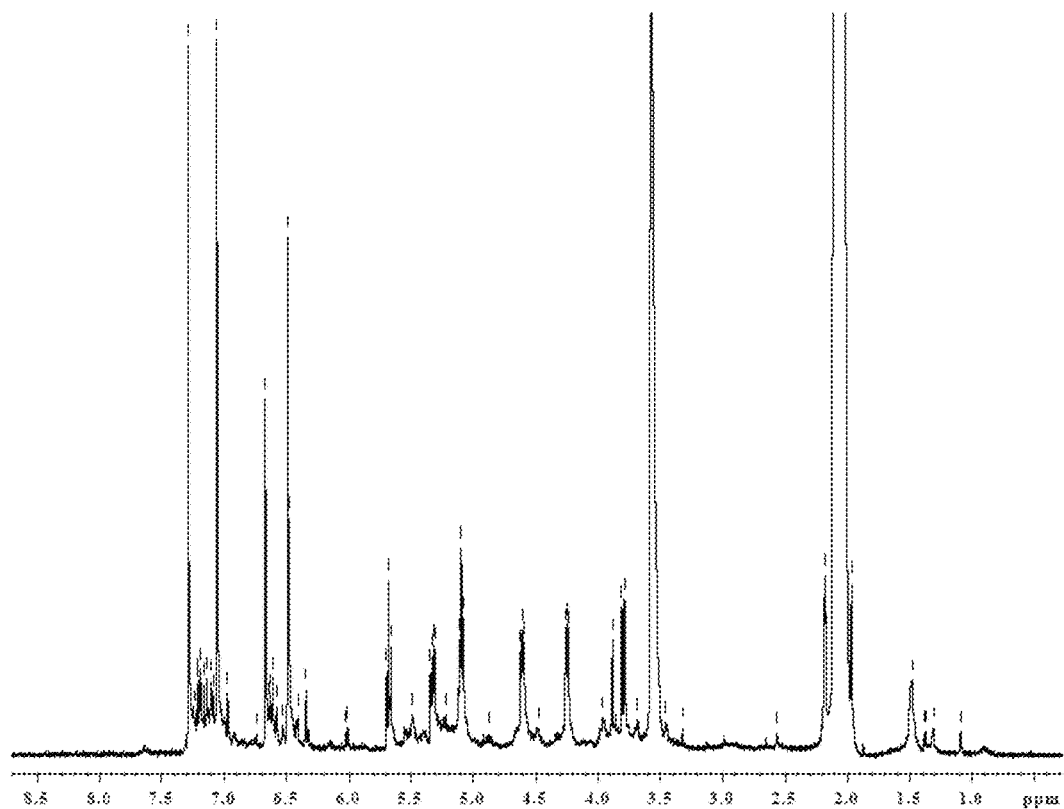
FIG. 8 depicts the $^1$H NMR spectrum of Compound A.
Figure 9:
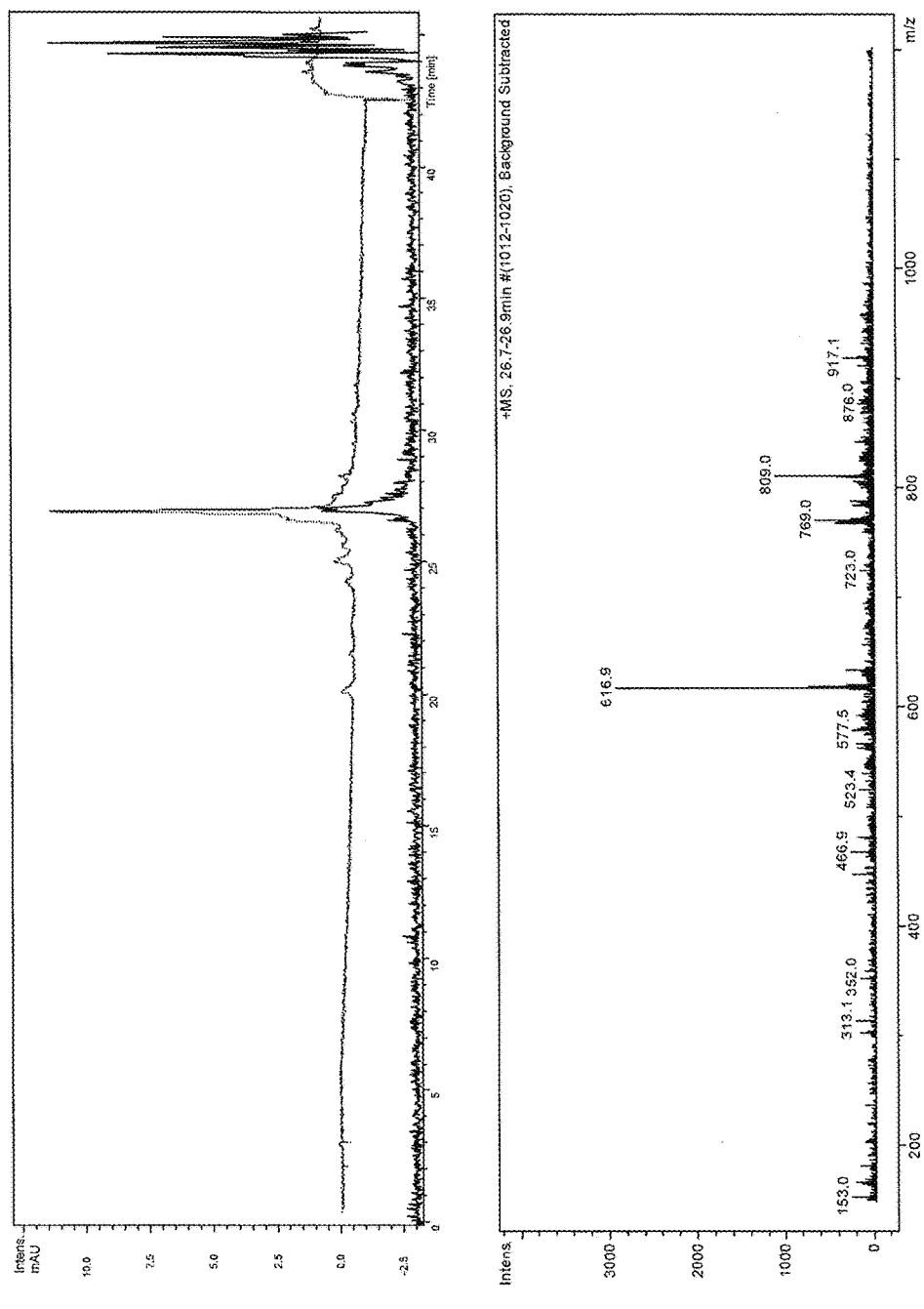
FIG. 9 depicts the mass spectrum of Compound A.

One aspect of the invention relates to a compound, or a pharmaceutically acceptable salt, biologically active metabolite, solvate, hydrate, prodrug, enantiomer or stereoisomer thereof, which generates the spectra in FIGS. 8 and 9.

Figure 10:
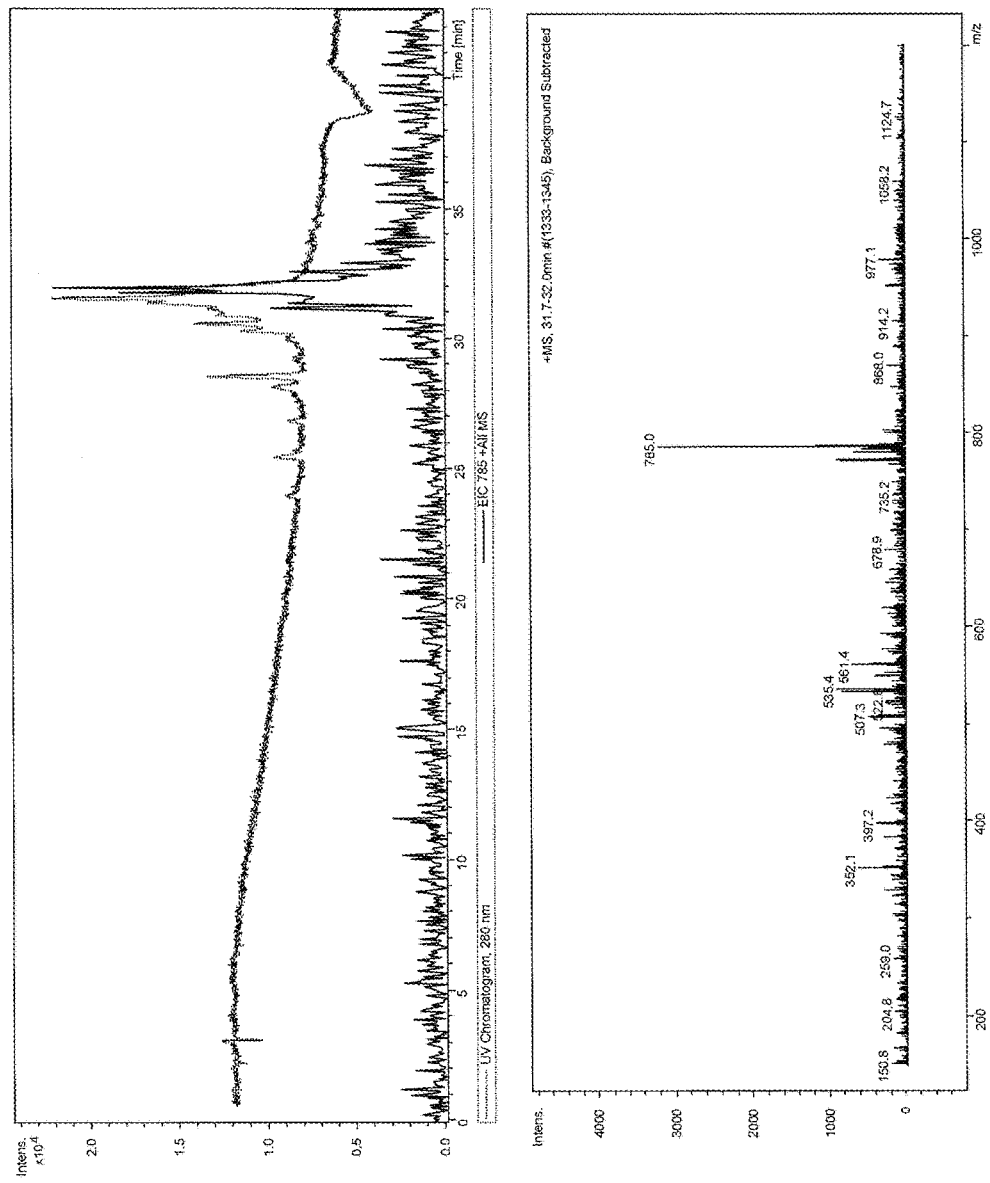
FIG. 10 depicts the mass spectrum of Pedunculagin.

One aspect of the invention relates to a compound, or a pharmaceutically acceptable salt, biologically active metabolite, solvate, hydrate, prodrug, enantiomer or stereoisomer thereof, which generates the spectrum in FIG. 10.

In certain embodiments, the present invention relates to any of the aforementioned compounds, wherein said compound, or a pharmaceutically acceptable salt, biologically active metabolite, solvate, hydrate, prodrug, enantiomer or stereoisomer thereof, was prepared by extraction from a plant material, as described herein. For example, one aspect of the invention relates to a compound prepared by a process comprising the steps of using an adsorbent to bind said compound; and eluting the bound compound from the adsorbent.

Isolation/Preparation

As noted above, extracts enriched in one or more compounds of the invention may be recovered from plant material, which plant material may include fruit, husks, juice, leaves, woody stems, and the like. Plants suitable for extraction include *Punica granatum*. Methods of purification are described in US Patent Application Publication No. US 2008/0318877 to Seeram et al., which is hereby incorporated by reference in its entirety.

A suspension of material from the plant material may be prepared by a variety of methods as known in the art, e.g., blending and aqueous extraction. The plant material may be subjected to enzymatic treatment including but not limited to extractase, pectinase and the like. The aqueous solution comprising compounds of the invention is applied to a polymeric adsorbent column, which is then washed with an aqueous buffer to remove unbound material. The compounds of interest bind to the resin, and may be eluted with a polar solvent, e.g., water, ethanol, methanol, and acetone.

The resin has a surface to which the compounds are adsorbed. A class of adsorptive resins are polymeric crosslinked resins composed of styrene and divinylbenzene such as, for example, the AMBERLITE series of resins, e.g., AMBERLITE XAD-16, which are available commercially from Rohm & Haas Co., Philadelphia, Pa. Other polymeric crosslinked styrene and divinylbenzene adsorptive resins suitable for use according to the invention are XFS-4257, XFS-4022, XUS-40323 and XUS-40322, all manufactured by The Dow Chemical Company, Midland, Mich.

One may use commercially available, FDA-approved, styrene-divinyl-benzene (SDVB) cross-linked copolymer resin, (e.g., AMBERLITE XAD-16, as described in U.S. Pat. No. 4,297,220, herein incorporated by reference). This resin is a non-ionic hydrophobic, cross-linked polystyrene divinyl benzene adsorbent resin. AMBERLITE XAD-16 has a macroreticular structure, with both a continuous polymer phase and a continuous pore phase. In certain embodiments, the resin used in the present invention has a particle size ranging from 100-200 microns.

Other adsorbents, such as those in the AMBERLITE XAD adsorbent series which contain hydrophobic macroreticular resin beads, with particle sizes in the range of 100-200 microns, may also be effective in the methods of the present invention. Moreover, different variations of the AMBERLITES, such as the AMERCHROM CG series of adsorbents, used with particle sizes in the range of 100-200 microns, may also be suitable for use in the present invention.

The resins are washed, e.g., with water or an aqueous buffer to remove unbound material from the extract. A solvent can be used to remove the adsorbed compounds, such as ethyl acetate or butanol.

The eluted compounds are substantially purified relative to the starting material, and may be further purified, e.g., by chromatography, etc., or may be directly used in formulations of interest. The final composition may be enriched, filtered, dialyzed, etc., using methods known in the art.

In certain embodiments, the present invention provides a compound of the invention, or a pharmaceutically acceptable salt, biologically active metabolite, solvate, hydrate, prodrug, enantiomer or stereoisomer thereof, substantially free of other compounds found in the plant material from which it is extracted. As used herein, the term "substantially free" means that the compound is made up of a significantly greater proportion of a compound of the invention, or a pharmaceutically acceptable salt, biologically active metabolite, solvate, hydrate, prodrug, enantiomer or stereoisomer thereof, as compared with the compound as found in the plant material from which it is extracted or extracts thereof.

In some embodiments, the present invention provides a compound of the invention, or a pharmaceutically acceptable salt, biologically active metabolite, solvate, hydrate, prodrug, enantiomer or stereoisomer thereof, in an amount of about 1 weight percent to about 99 weight percent.

In certain embodiments, the compound of the invention is provided in greater than about 2% chemical purity. In certain embodiments, the compound of the invention is provided in greater than about 10% chemical purity. In certain embodiments, the compound of the invention is provided in greater than about 20% chemical purity. In certain embodiments, the compound of the invention is provided in greater than about 30% chemical purity. In certain embodiments, the compound of the invention is provided in greater than about 40% chemical purity. In certain embodiments, the compound of the invention is provided in greater than about 50% chemical purity. In certain embodiments, the compound of the invention is provided in greater than about 75% chemical purity. In certain embodiments, the compound of the invention is provided in greater than about 80% chemical purity. In certain embodiments, the compound of the invention is provided in greater than about 85% chemical purity. In certain embodiments, the compound of the invention is provided in greater than about 90% chemical purity.

In certain embodiments, the compound of the invention is provided at between about 2% chemical purity and 10% chemical purity. In certain embodiments, the compound of the invention is provided at between about 10% chemical purity and 30% chemical purity. In certain embodiments, the compound of the invention is provided at between about 20% chemical purity and about 40% chemical purity. In certain embodiments, the compound of the invention is provided at between about 30% chemical purity and about 50% chemical purity. In certain embodiments, the compound of the invention is provided at between about 40% chemical purity and about 60% chemical purity. In certain embodiments, the compound of the invention is provided at between about 50% chemical purity and about 70% chemical purity. In certain embodiments, the compound of the invention is provided at between about 75% chemical purity and 95% chemical purity.

In other embodiments, the compound of the invention, or a pharmaceutically acceptable salt, biologically active metabolite, solvate, hydrate, prodrug, enantiomer or stereoisomer thereof, contains no more than about 50 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 25 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 20 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 15 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 10 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 9 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 8 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 7 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 6 area percent HPLC of other components of the plant material from which it is extracted relative to the total area of the HPLC chromatogram. In other embodiments, the compound of the invention, or a pharmaceutically acceptable salt, biologically active metabolite, solvate, hydrate, prodrug, enantiomer or stereoisomer thereof, contains no more than about 5 area percent HPLC of other components of the plant material from which it is extracted relative to the total area of the HPLC chromatogram. In certain embodiments, said plant source is *Punica granatum*.

In addition, compounds of the present invention may be prepared by semi-synthetic processes starting from other compounds found in extracts. This may be accomplished either by chemical or biological transformation of an isolated compound or an extract fraction or mixture of compounds. Chemical transformation may be accomplished by, but not limited to, manipulation of temperature, pH, and/or treatment with various solvents. Biological transformation may be accomplished by, but not limited to, treatment of an isolated compound or an extract fraction or mixture of compounds with plant tissue, plant tissue extracts, other microbiological organisms or an isolated enzyme from any organism.

Extracts

One aspect of the present invention relates to an extract comprising an aforementioned compound or compounds, or pharmaceutically acceptable salts, biologically active metabolites, solvates, hydrates, prodrugs, enantiomers or stereoisomers thereof.

Another aspect of the present invention relates to an extract comprising between about 1% to about 10% of an aforementioned compound or compounds, or pharmaceutically acceptable salts, biologically active metabolites, solvates, hydrates, prodrugs, enantiomers or stereoisomers thereof.

Another aspect of the present invention relates to an extract comprising between about 10% to about 20% of an aforementioned compound or compounds, or pharmaceutically acceptable salts, biologically active metabolites, solvates, hydrates, prodrugs, enantiomers or stereoisomers thereof.

Another aspect of the present invention relates to an extract comprising between about 20% to about 30% of an aforementioned compound or compounds, or pharmaceutically acceptable salts, biologically active metabolites, solvates, hydrates, prodrugs, enantiomers or stereoisomers thereof.

Another aspect of the present invention relates to an extract or composition comprising between about 30% to about 40% of an aforementioned compound or compounds, or pharmaceutically acceptable salts, biologically active metabolites, solvates, hydrates, prodrugs, enantiomers or stereoisomers thereof.

Another aspect of the present invention relates to an extract or composition comprising between about 40% to about 50% of an aforementioned compound or compounds, or pharmaceutically acceptable salts, biologically active metabolites, solvates, hydrates, prodrugs, enantiomers or stereoisomers thereof.

Another aspect of the present invention relates to an extract or composition comprising between about 50% to about 60% of an aforementioned compound or compounds, or pharmaceutically acceptable salts, biologically active metabolites, solvates, hydrates, prodrugs, enantiomers or stereoisomers thereof.

Another aspect of the present invention relates to an extract or composition comprising between about 60% to about 70% of an aforementioned compound or compounds, or pharmaceutically acceptable salts, biologically active metabolites, solvates, hydrates, prodrugs, enantiomers or stereoisomers thereof.

Another aspect of the present invention relates to an extract or composition comprising between about 70% to about 80% of an aforementioned compound or compounds, or pharmaceutically acceptable salts, biologically active metabolites, solvates, hydrates, prodrugs, enantiomers or stereoisomers thereof.

Another aspect of the present invention relates to an extract or composition comprising between about 80% to about 90% of an aforementioned compound or compounds, or pharmaceutically acceptable salts, biologically active metabolites, solvates, hydrates, prodrugs, enantiomers or stereoisomers thereof.

Another aspect of the present invention relates to an extract or composition comprising between about 90% to about 95% of an aforementioned compound or compounds, or pharmaceutically acceptable salts, biologically active metabolites, solvates, hydrates, prodrugs, enantiomers or stereoisomers thereof.

Another aspect of the present invention relates to an extract or composition comprising between about 95% to about 99% of an aforementioned compound or compounds, or pharmaceutically acceptable salts, biologically active metabolites, solvates, hydrates, prodrugs, enantiomers or stereoisomers thereof.

In certain embodiments, said extract is a *Punica granatum* extract.

Compositions

The compounds and extracts of the invention may be used to formulate pharmaceuticals, nutraceuticals, botanical drugs, herbal medicines, food additive, functional foods, medical foods, nutrition products, cosmetics, beverages, and the like.

The compounds and/or extracts of the invention may be provided as a composition with a pharmaceutically acceptable carrier. Such dosage forms encompass physiologically acceptable carriers that are inherently non-toxic and non-therapeutic. Examples of such carriers include vegetable proteins, soy proteins, ion exchangers, soft gels, oils, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

In certain embodiments, the compounds and/or extracts may be formulated in such vehicles at a concentration of about 0.01 μg/mL to about 200 μg/mL. In certain embodiments, the compounds and/or extracts may be formulated in such vehicles at a concentration of about 1 μg/mL to about 250 μg/mL. In certain embodiments, the compounds and/or extracts may be formulated in such vehicles at a concentration of about 250 μg/mL to about 500 μg/mL. In certain embodiments, the compounds and/or extracts may be formulated in such vehicles at a concentration of about 500 μg/mL to about 750 μg/mL. In certain embodiments, the compounds and/or extracts may be formulated in such vehicles at a concentration of about 750 μg/mL to about 1 μg/mL. In certain embodiments, the compounds and/or extracts may be formulated in such vehicles at a concentration of about 1 μg/mL to about 25 μg/mL. T In certain embodiments, the compounds and/or extracts may be formulated in such vehicles at a concentration of about 25 μg/mL to about 50 μg/mL. In certain embodiments, the compounds and/or extracts may be formulated in such vehicles at a concentration of about 50 μg/mL to about 100 μg/mL. In certain embodiments, the compounds and/or extracts may be formulated in such vehicles at a concentration of about 100 μg/mL to about 125 μg/mL. In certain embodiments, the compounds and/or extracts may be formulated in such vehicles at a concentration of about 125 μg/mL to about 150 μg/mL. In certain embodiments, the compounds and/or extracts may be formulated in such vehicles at a concentration of about 150 μg/mL to about 175 mg/mL. In certain embodiments, the compounds and/or extracts may be formulated in such vehicles at a concentration of about 175 μg/mL to about 200 μg/mL.

In certain embodiments, compounds, compositions and/or extracts of the invention may be combined with herbal medicines. Herbal medicines of interest include, but not restricted to, active fractions from certain herbal preparations, such as nettles (*Urtica dioica*)-turmeric (*Curcuma longa*), tea; marine or terrestrial animal products, e.g., bioactive lipids from *Perna canaliculus*, or *Dromaius nova hollandiae*.

In certain embodiments, compounds, compositions and/or extracts of the invention may be formulated as botanical drugs. As used herein, a "botanical drug" is a product consists of vegetable materials, which may include plant materials, algae, macroscopic fungi, or combinations thereof, which is intended for use in the diagnosis, cure, mitigation, treatment or prevention of disease in humans. In certain embodiments, the botanical drug product may be available as (but not limited to) a solution (e.g., tea), powder, tablet, capsule, elixir, topical, or injection.

In certain embodiments, compounds, compositions and/or extracts of the invention may be formulated as nutraceuticals. Nutraceutical formulations of interest include foods for veterinary or human use, including health food bars, drinks and drink supplements, and the like. These foods are enhanced by the inclusion of a biologically active compound, composition and/or extract of the invention. For example, in the treatment of neurodegenerative diseases, such as Alzheimer's, the normal diet of a patient may be supplemented by a nutraceutical formulation taken on a regular basis. Such nutraceuticals may or may not contain calories.

The term nutraceutical composition as used herein include food product, foodstuff, dietary supplement, nutritional supplement or a supplement composition for a food product or a foodstuff Thus, in another embodiment the present invention relates to a nutraceutical wherein the nutraceutical is a food product, foodstuff, dietary supplement, nutritional supplement or a supplement composition for a food product or a foodstuff.

As used herein, the term food product refers to any food or feed suitable for consumption by humans or animals. The food product may be a prepared and packaged food (e.g., mayonnaise, salad dressing, bread, or cheese) or an animal feed (e.g., extruded and pelleted animal feed, coarse mixed feed or pet food composition). As used herein, the term foodstuff refers to any substance fit for human or animal consumption. Food products or foodstuffs are for example beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks, milk, milk replacements, and other dairy drinks such as for example yoghurt drinks, and diet drinks. In another embodiment food products or foodstuffs refer to solid or semi-solid foods comprising the composition according to the invention. These forms can include, but are not limited to baked goods such as bars, cakes, cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour). The term food products or foodstuffs also includes functional foods and prepared food products, the latter referring to any pre-packaged food approved for human consumption.

In certain embodiments, the nutraceutical formulation may further comprise curcumin or tea catechins, such as EGCG, L-theanines, and resveratrol. In certain embodiments, the nutraceutical formulation may comprise extracts of acai berry, blueberry, cranberry, blackberry, raspberry, elderberry, St-Johns Wort, *ginkgo biloba*, kava, cocoa, wine grapes, grape seeds extracts, soy extracts, soy phytoestrogens, or combinations thereof.

In certain embodiments, compounds, compositions and/or extracts of the invention may be formulated as dietary supplements. Dietary supplements of the present invention may be delivered in any suitable format. In certain embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard (shell) gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Exemplary carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food; e.g., enclosed in caps of food or beverage containers for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacin, niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide; L-tryptophan; nicotinic acid; nicotinamide; nicotinamide riboside; omega-3 fatty acid (such as DHA, EPA and ALA); anthocyanines; isoflavones; choline; UMP; soy phospholipids; phosphatidyl serine; S-adenosyl-methionine (SAM); acethyl-L-carnitine (ALCAR); magnesium salts; magnesium acetate; magnesium chloride; magnesium citrate; magnesium lactate; magnesium gluconante; and magnesium pidolate.

In other embodiments, the present invention provides nutritional supplements (e.g., energy bars or meal replacement bars or beverages) comprising a compound, composition and/or extract according to the invention. The nutritional supplement may serve as meal or snack replacement and generally provide nutrient calories. However, as noted above, supplements which do not contain calories may also be used. In certain embodiments, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and hydrolysates or mixtures thereof. Soy protein have an almost perfect PDCAA, Protein Digestibility Corrected Amino Acid Score (PDCAAS) and by this criterion soy protein is the nutritional equivalent of meat and eggs for human growth and health. These proteins have high biological value; that is, they have a high proportion of the essential amino acids. See Modern Nutrition in Health and Disease, eighth edition, Lea & Febiger, publishers, 1986, especially Volume 1, pages 30-32. The nutritional supplement can also contain other ingredients, such as one or a combination of other vitamins, minerals, antioxidants, fiber and other dietary supplements (e.g., protein, amino acids, choline, lecithin, omega-3 fatty acids, and others discussed herein). Selection of one or several of these ingredients is a matter of formulation, design, consumer preference and end-user. The amounts of these ingredients added to the dietary supplements of this invention are readily known to the skilled artisan. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; anthocyanins; nicotinamide riboside; magnesium salts; nicotinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

The nutritional supplement can be provided in a variety of forms, and by a variety of production methods. In one embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, for the processing or manufacture of a nutritional supplement.

Additionally, flavors, coloring agents, spices, nuts and the like may be incorporated into the formulations described herein. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil.

Emulsifiers may be added for stability of the formulations. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the formulations to extend product shelf life. For example, preservatives such as potassium sorbate, sodium sorbate, potassium benzoate, sodium benzoate or calcium disodium EDTA are used.

In addition to the carbohydrates described above, the formulations can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the formulations of the present invention to obtain an adequate amount of an essential nutrient, which is missing in some diets. The multi-vitamin and mineral supplement may also be useful for disease prevention and protection against nutritional losses and deficiencies due to lifestyle patterns.

The dosage and ratios of the compound(s) of the invention administered via a such formulations will, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can be determined by the expert in the field with normal trials, or with the usual considerations regarding the formulation of a nutraceutical composition.

In certain embodiments, the formulation comprises per serving an amount of 1 mg to 10,000 mg of the active ingredient(s), e.g., a compound or compounds of the invention. In certain embodiments, the formulation comprises per serving an amount of 1 mg to 2,500 mg of the active ingredient(s). In certain embodiments, the formulation comprises per serving an amount of 2500 mg to 5000 mg of the active ingredient(s). In certain embodiments, the formulation comprises per serving an amount of 5000 mg to 7500 mg of the active ingredient(s). In certain embodiments, the formulation comprises per serving an amount of 7500 mg to 10000 mg of the active ingredient(s).

For cosmetic formulations, the compounds, compositions and/or extracts of the invention may optionally comprise skin benefit materials. These include estradiol; progesterone; pregnanalone; coenzyme Q10; methylsolanomethane (MSM); copper peptide (copper extract); plankton extract (phytosome); glycolic acid; kojic acid; ascorbyl palmitate; all-trans-retinol; azaleic acid; salicylic acid; broparoestrol; estrone; adrostenedione; androstanediols; etc. The steroids will generally be present at a concentration of less than about 2% of the total by weight of the composition, while the other skin benefit materials may be present at higher levels, for example as much as about 10 to 15%.

The compounds, compositions and/or extracts of the invention may comprise a cosmetically acceptable vehicle to act as a dilutant, dispersant or carrier, so as to facilitate its distribution when the composition is applied to the skin. Vehicles other than or in addition to water can include liquid or solid emollients, solvents, humectants, thickeners and powders.

The cosmetically acceptable vehicle will usually constitute from 0.1%, or 5% to 99.9%, preferably from 25% to 80% by weight of the composition, and can, in the absence of other cosmetic adjuncts, constitute the balance of the composition.

In accordance with the present invention, a compound, composition and/or extract of the present invention may be prepared as pharmaceutical compositions, such as those which may be particularly useful for the treatment of neurodegenerative diseases. Such compositions comprise a compound of the present invention or a pharmaceutically acceptable salt, biologically active metabolite, solvate, hydrate, prodrug, enantiomer or stereoisomer thereof, and a pharmaceutically acceptable carrier and/or excipient.

The compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eye drops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject formulations may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and *acacia* or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and *acacia*), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or *acacia*; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using excipients such as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics®, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

In certain embodiments, the compositions are formulated as a tablet, pill capsule or other appropriate ingestible formulation, to provide a therapeutic dose in 10 ingestible formulations or fewer. In another example, a therapeutic dose is provided in 20, 15, 10, 5 or 3 ingestible formulations.

The compositions of the present invention may be in the form of a dispersible dry powder for pulmonary delivery. Dry powder compositions may be prepared by processes known in the art, such as lyophilization and jet milling, as disclosed in International Patent Publication No. WO 91/16038 and as disclosed in U.S. Pat. No. 6,921,527, both of which are incorporated by reference. The composition of the present invention may be placed within a suitable dosage receptacle in an amount sufficient to provide a subject with a unit dosage treatment. The dosage receptacle may be one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237; all four of the US patents cited in this sentence are incorporated herein by reference.

The terms "transdermal delivery system", "transdermal patch", or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for postmenopausal indications, and nicotine for smoking cessation. Patches suitable for use in the present invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

In certain embodiments, the pharmaceutical composition features any subject compound, and/or extract provided in an amount sufficient to treat Mild Cognitive Impairment, Alzheimer's disease, enhance long-term memory, short-term memory, declarative memory, procedural memory or cognitive processes such as attention, executive function, reaction time or learning in a patient by a statistically significant amount when assessed by a standardized performance test.

In certain embodiments, the pharmaceutical composition features one or more subject compound, and/or extract provided in an amount sufficient to enhance long-term memory in a patient by a statistically significant amount when assessed by one or more of a Rey Auditory and Verbal Learning Test (RAVLT), Cambridge Neuropsychological Test Automated Battery (CANTAB); a Children's Memory Scale (CMS); a Contextual Memory Test; a Continuous Recognition Memory Test (CMRT); a Denman Neuropsychology Memory Scale; a Fuld Object Memory Evaluation (FOME); a Graham-Kendall Memory for Designs Test; a Guild Memory Test; a Learning and Memory Battery (LAMB); a Memory Assessment Clinic Self-Rating Scale (MAC-S); a Memory Assessment Scales (MAS); a Randt Memory Test; a Recognition Memory Test (RMT); a Rivermead Behavioral Memory Test; a Russell's Version of the Wechsler Memory Scale (RWMS); a Test of Memory and Learning (TOMAL); a Vermont Memory Scale (VMS); a Wechsler Memory Scale; and a Wide Range Assessment of Memory and Learning (WRAML); First-Last Name Association (Youngjohn J. R., et al., Archives of Clinical Neuropsychology 6:287-300 (1991)); Name-Face Association; Wechsler Memory Scale-Revised; (Wechsler, D., Wechsler Memory Scale-Revised Manual, NY, N.Y., The Psychological Corp. (1987)); California Verbal Learning Test—Second Edition (Delis, D. C., et al., The Californian Verbal Learning Test, Second Edition, Adult Version, Manual, San Antonio, Tex.: The Psychological Corporation (2000)); Facial Recognition (delayed non-matching to sample); Cognitive Drug Research (CDR) Computerized Assessment Battery-Wesnes; Buschke's Selective Reminder Test (Buschke, H., et al., Neurology 24:1019-1025 (1974)); Telephone Dialing Test; and Brief Visuospatial Memory Test-Revised.

Kits

This invention also provides kits for conveniently and effectively implementing the methods of this invention. Such kits comprise any subject compound, composition and/or extract, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

For example, the present invention also provides for kits containing at least one dose of a subject compound, composition and/or extract, and often many doses, and other materials for a treatment regimen. For example, in one embodiment, a kit of the present invention contains sufficient subject composition for from five to thirty days and optionally equipment and supplies necessary to measure one or more indices relevant to the treatment regiment. In another embodiment, kits of the present invention contain all the materials and supplies, including subject compositions, for carrying out any methods of the present invention. In still another embodiment, kits of the present invention, as described above, additionally include instructions for the use and administration of the subject compositions.

In one embodiment, the invention is a pharmaceutical kit comprising one or more subject compound, composition and/or extract in an amount sufficient to enhance long-term memory in a patient, a pharmaceutically acceptable carrier, and instructions (written and/or pictorial) describing the use of the subject compound, composition and/or extract for enhancing memory.

Dosage

The dosage of any compound, composition and/or extract of the present invention will vary depending on the symptoms, age and body weight of the patient, the nature and severity of the disorder to be treated, the route of administration, and the form of the subject composition. Any of the subject formulations may be administered in a single dose or in divided doses. Effective dosages for the compositions of the present invention may be readily determined by techniques known to those of skill in the art or as taught herein. The dosage may be selected to assuage the disorder in a subject in such a way as to provide at least partial relief if not complete relief. The skilled artisan may identify this amount as provided herein as well as by using other methods known in the art.

A therapeutically effective amount (i.e., dose) of a compound of the present invention can be determined by methods known in the art. The therapeutically effective quantities will depend on the age and on the general physiological condition of the patient, the route of administration and the pharmaceutical formulation used. In certain embodiments, the therapeutic doses may be between about 10 mg/day and 10,000 mg/day, between about 100 mg/day and 2,500 mg/day, or between 250 mg to about 1,000 mg/day. In other embodiments, other ranges may be used, including, for example, 50-250 mg/day, 250-500 mg/day, and 500-750 mg/day. The amount of the compound required for prophylactic treatment, referred to as a prophylactically-effective dosage, is generally the same as described for therapeutic treatment.

In certain embodiments, a therapeutic low dose of a compound or composition of the invention is administered. In certain embodiments, the therapeutically effective dose is between about 50 mg/day to about 150 mg/day. In certain embodiments, the therapeutic dose is between about 10 mg/day and about 20 mg/day. In certain embodiments, the therapeutic dose is between about 20 mg/day and about 30 mg/day. In certain embodiments, the therapeutic dose is between about 30 mg/day and about 40 mg/day. In certain embodiments, the therapeutic dose is between about 40 mg/day and about 50 mg/day. In certain embodiments, the therapeutic dose is between about 50 mg/day and about 60 mg/day. In certain embodiments, the therapeutic dose is between about 60 mg/day and about 70 mg/day. In certain embodiments, the therapeutic dose is between about 70 mg/day and about 80 mg/day. In certain embodiments, the therapeutic dose is between about 80 mg/day and about 90 mg/day. In certain embodiments, the therapeutic dose is between about 90 mg/day and about 100 mg/day. In certain embodiments, the therapeutic dose is between about 100 mg/day and about 110 mg/day. In certain embodiments, the therapeutic dose is between about 110 mg/day and about 120 mg/day. In certain embodiments, the therapeutic dose is between about 120 mg/day and about 130 mg/day. In certain embodiments, the therapeutic dose is between about 130 mg/day and about 140 mg/day. In certain embodiments, the therapeutic dose is between about 140 mg/day and about 150 mg/day. Administration may be once a day, twice a day, or more often, and may be decreased during a maintenance phase of the treatment of a disease or disorder, e.g., once every second or third day instead of every day or twice a day. The dose and the administration frequency will depend on the clinical signs, which confirm maintenance of the remission phase, with the reduction or absence of at least one or more clinical signs of the acute phase known to the person skilled in the art.

An effective dose or amount, and any possible affects on the timing of administration of the formulation, may need to be identified for any particular composition of the present invention. This may be accomplished by routine experiment as described herein, using one or more groups of animals, or in human trials if appropriate. The effectiveness of any subject composition and method of treating may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like.

While the subject is being treated, his or her health may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these re-evaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies typically within a range of circulating concentrations that include the $ED_{50}$ with little or no toxicity. The dosage may vary within this range depending upon the dosage form employed and the route of administration utilized.

Methods of Use

Certain aspects of the invention relate treating a subject having an impairment in memory and/or cognition. The subject can have an impairment in memory consolidation (the process of storing new information in long term memory), an impairment in short term memory processes, an impairment in long-term memory, an impairment in declarative memory or an impairment in procedural memory. The subjects are treated with the compounds described herein to enhance, prevent and/or restore long-term memory function and performance, e.g., to improve the process of storing new information in long term memory in humans (memory consolidation) or to improve short term memory.

One aspect of the invention relates to a method, comprising the step of administering to a subject an amount of a pomegranate extract; wherein the extract contains an active fraction comprising at least one polyphenol; and the extract has been prepared by:

a juicing and manufacturing process, optionally followed by fractionalization by centrifugation and/or ultrafiltration, before being dried;

a juicing and manufacturing process, optionally followed by fractionalization by centrifugation and/or ultrafiltration, before being adsorbed into the polymeric chromatographic resin, washed with water, and eluted with a solvent; or a juicing and manufacturing process, optionally followed by fractionalization by centrifugation and/or ultrafiltration, before being adsorbed into the polymeric chromatographic resin, washed with water, eluted with a solvent, and subsequently dried.

In certain embodiments, the present invention relates to any one of the aforementioned methods, wherein the extract has been prepared by a juicing and manufacturing process, optionally followed by fractionalization by centrifugation and/or ultrafiltration, before being dried In certain embodiments, the present invention relates to any one of the aforementioned methods, wherein the extract has been prepared by a juicing and manufacturing process, optionally followed by fractionalization by centrifugation and/or ultrafiltration, before being adsorbed into the polymeric chromatographic resin, washed with water, and eluted with a solvent.

In certain embodiments, the present invention relates to any one of the aforementioned methods, wherein the extract has been prepared by a juicing and manufacturing process, optionally followed by fractionalization by centrifugation and/or ultrafiltration, before being adsorbed into the polymeric chromatographic resin, washed with water, eluted with a solvent, and subsequently dried.

In certain embodiments, the present invention relates to any one of the aforementioned methods, wherein the extract is dried by spray drying.

In certain embodiments, the present invention relates to any one of the aforementioned methods, wherein the extract is dried under vacuum (e.g. 40° C. at 50 mbar).

In certain embodiments, the present invention relates to any one of the aforementioned methods, wherein the extract is fractionalized by cetrifugation.

In certain embodiments, the present invention relates to any one of the aforementioned methods, wherein the extract is fractionalized by ultrafiltration.

In certain embodiments, the present invention relates to any one of the aforementioned methods, wherein the solvent is an alcohol (e.g. ethanol).

In certain embodiments, the present invention relates to any one of the aforementioned methods, wherein the resin is a polyvynil-styrene divinyl benzene resin. In certain embodiments, concentration on such resins can be achieved via an adsorption in water at normal pressure or under vacuum, followed by extensive washing with water to remove highly polar constituents like sugars, fibers, and minerals. Sugar elution during the washing steps is followed with a standard refractometer and measured as Brix contant. Elution is then initiated by changing the buffer to more polar solvent like ethanol, methanol or mix of ethanol in water. In addition, in some embodiments, whole molecule elution can be followed by UV detection at 205 nm for example. See, for example, the "Purification of Ellagitannins" section of U.S. Pat. No. 7,638,640, which is hereby incorporated by reference for said section and in its entirety.

In certain embodiments, the present invention relates to any one of the aforementioned methods, wherein the resin is Amberlite XAD-16 (Rohm & Haas).

Another aspect of the invention relates to a method, comprising the step of administering a compound of the invention to a subject.

In certain embodiments, the present invention relates to any one of the aforementioned methods, wherein the compound is pure and isolated.

In certain embodiments, the present invention relates to any one of the aforementioned methods, wherein the compound is administered as part of an extract.

In certain embodiments, the present invention relates to any one of the aforementioned methods, wherein the compound is adminstered as part of an extract; and the extract is substantially free of polyphenols other than the compound.

In certain embodiments, the present invention relates to any one of the aforementioned methods, wherein the compound is adminstered as part of an extract; and the molar ratio of the moles of compound to the total moles of polyphenols in the extract is greater than about 0.99. In certain embodiments, the present invention relates to any one of the aforementioned methods, wherein the compound is adminstered as part of an extract; and the molar ratio of the moles of compound to the total moles of polyphenols in the extract is greater than about 0.9. In certain embodiments, the present invention relates to any one of the aforementioned methods, wherein the compound is adminstered as part of an extract; and the molar ratio of the moles of compound to the total moles of polyphenols in the extract is greater than about 0.85. In certain embodiments, the present invention relates to any one of the aforementioned methods, wherein the compound is adminstered as part of an extract; and the molar ratio of the moles of compound to the total moles of polyphenols in the extract is greater than about 0.8. In certain embodiments, the present invention relates to any one of the aforementioned methods, wherein the compound is adminstered as part of an extract; and the molar ratio of the moles of compound to the total moles of polyphenols in the extract is greater than about 0.75.

In certain embodiments, the present invention relates to any one of the aforementioned methods, wherein the extract is whole fruit extract 1766.

In certain embodiments, the present invention relates to any one of the aforementioned methods, wherein the extract is husk extract 1767.

In certain embodiments, the present invention relates to any one of the aforementioned methods, wherein the extract is extract 31008.

In certain embodiments, the present invention relates to any one of the aforementioned methods, wherein the extract is extract 31008-L or 31008-H.

In certain embodiments, the present invention relates to any one of the aforementioned methods, wherein the extract is extract 61109.

In certain embodiments, the present invention relates to any one of the aforementioned methods, wherein the extract is extract 71109.

In certain embodiments, the present invention relates to any one of the aforementioned methods, wherein the extract is extract 1767-1.

In certain embodiments, the present invention relates to any one of the aforementioned methods, wherein the extract is extract 1767-2.

In certain embodiments, the present invention relates to any one of the aforementioned methods, wherein the extract is extract 1767-3.

In certain embodiments, the present invention relates to any one of the aforementioned methods, wherein the extract is extract 1767-4.

In certain embodiments, the present invention relates to any one of the aforementioned methods, wherein the extract is extract 1767-5.

In certain embodiments, the present invention relates to any one of the aforementioned methods, wherein the extract is extract 1767-6.

In certain embodiments, the present invention relates to any one of the aforementioned methods, wherein the compound is administered as part of a nutraceutical composition.

In certain embodiments, the present invention relates to any one of the aforementioned methods, wherein the compound is administered as part of a functional food or functional nutrition product.

In certain embodiments, the present invention relates to any one of the aforementioned methods, wherein the compound is administered as part of a medical food or medical nutrition product.

In certain embodiments, the present invention relates to any one of the aforementioned methods, wherein the compound is administered as part of a dietary supplement.

In certain embodiments, the present invention relates to any one of the aforementioned methods, wherein the compound is administered as part of a pharmaceutical composition.

In certain embodiments, the present invention relates to any one of the aforementioned methods, wherein the subject is a human.

In certain embodiments, the present invention relates to any one of the aforementioned methods, wherein said human is elderly.

In certain embodiments, the present invention relates to any one of the aforementioned methods, wherein said human is not elderly.

In certain embodiments, the present invention relates to any one of the aforementioned methods, wherein said human is less than 20 years old.

In certain embodiments, the present invention relates to any one of the aforementioned methods, wherein said human is between 20 and 40 years old.

In certain embodiments, the present invention relates to any one of the aforementioned methods, wherein said human is between 40 and 60 years old.

In certain embodiments, the present invention relates to any one of the aforementioned methods, wherein said human is between 60 and 80 years old.

In certain embodiments, the present invention relates to any one of the aforementioned methods, wherein said human is between 80 and 100 years old.

In certain embodiments, the present invention relates to any one of the aforementioned methods, wherein said human is between 100 and 120 years old.

In certain embodiments, the present invention relates to any one of the aforementioned methods, wherein said human is healthy.

In certain embodiments, the present invention relates to any one of the aforementioned methods, wherein said human is not healthy.

In certain embodiments, the present invention relates to any one of the aforementioned methods, wherein the subject is a mammal.

In certain embodiments, the present invention relates to any one of the aforementioned methods, wherein the mammal is a veterinary animal.

In certain embodiments, the present invention relates to any one of the aforementioned methods, wherein the general cognition of the subject is improved.

In certain embodiments, the present invention relates to any one of the aforementioned methods, wherein the memory of the subject is improved.

In certain embodiments, the present invention relates to any one of the aforementioned methods, wherein the general cognition of the subject is maintained.

In certain embodiments, the present invention relates to any one of the aforementioned methods, wherein the memory of the subject is maintained.

In certain embodiments, the present invention relates to any one of the aforementioned methods, wherein a neuron or plurality of neurons in said subject are protected.

In certain embodiments, the present invention relates to any one of the aforementioned methods, wherein the subject's neurons are partially or substantially protected.

In certain embodiments, the present invention relates to any one of the aforementioned methods, wherein the method treats or prevents a neurodegenerative disorder.

In certain embodiments, the present invention relates to any one of the aforementioned methods, wherein the rate of the progression of said neurodegenerative disorder is decreased.

In certain embodiments, the present invention relates to any one of the aforementioned methods, wherein onset of said neurodegenerative disorder is delayed.

In certain embodiments, the present invention relates to any one of the aforementioned methods, wherein the method treats or prevents metabolic syndrome, type-II diabetes, dislipidemia, or obesity.

In certain embodiments, the present invention relates to any one of the aforementioned methods, wherein the method treats or prevents an amyloidosis-related condition in said subject.

In certain embodiments, the present invention relates to any one of the aforementioned methods, wherein the amyloidosis-related condition is MCI or AAMI.

In certain embodiments, the present invention relates to any one of the aforementioned methods, wherein the method treats or prevents ALS, Huntington's disease, Parkinson's disease, or Down syndrome.

In certain embodiments, the present invention relates to any one of the aforementioned methods, wherein the method treats or prevents Alzheimer's disease.

In certain embodiments, the present invention relates to any one of the aforementioned methods, wherein the method treats a memory impairment in a human.

In certain embodiments, the present invention relates to any one of the aforementioned methods, wherein the memory impairment results from one or more of age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, age-associated memory impairment, Mild Cognitive Impairment, attention deficit disorder, attention deficit hyperactivity disorder, Multiple Sclerosis, Anterior Communicating Artery Syndrome or AIDS-related dementia.

In certain embodiments, the present invention relates to any one of the aforementioned methods, wherein memory is improved in the human following said administration.

In certain embodiments, the present invention relates to any one of the aforementioned methods, wherein the improvement in memory is an improvement in at least one measure selected from the group consisting of an improvement in short-term memory, long-term memory, memory consolidation, procedural memory and declarative memory.

In certain embodiments, the present invention relates to any one of the aforementioned methods, wherein attention is improved in the human following said administration.

In certain embodiments, the present invention relates to any one of the aforementioned methods, wherein executive function is improved in the human following said administration.

In certain embodiments, the present invention relates to any one of the aforementioned methods, wherein reaction time is improved in the human following said administration.

In certain embodiments, the present invention relates to any one of the aforementioned methods, wherein learning is improved in the human following said administration.

A person skilled in the art will be able to envision subjects that can benefit from the methods described herein. For example, such subject includes peoples with suspected memory impairment of the Alzheimer's disease type, MCI, AAMI, Parkinson's disease, or ALS. Healthy elderly subject showing sign of cognitive impairment may also benefit from the compounds preventive affect of the present invention. One skilled in the art would recognize that the practitioner may apply different criteria for a determination of signs memory impairment. Such criteria include, but are not limited to Diagnostic and Statistical Manual of Mental Disorders, third edition (DSM-III) Alzheimer's Disease Diagnostic and Treatment Center (ADDTC), International Statistical Classification of Diseases, 10$^{th}$ Revision (ICD-IO), National Institute of Neurological Disorders and Stroke-Association Internationale pour la Recherche et Enseignment en Neurosciences (NINDS-AIREN) and Diagnostic and Statistical Manual of Mental Disorders, Fourth Edition (DSM-IV). See Pohjasvaara et al, *Stroke* 2000, 31, 2952-2957. Clinical characterization of a patient as mild cognitive impairment is well within the skill of the practitioner. Such testing of a patient to elucidate such a condition involves performing a series of mental tests. The methods for clinical diagnosis are widely reviewed and are discussed in, e.g., Petersen et al, *Arch. Neurol.* 1999, 56, 303-308.

In addition, there is growing evidence that type-II Diabetes is a risk factor for people to develop Alzheimer's disease; hence, people with predisposition to type-II Diabetes may benefit from a preventive therapy that would slow down progression of neurodegenerative disorders. Ho, L., W. Qin, et al. (2004). "Diet-induced insulin resistance promotes amyloidosis in a transgenic mouse model of Alzheimer's disease." *FASEB J* 18(7): 902-4; and Kojro, E. and R. Postina (2009). "Regulated Proteolysis of RAGE and AbetaPP as Possible Link Between Type 2 Diabetes Mellitus and Alzheimer's Disease." *J Alzheimers Dis* 16(4): 865-78.

Another aspect of the invention relates to a method of inhibiting aggregation of a peptide or protein, comprising the step of contacting the peptide or protein with an effective amount of a compound of the invention.

In certain embodiments, the present invention relates to any one of the aforementioned methods, wherein the compound is a compound of the invention, or pharmaceutically acceptable salt, biologically active metabolite, solvate, hydrate, prodrug, enantiomer or stereoisomer thereof.

In certain embodiments, the present invention relates to any one of the aforementioned methods, wherein the compound is pure and isolated.

In certain embodiments, the present invention relates to any one of the aforementioned methods, wherein the compound is in an extract.

Combination Therapy

In one aspect of the invention, a compound of the invention, or a pharmaceutically acceptable salt, biologically active metabolite, solvate, hydrate, prodrug, enantiomer or stereoisomer thereof, or an extract or composition containing the same, can be used alone or in combination with another therapeutic agent to treat diseases. It should be understood that the compounds of the invention can be used alone or in combination with an additional agent, e.g., a therapeutic agent, said additional agent being selected by the skilled artisan for its intended purpose. For example, the additional agent can be a therapeutic agent that is art-recognized as being useful to treat the disease or condition being treated by the compound of the present invention. The additional agent also can be an agent that imparts a beneficial attribute to the therapeutic composition e.g., an agent that affects the viscosity of the composition.

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

It should further be understood that the combinations included within the invention are those combinations useful for their intended purpose. The combination can also include more than one additional agent, e.g., two or three additional agents if the combination is such that the formed composition can perform its intended function. In some embodiments, the additional agent could be another compound of the invention, or a pharmaceutically acceptable salt, biologically active metabolite, solvate, hydrate, prodrug, enantiomer or stereoisomer thereof.

In certain embodiments, the compounds, compositions and/or extracts of the present invention may be administered at least once per day in combination with a prescribed drug. For example, the composition of the present invention may be administered together with existing anticholinesterase drugs now prescribed for Alzheimer's, with various antiinflammatory agents, or with statins. In certain embodiments the prescribed drug is a cholinesterase inhibitor. In certain embodiments the prescribed drug is selected from the group consisting of Namenda® (memantine), Reminyl® (galantamine), Exelon® (rivastigmine), Aricept® (donepezil), Cognex® (tacrine), Carbex® (selegiline) and Eldepryl® (selegiline).

In another aspect, the composition of the present invention is administered at least once per day in combination with a dietary or nutritional supplement believed to have beneficial health effects. Examples of dietary or nutritional supplements with which a compound, composition and/or extract may combined are below.

Coenzyme Q10 (also known as CoQ10, Q10, vitamin Q10, ubiquinone and ubidecarenone), a benzoquinone compound synthesized naturally by the human body, is used by cells of the body in oxidative metabolism or cell respiration and as an endogenous antioxidant. An "antioxidant" is a substance that at least partially protects cells from free radicals, which are highly reactive chemicals often containing oxygen atoms, that are capable of damaging important cellular components, such as DNA and lipids. The plasma level of CoQ10 has been used in studies as a measure of oxidative stress, a situation in which normal antioxidant levels are reduced. Various investigations have explored the usefulness of CoQ10 as a treatment for diseases, including, but not limited to, cancer and cardiovascular disease.

Idebenone, a synthetic analog of CoQ10, has been investigated in elderly patients with dementia. Studies suggest that it may diminish nerve cell damage due to ischemia and facilitate memory and learning.

Huperzine A, a natural acetylcholinesterase inhibitor derived from the Chinese herb *Huperzia serrata*, has antioxidant and neuroprotective properties, and has been proposed as a disease-modifying treatment for AD.

Galantamine, an acetylcholinesterase inhibitor, is used to treat symptoms of AD.

Vincamine and vinpocetine, a semisynthetic derivative of vincamine, an alkaloid derived from the plant Vina minor L, are used in Europe, Japan and Mexico as pharmaceutical agents for the treatment of cerebrovascular and cognitive disorders.

Acetyl-L-carinitine, an acetylated derivative of carnitine, has been shown to promote fatty acid beta-oxidation in liver and to prevent motor nerve condition velocity slowing in diabetic rats.

Dehydroepiandrosterone (DHEA), a steroid, is being studied in the prevention of cancer. In the body, it is a precursor produced by the adrenal gland and converted to testosterone or the estrogens.

Phosphatidylcholine, a phospholipid that is a major component of cell membranes, has putative activity as a cognition enhancer and in cell-membrane repair Gingko, an herb, has putative properties as a neuroprotective agent, an antioxidant, a free-radical scavenger, a membrane stabilizer, and an inhibitor of platelet-activating factor. Sherpina, V. S., et al., *American Family Physician* 68(5) 923-926 (2003). Gingko extract also has been shown to inhibit beta-amyloid deposition. Id.

Circumin, an active ingredient in turmeric, which is in curry, purportedly has antiinflammatory and cholesterol-lowering properties.

Berberine, which is a quaternary ammonium salt from the group of isoquinoline alkaloids. It is found in such plants as *Berberis*, goldenseal (*Hydrastis canadensis*), and *Coptis chinensis*, usually in the roots, rhizomes, stems, and bark. As a traditional medicine or dietary supplement, berberine has showed some activity against fungal infections, *Candida albicans*, yeast, parasites, and bacterial/viral infections.

*Ginseng*, a Chinese herb, has been used for centuries in Asia as a cure for many maladies.

Research has shown that Vitamin E (DL-alpha-tocopherol), an essential vitamin that functions as an antioxidant, can help prevent cardiovascular disease and increase the immune response. It has been hypothesized that Vitamin E and its analogs and derivatives may prevent brain cell damage by destroying toxic free radicals. The term "tocol" generally refers to 2-methyl-2-(4,8,12-trimetyltridecyl)chroman-6-ol; the term "tocopherol" generally refers to all mono, di, and trimethyltocols, including, but not limited to, alpha-tocopherol (5,7,8-trimethyltocol), beta-tocopherol (5,8-dimethyltocol), gamma-tocopherol (7,8-dimethyltocol), delta-tocopherol (8-methyltocol), the term "tocotrienol" refers to 2-methyl-2-(4,8,12-trimethyltrideca-3,7,11-trienyl)chroman-6-ol; and the term "vitamin E" generally refers to all tocol and tocotrienol derivatives exhibiting qualitatively the biological activity of alpha-tocopherol.

It is well-known that N-acetyl-cysteine (NAC) promotes cellular glutathione production, and thus reduces, or even prevents, oxidant mediated damage. Treatment with NAC provides beneficial effects in a number of respiratory, cardiovascular, endocrine, infectious, and other disease settings.

B vitamins, such as folic acid, are known to reduce levels of homocysteine, an amino acid already linked, at high levels, to an increased risk of heart attacks, strokes and Alzheimer's disease.

Lecithin, a lipid material composed of choline and inositol, is a major component of cell membranes. As used by producers of lecithin for commercial use, the term "lecithin" refers to a complex mix of phosphatides and other substances that contain phosphatidylcholine.

Choline (trimethyl ethanolamine), a quaternary saturated amine classified as an essential nutrient by the Food and Nutrition Board of the Institute of Medicine, is a component of lecithin. Choline is needed by the body to make the neurotransmitter acetylcholine.

Omega-3 fatty acids are a family of unsaturated fatty acids that have in common a final carbon-carbon double bond in the n-3 position; that is, the third bond from the methyl end of the fatty acid. Nutritionally important n-3 fatty acids include α-linolenic acid (ALA), eicosapentaenoic acid (EPA), and docosahexaenoic acid (DHA), all of which are polyunsaturated. Some experts believe these compounds can help regulate cholesterol in the body. They may also help protect the brain from cognitive problems associated with Alzheimer's disease.

Omega 6-fatty acids are a family of unsaturated fatty acids that have in common a final carbon-carbon double bond in the n-6 position, that is, the sixth bond, counting from the end opposite the carboxyl group. The biological effects of the n-6 fatty acids are largely mediated by their conversion to n-6 eicosanoids that bind to diverse receptors found in every tissue of the body. The conversion of tissue arachidonic acid (20:4n-6) to n-6 prostaglandin and n-6 leukotriene hormones provides many targets for pharmaceutical drug development and treatment to diminish excessive n-6 actions in atherosclerosis, asthma, arthritis, vascular disease, thrombosis, immune-inflammatory processes, and tumor proliferation. Competitive interactions with the n-3 fatty acids affect the relative storage, mobilization, conversion and action of the n-3 and n-6 eicosanoid precursors.

Deprenyl (selegiline, Eldepryl®), a monoamine oxidase inhibitor, is prescribed for the treatment of early-stage Parkinson's disease and senile dementia.

The formulations of the invention can be used alone or in combination with other pharmaceuticals or herbals to prolong mental health, to maintain or enhance cognitive functioning or memory, or to preserve mental or physical well-being and health. The formulations can also be used to prevent or treat effects of a number of ailments, including, but not limited to, Alzheimer's disease; Parkinson's disease; heart disease; arthritis; age-related degeneration; functional impairments; diabetes; cancer; and other diseases having an impact on cognitive function.

The effectiveness of the compositions and methods of the present invention can be assayed by a variety of protocols. The effects of increasing cognitive function in a human subject can be determined by methods routine to those skilled in the art including, but not limited to, both paper and pencil, and computer tests. One of skill in the art can also directly measure PP2A methylation levels, tau protein phosphorylation levels, neurofibrillary tangle formation and neurodegeneration in animal models.

The combination therapy contemplated by the invention includes, for example, administration of a compound of the invention and additional agent(s) in a single formulation as well as administration of a compound of the invention and additional agent(s) in separate formulations. In other words, co-administration shall mean the administration of at least two agents to a subject so as to provide the beneficial effects of the combination of both agents. For example, the agents may be administered simultaneously or sequentially over a period of time.

It should further be understood that the combinations included within the invention are those combinations useful for their intended purpose. The combination can also include more than one additional agent, e.g., two or three additional agents if the combination is such that the formed composition can perform its intended function.

Exemplary Tests for Cognitive Function

There are a variety of tests for cognitive function, especially learning and memory testing (see, for example, United States Patent Application Publication No. 2010/0010097). Learning and/or memory tests include, for example, Inhibitory Avoidance Test (also referred to herein as "Passive Avoidance Test"), contextual fear conditioning, visual delay non-match to sample, spatial delay non-match to sample, visual discrimination, Barnes circular maze, Morris water maze, radial arm maze tests, Ray Auditory-Visual Learning Test, the Wechsler Logical Memory Test, and the Providence Recognition Memory Test.

An exemplary Inhibitory Avoidance Test utilizes an apparatus that consists of a lit chamber that can be separated from a dark chamber by a sliding door. At training, the animal is placed in the lit chamber for some period of time, and the door is opened. The animal moves to the dark chamber after a short delay—the step-through latency—which is recorded. Upon entry into the dark chamber, the door is shut closed and a foot shock is delivered. Retention of the experience is determined after various time intervals, e.g., 24 or 48 hours, by repeating the test and recording the latency. The protocol is one of many variants of the passive avoidance procedures (for review, see Rush (1988) Behav. Neural. Biol. 50:255).

An exemplary maze testing embodiment is the water maze working memory test. In general, the method utilizes an apparatus which consists of a circular water tank. The water in the tank is made cloudy by the addition of milk powder. A clear plexiglass platform, supported by a movable stand rest on the bottom of the tank, is submerged just below the water surface. Normally, a swimming rat cannot perceive the location of the platform but it may recall it from a previous experience and training, unless it suffers from some memory impairment. The time taken to locate the platform is measured and referred to as the latency. During the experiment, all orientational cues such as ceiling lights, etc., remain unchanged. Longer latencies are generally observed with rats with some impairment to their memory.

Another memory test includes the eyeblink conditioning test, which involves the administration of white noise or steady tone that precedes a mild air puff which stimulates the subject's eyeblink. With training the auditory cue is sufficient to stimulate the eyeblinking response. This response is impaired in the presence of memory deficiencies.

Still another memory test which can be used is fear conditioning, e.g., either "cued" and "contextual" fear conditioning. In one embodiment, a freeze monitor administers a sequence of stimuli (sounds, shock) and then records a series of latencies measuring the recovery from shock induced freezing of the animal.

Another memory test for the lesioned animals is a holeboard test, which utilizes a rotating holeboard apparatus containing (four) open holes arranged in a 4-corner configuration in the floor of the test enclosure. A mouse is trained to poke its head into a hole and retrieve a food reward from a "baited" hole which contains a reward on every trial. There is a food reward (e.g., Fruit Loops®) in every exposed hole which is made inaccessible by being placed under a screen. The screen allows the odor of the reward to emanate from the hole, but does not allow access to the reinforcer. When an individual hole is baited, a reward is placed on top of the screen, where it is accessible. The entire apparatus rests on a turntable so that it may be rotated easily to eliminate reliance on proximal (e.g., olfactory) cues. A start tube is placed in the center of the apparatus. The subject is released from the tube and allowed to explore for the baited ("correct") hole. The performance of the mouse in this assay is affected by memory impairment.

Another model for measuring memory impairment makes use of fornix-lesioned animals for testing the ability of compounds to modulate memory consolidation, as well as for side effects and toxicity. In general, the subject method utilizes an animal which has been manipulated to create at least partial disruption of fornix-mediated signalling to the hippocampus, the disruption affecting memory consolidation and learned behavior in the animal. The animal is conditioned with a learning or memory regimen which results in learned behavior in the mammal in the absence of the fornix lesion. Compounds are administered to the animal in order to assess their effects on memory consolidation. An increase in learned behavior, relative to the absence of the test agents, indicates that the administered combination enhances memory consolidation.

Another memory test especially developed for use in pharmaceutical studies is the Providence Recognition Memory Test. This test consists of one pictorial and one verbal assessment of long-term declarative memory. In each of the two modes, the patient views stimuli on a computer screen and is later asked to recognize those stimuli in a two-alternative forced-choice format. The pictorial assessment mode consists of two parts: a study phase and a recognition phase. In the study phase, patients view a series of 120 pictures, for 3 seconds each. They are told to look at the pictures and remember them, so that they can recognize them later. In the recognition phase, patients view pictures two at a time and are asked to indicate by button press which of the two pictures they saw in a study phase. Recognition memory testing occurs at ten minutes, one hour, and 24 hours after the end of the study phase. The verbal assessment mode consists of two parts: a study phase and a recognition phase. In the study phase, patients view a series of 60 sentences one at a time. They are asked to read the sentences aloud and remember them, so that they can recognize them later. Each sentence remains on the computer screen until the patient has finished reading it aloud. If patients read words incorrectly, the examiner supplies the correct word or words. In the recognition phase, patients view sentences two at a time and are asked to indicate by button press which of the two sentences they saw in the study phase. Recognition memory testing occurs at ten minutes, one hour, and 24 hours after the end of the study phase.

In the methods of the present invention, retention of the learned behavior can be determined, for example, after at least about 12-24 hours, 14-22 hours, 16-20 hours and or 18-19 hours after completion of the learning phase to determine whether the agents promote memory consolidation. In a particular embodiment, retention of the learned behavior can be determined 24 hours after completion of the learning phase.

In addition to models for studying memory consolidation, models to assess side effects of amphetamine compounds on behavior have been utilized including locomotor activity models. An exemplary locomotor activity test utilizes an apparatus that consists of photocell activity cages with a grid of photocell beams placed around the cage. The animals are placed in individual activity cages some period of time prior to administration of agents. Locomotor activity is measured by the number of interruptions of the photoelectric beam during a given period of time.

As used herein, a "control mammal" can be an untreated lesion mammal (i.e., a lesion animal receiving no agents or not the same combinations to be assessed), a trained control mammal (i.e., a mammal that undergoes training to demonstrate a learned behavior without any lesion) and/or an untrained control mammal (i.e., a mammal with or without a lesion, that receives no training to demonstrate a learned behavior).

Definitions

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

For purposes of this invention, the chemical elements are identified in accordance with the Periodic Table of the Elements, CAS version, Handbook of Chemistry and Physics, 67th Ed., 1986-87, inside cover.

As used here, the term "anti-aggregation compound" refers to a compound that exhibits anti-aggregation properties, i.e., inhibits the formation of protein or peptide soluble or insoluble aggregate in vitro and/or in vivo. For purpose of this definition, such effect can be quantified and tested in vitro as is known in the art, for example, as described in the examples in the following references, each of which are hereby incorporated by reference. Ono, K., Y. Yoshiike, et al. (2003). "Potent anti-amyloidogenic and fibril-destabilizing effects of polyphenols in vitro: implications for the prevention and therapeutics of Alzheimer's disease." *J Neurochem* 87(1): 172-81; Riviere, C., T. Richard, et al. (2007). "Inhibitory activity of stilbenes on Alzheimer's beta-amyloid fibrils in vitro." *Bioorg Med Chem* 15(2): 1160-7; and Riviere, C., T. Richard, et al. (2008). "New polyphenols active on beta-amyloid aggregation." *Bioorg Med Chem Lett* 18(2): 828-31.

"Treating" is used herein to refer to any treatment of, or prevention of, or inhibition of a disorder or disease in a subject and includes by way of example: (a) preventing the disease or disorder from occurring in a subject that may be predisposed to the disease or disorder, but has not yet been diagnosed as having it; (b) inhibiting the disease or disorder, i.e., arresting or delaying its progression; or (c) relieving or ameliorating the disease or disorder, i.e., causing regression.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "alkylene" is art-recognized, and as used herein pertains to a bidentate moiety obtained by removing two hydrogen atoms of an alkyl group, as defined above.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, mono-cyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyr-rolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluroralkylsulfonyl, alkenylsulfonyl, alkynylsulfonyl, alkoxysulfonyl, haloalkoxysulfonyl, fluroralkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, haloalkoxysulfinyl, fluroralkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluroralkylsulfonyloxy, alkenylsulfonyloxy, alkynylsulfonyloxy, haloalkoxysulfonyloxy, fluroralkoxysulfonyloxy, alkenyloxysulfonyloxy, alkynyloxysulfonyloxy, alkylsulfinyloxy, haloalkylsulfinyloxy, fluroralkylsulfinyloxy, alkenylsulfinyloxy, alkynylsulfinyloxy, alkoxysulfinyloxy, haloalkoxysulfinyloxy, fluroralkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "aryl," as used herein means a phenyl group, naphthyl or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluroralkylsulfonyl, alkenylsulfonyl, alkynylsulfonyl, alkoxysulfonyl, haloalkoxysulfonyl, fluroralkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, halo alkoxysulfinyl, fluroralkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluroralkylsulfonyloxy, alkenylsulfonyloxy, alkynylsulfonyloxy, haloalkoxysulfonyloxy, fluroralkoxysulfonyloxy, alkenyloxysulfonyloxy, alkynyloxysulfonyloxy, alkylsulfinyloxy, haloalkylsulfinyloxy, fluroralkylsulfinyloxy, alkenylsulfinyloxy, alkynylsulfinyloxy, alkoxysulfinyloxy, haloalkoxysulfinyloxy, fluroralkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the aryl group through a methylene, ethylene or propylene moiety.

The term "arylene," is art-recognized, and as used herein pertains to a bidentate moiety obtained by removing two hydrogen atoms from adjacent carbons of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluroralkylsulfonyl, alkenylsulfonyl, alkynylsulfonyl, alkoxysulfonyl, haloalkoxysulfonyl, fluroralkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, halo alkoxysulfinyl, fluroralkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluroralkylsulfonyloxy, alkenylsulfonyloxy, alkynylsulfonyloxy, haloalkoxysulfonyloxy, fluroralkoxysulfonyloxy, alkenyloxysulfonyloxy, alkynyloxysulfonyloxy, alkylsulfinyloxy, haloalkylsulfinyloxy, fluroralkylsulfinyloxy, alkenylsulfinyloxy, alkynylsulfinyloxy, alkoxysulfinyloxy, haloalkoxysulfinyloxy, fluroralkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g. methylene).

The term "heteroarylene," is art-recognized, and as used herein pertains to a bidentate moiety obtained by removing two hydrogen atoms from adjacent atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocycyloxy", and "heterocycyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkyenylthio", "alkynylthio", "carbocycylthio", and "heterocycylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluroralkylsulfonyl", "alkenylsulfonyl", "alkynylsulfonyl", "carbocycylsulfonyl", "heterocycylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluroralkoxysulfonyl", "alkenyloxysulfonyl", "alkynyloxysulfonyl", "carbocycyloxysulfonyl", "heterocycyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(═O)— group. Sulfinyl groups are as defined above for sulfonyl groups. The term "sulfinic acid" as used herein refers to —S(═O)OH.

The term "oxy" refers to a —O— group.

The term "carbonyl" as used herein means a —C(═O)— group.

The term "thiocarbonyl" as used herein means a —C(═S)— group.

The term "formyl" as used herein means a —C(═O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocycylcarbonyl", "heterocycylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocycyloxycarbonyl", "heterocycyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocycylcarbonyloxy", "heterocycylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluroralkylsulfonyloxy", "alkenylsulfonyloxy", "alkynylsulfonyloxy", "carbocycylsulfonyloxy", "heterocycylsulfonyloxy", "arylsulfonyloxy", "aralkylsulfonyloxy", "heteroarylsulfonyloxy", "heteroaralkylsulfonyloxy", "haloalkoxysulfonyloxy", "fluroralkoxysulfonyloxy", "alkenyloxysulfonyloxy", "alkynyloxysulfonyloxy", "carbocycyloxysulfonyloxy", "heterocycyloxysulfonyloxy", "aryloxysulfonyloxy", "aralkyloxysulfonyloxy", "heteroaryloxysulfonyloxy" and "heteroaralkyloxysulfonyloxy" are examples of thereof.

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocycyl, heterocycyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocycylcarbonyl, heterocycylcarbonyl, arylcarbonyl, aralkylcarbonyl, heteroarylcarnbonyl, heteroaralkylcarbonyl and the sufonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" as used herein means a —N$_3$ group.

The term "phosphinyl" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocycyl, heterocycyl, aryl, aralkyl, heteroaryl, heteroaralkyl, alkoxy, haloalkoxy, fluoroalkyloxy, alkenyloxy, alkynyloxy, carbocycyloxy, heterocycyloxy, aryloxy, aralkyloxy, heteroaryloxy, heteroaralkyloxy, and amino.

The term "phosphoryl" as used herein refers to —P(═O) OH$_2$ and substituted derivatives thereof wherein one or both of the hydroxyls are independently replaced with substituents selected from the group consisting of alkyl, haloalkyl, fluoroalkyl, alkenyl, alkynyl, carbocycyl, heterocycyl, aryl, aralkyl, heteroaryl, heteroaralkyl, alkoxy, haloalkoxy, fluoroalkyloxy, alkenyloxy, alkynyloxy, carbocycyloxy, heterocycyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocycyl, heterocycyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a say' group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

As used herein, a "carbohydrate" (or, equivalently, a "sugar") is a saccharide (including monosaccharides, oligosaccharides and polysaccharides) and/or a molecule (including oligomers or polymers) derived from one or more monosaccharides, e.g., by reduction of carbonyl groups, by oxidation of one or more terminal groups to carboxylic acids, by replacement of one or more hydroxy group(s) by a hydrogen atom, an amino group, a thiol group or similar heteroatomic groups, etc. The term "carbohydrate" also includes derivatives of these compounds. In some cases, the carbohydrate may be a pentose (i.e., having 5 carbons) or a hexose (i.e., having 6 carbons); and in certain instances, the carbohydrate may be an oligosaccharide comprising pentose and/or hexose units, e.g., including those described above.

"Carbohydrate" and "sugar" as used herein also includes sugar-mimetics and sugar-like moieties. Sugar-mimetics are well known to one of ordinary skill in the art and include those described in detail in "Essentials of Glycobiology" Edited by Varki, A., et al, Cold Spring Harbor Laboratory Press. Cold Spring Harbor, N. Y. 2002. For example, sugar-mimetic groups contemplated by the present invention include cyclitols, such as a cycloalkane containing one hydroxyl group on each of three or more ring atoms, as defined by IUPAC convention. In other embodiments, such cyclitol moieties include inositols such as scyllo-inositol. Suitable sugar-like moieties include acyclic sugar groups. Such groups include linear alkytols and erythritols, to name but a few. It will be appreciated that sugar groups can exist in either cyclic or acyclic form. Accordingly, acyclic forms of a sugar group are contemplated by the present invention as a suitable sugar-like moieties.

The term "gallic acid equivalents" is a well-known term of art, referring to the use of gallic acid as a standard for quantification of the phenol content of various analytes by the Folin-Ciocalteau assay.

The term "extract" or "botanical extract" as used herein refers to a product prepared by separating, by chemical or physical process, medicinally active portions of a plan from the inactive or inert components.

As used herein, the term "cognitive function" refers to the ability to perform mental tasks, such as thinking, learning, judging, remembering, computing, controlling motor functions, and the like. The expression "resilience of cognitive function" refers to the ability of functional elements of cognitive function to resist deterioration over time.

As used herein, the terms "therapeutically effective amount," "memory-enhancing amount", and "cognition enhancing amount" are used interchangeably to refer to the amount of the composition of the invention that results in a therapeutic or beneficial effect, including a subject's perception of health or general well-being, following its administration to a subject.

In particular, "cognitive function enhancing amount" refers to that amount of the composition of the present invention that will noticeably impact the ability to perform mental tasks, as measured by tests for memory, computation, attention, or other mental or cognitive attribute, or as suggested by an individual's perception of his or her abilities in these realms.

The terms "dietary supplement" and "nutritional supplement" are used interchangeably herein to mean (1) a product intended to supplement the diet that bears or contains one or more of the following dietary ingredients: (A) a vitamin, (B) a mineral, (C) an herb or other botanical, (D) an amino acid, (E) a dietary substance for use by man to supplement the diet by increasing the total dietary intake; and/or (F) a concentrate, metabolite, constituent, extract, or combination of any ingredient described in clause (A), (B), (C), (D), or (E); and (2) a product that (A)(i) is intended for ingestion; (B) is not represented for use as a conventional food or as a sole item of a meal or the diet; and (C) is labeled as a dietary supplement.

The term "food" as used herein refers to (1) articles used for food or drink for man or other animals; (2) chewing gum; and (3) articles used for components of any such article. The term "functional food" or "functional nutrition product" refers to a food or nutrition product that is sold (e.g. in a supermarket or online) without any restrictions. The term "medical food" or "medical nutrition product" refers to a food or nutrition product with is prescribed by a physician. Foods or nutrition products may be solids, liquids, gels, powders or gases. Examples of solids are fruit-based drinks, coffee-based drinks, tea-based drinks, sport drinks, nutrition bars, snack foods, gums, cereals, candies, baby formulas, energy drinks, adult nutritional drinks, health drinks, and other food products. The term "sports drink" refers to a beverage that is supposed to rehydrate athletes, as well as restoring electrolytes, sugar and other nutrients, for example, Gatorade, POWERade, and AU Sport. As used herein, the term "energy drink" refers to a beverage, including, but not limited to, Jolt Cola, Red Bull and similar products, that contains legal stimulants, vitamins and minerals; these products are formulated to give the user a burst of energy. The term "adult nutritional drink" as used herein refers to such products as Ensure, Longetics® or a similar product. The term "health drink" refers to any beverage purported to have beneficial health effects, including, but not limited to, reducing inflammation; supporting the immune system; neutralizing infectious agents; preventing clogged arteries, preserving cognitive function and inhibiting cancer growth.

EXEMPLIFICATION

The invention will be more readily understood by reference to the following examples, which are included merely for purposes of illustration of certain aspects and embodiments of the present invention, and are not intended to limit the invention.

Example 1

Screening Assay for Pomegranate Compounds which Inhibit Aggregation of Aβ(25-35)

Monomeric Aβ(25-35) purchased from Bachem Pharma, was dissolved in distilled sterile water at 4° C., then sonitcated for about 1 minute. The peptide stock solution was then aliquoted and stored at −20° C. All steps were carried out at 4° C. to prevent Aβ(25-35) polymerization.

Fractions of polyphenols were all standardized to 10 µg/mL, before being assessed and stored at −20° C. Measurement of inhibition was performed by following the kinetic of Aβ(25-35) polymerization in a reaction mixture containing 70 µL phosphate buffer, 10 µL Thioflavin-T (100 µM stock solution), 10 µL MeOH (10 mM final concentration) pH 7.2 and 10 μL of Aβ(25-35) (100 μM final concentration) adapting known in the art procedures. LeVine, H., 3rd (1993). "Thioflavine T interaction with synthetic Alzheimer's disease beta-amyloid peptides: detection of amyloid aggregation in solution." *Protein Sci.* 2(3): 404-10. When Aβ(25-35) was added to the buffer solution, the solution was sonicated for an additional minute.

To study the inhibitory activity of the fractions, the extracts were diluted to the final concentration in MeOH and 10 μL was added to the mixture at 4° C. Fluorescence spectroscopy was recorded with the excitation at 450 nm and emission at 490 nm. The polymerization kinetics was monitored at 25° C. between 0 and 120 minutes. The $IC_{50}$ was calculated by using a least-square fitting technique to match the experimental data with a sigmoidal curve. The $IC_{50}$ was the effective concentration dose of the compound inhibiting the formation of Aβ fibrils to 50% of the control value.

Figure 11:
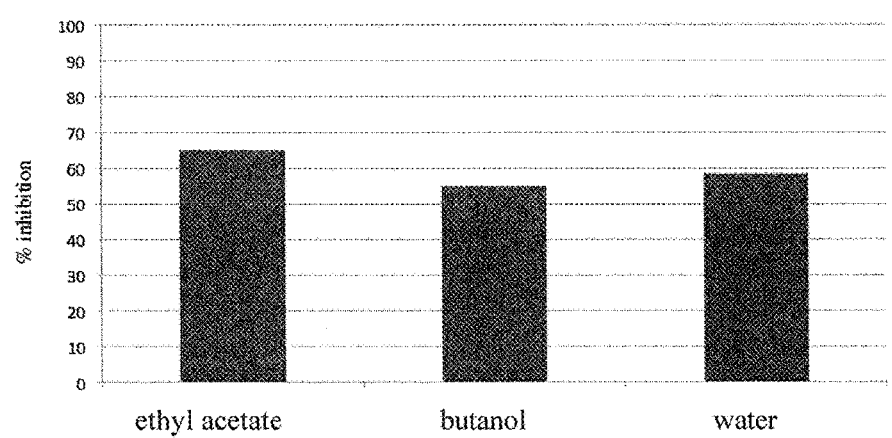
FIG. 11 depicts the results of the screening assays for inhibition of aggregation using $A\beta_{25-35}$ and ThT fluorescence with various fractions isolated using different extraction solvents.
Figure 13:
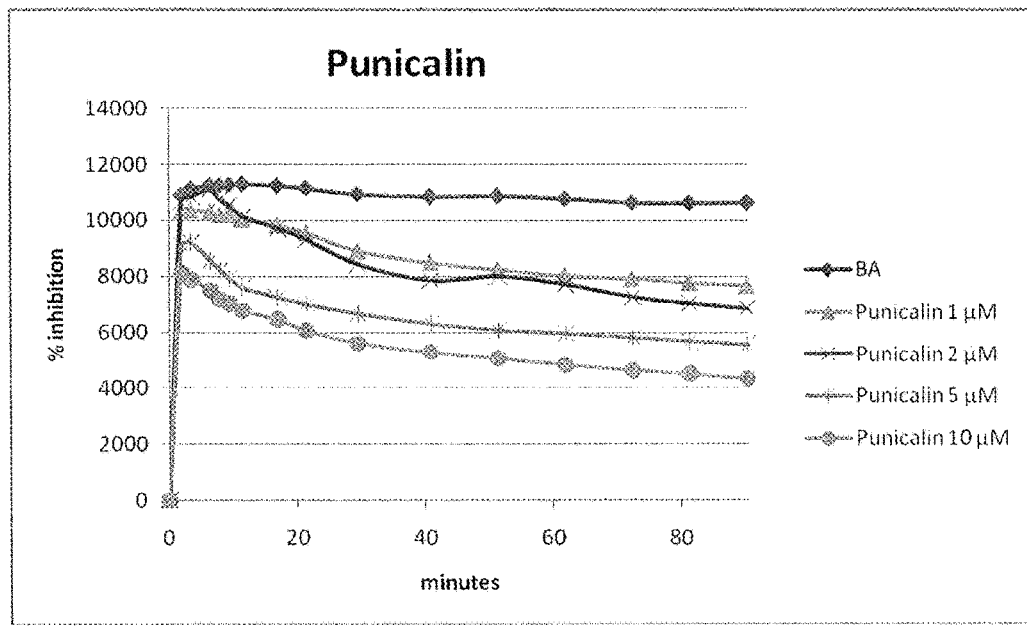
FIG. 13 depicts the results using Punicalin in dose-response fluorescence in vitro assays on $A\beta_{25-35}$.
Figure 13:
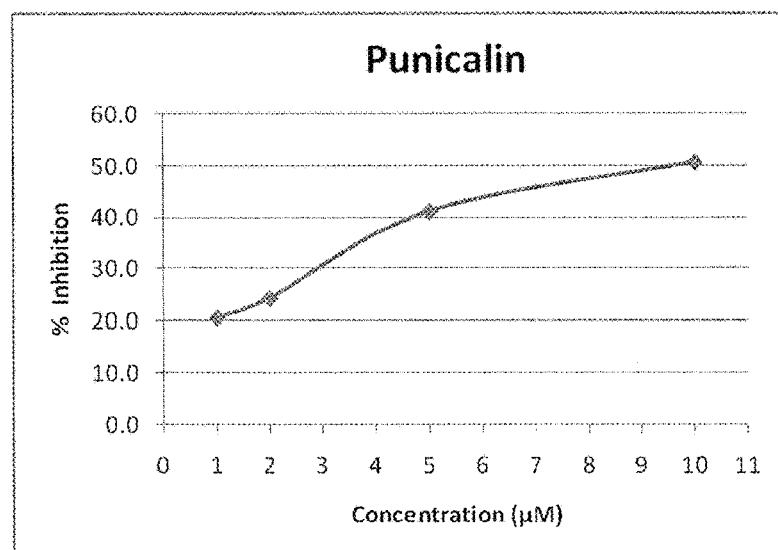
Figure 14:
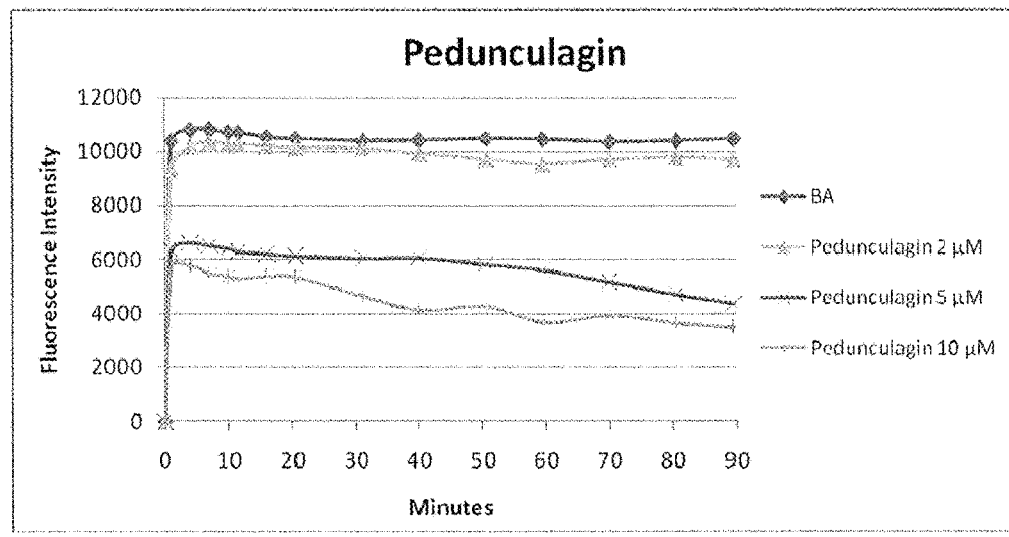
FIG. 14 depicts the results using Pedunculagin in dose-response fluorescence in vitro assays on $A\beta_{25-35}$.
Figure 14:
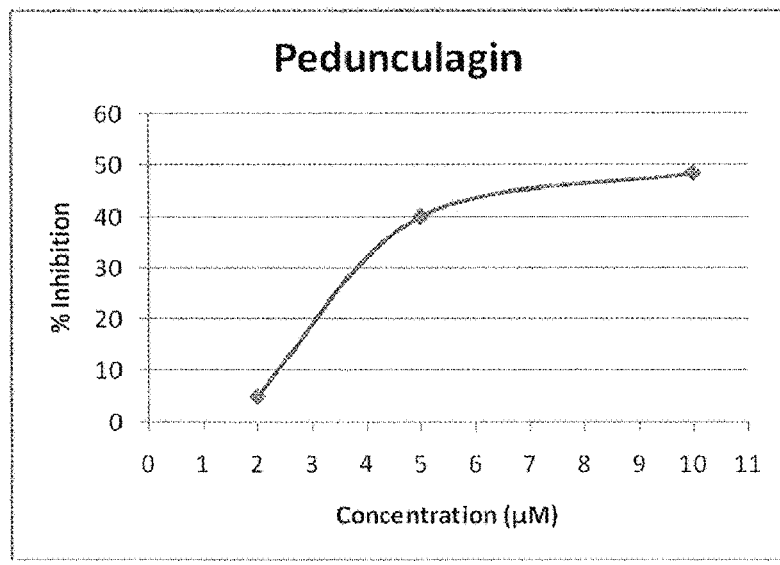
Figure 15:
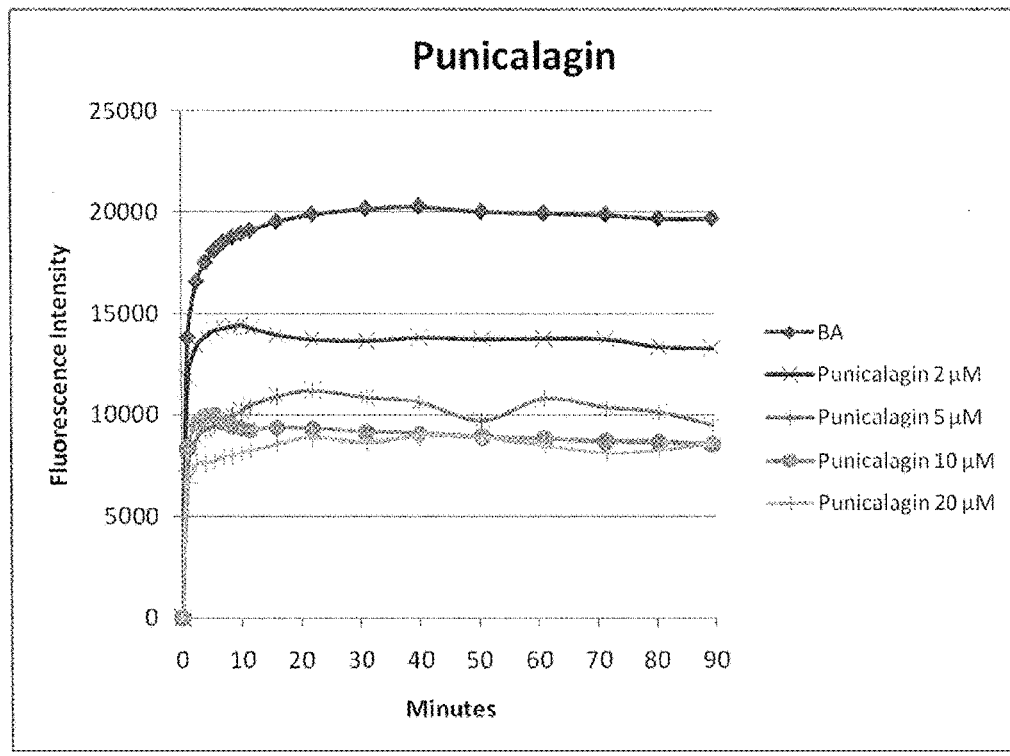
FIG. 15 depicts the results using Punicalagin in dose-response fluorescence in vitro assays on $A\beta_{25-35}$.
Figure 15:
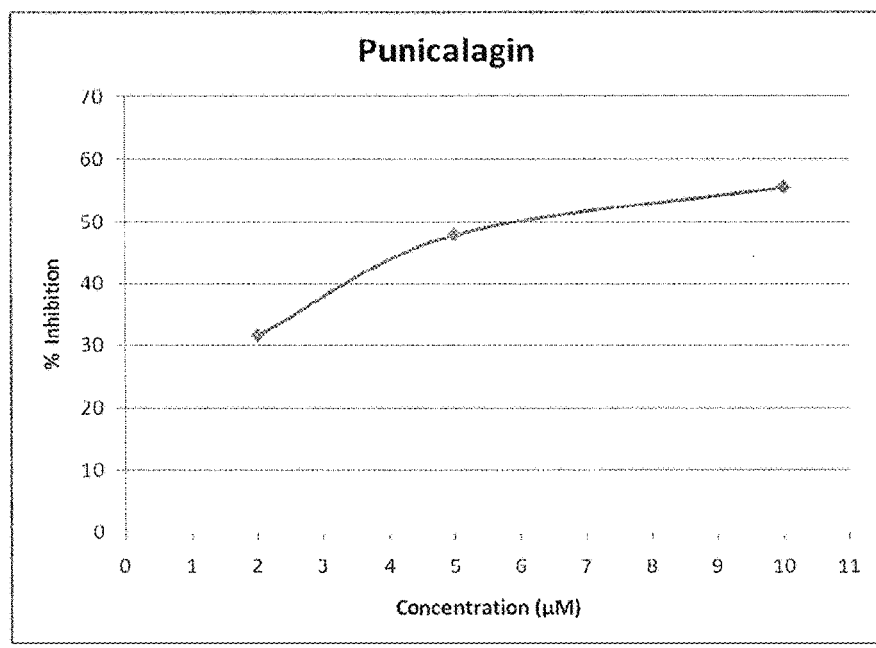
Figure 16:
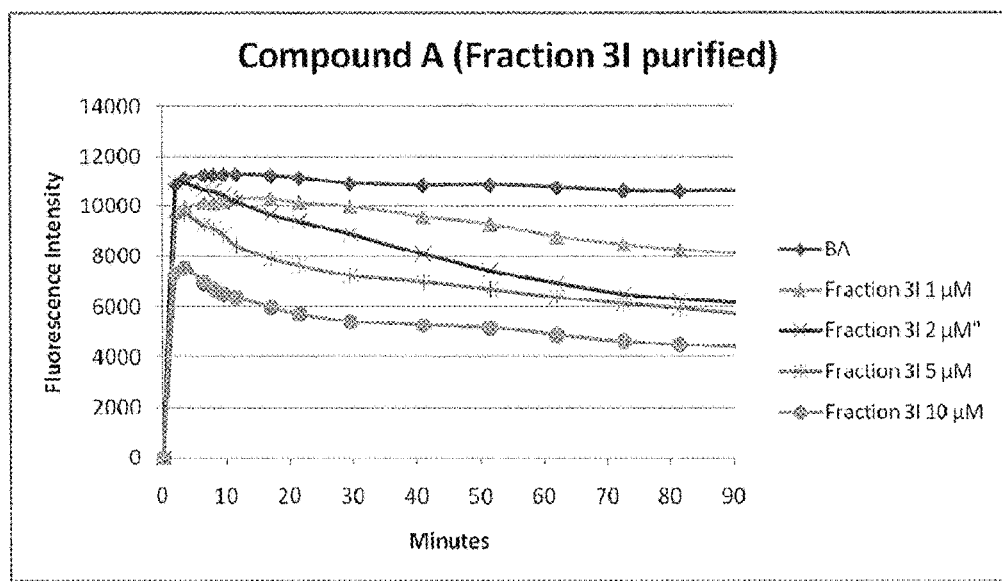
FIG. 16 depicts the results using Compound A (3I) in dose-response fluorescence in vitro assays on $A\beta_{25-35}$.
Figure 16:
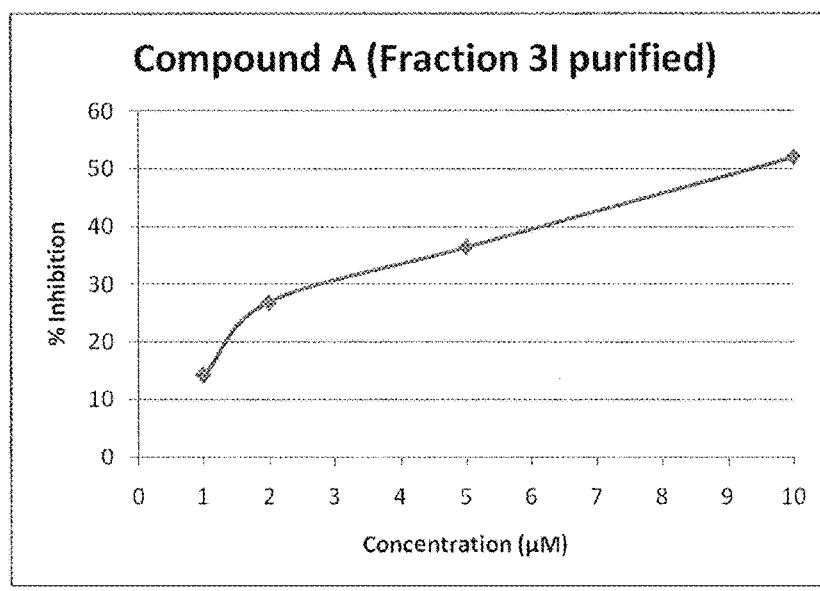
Figure 17:
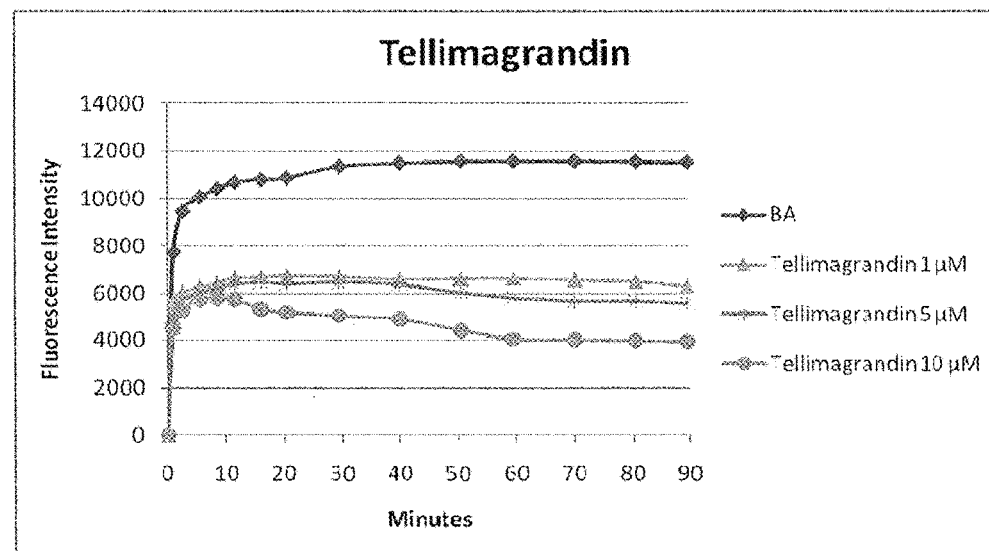
FIG. 17 depicts the results using Tellimagrandin in dose-response fluorescence in vitro assays on $A\beta_{25-35}$.
Figure 17:
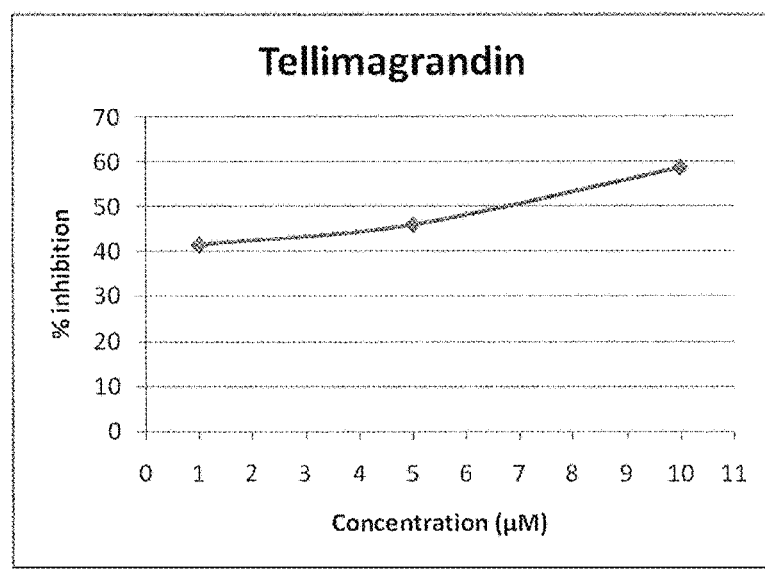
Figure 18:
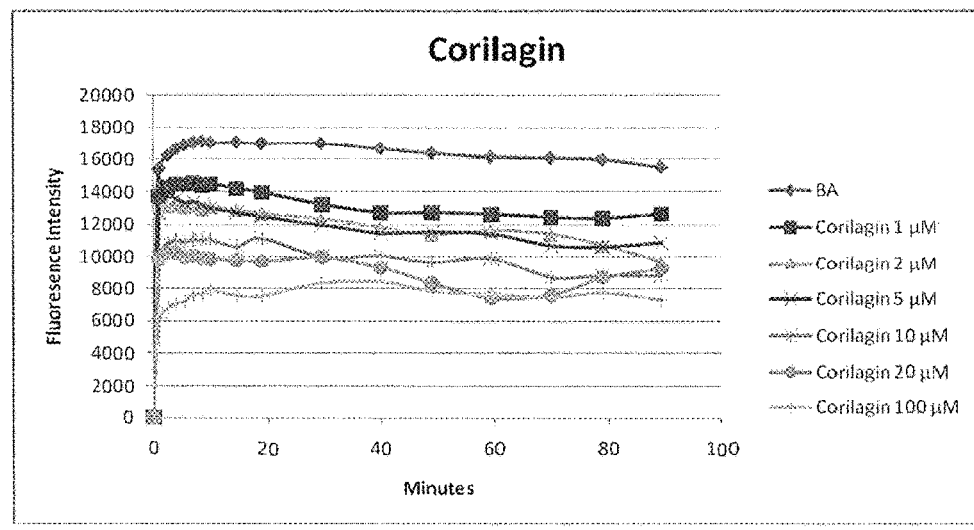
FIG. 18 depicts the results using Corilagin in dose-response fluorescence in vitro assays on $A\beta_{25-35}$.
Figure 18:
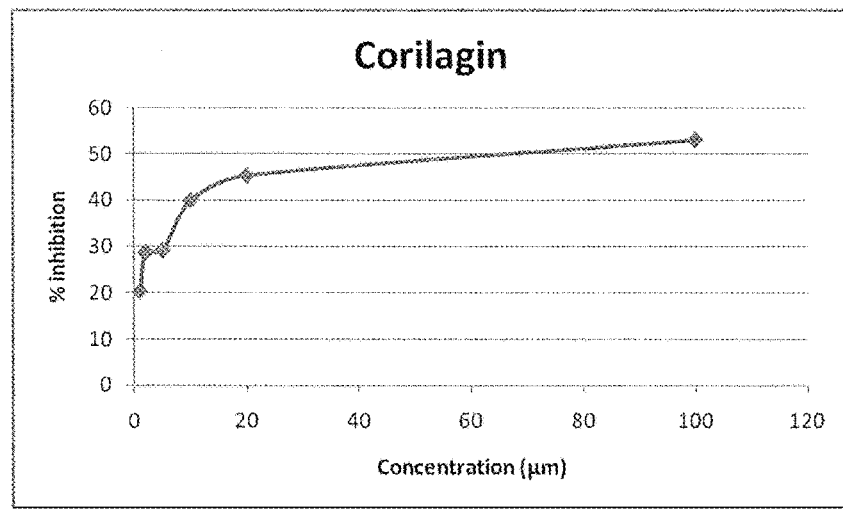
Figure 19:
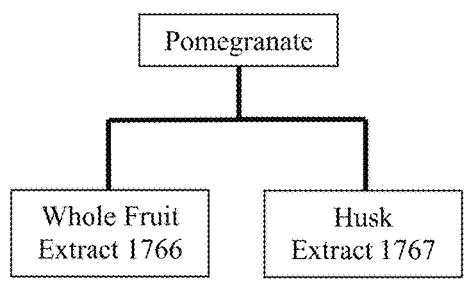
FIG. 19 depicts the results of the PC12 cells assays showing inhibition of the neuronal toxicity induced by Aβ using a fraction from the pomegranate husk shown to contain Punicalagin (dosing at 500 μg/mL).
Figure 19:
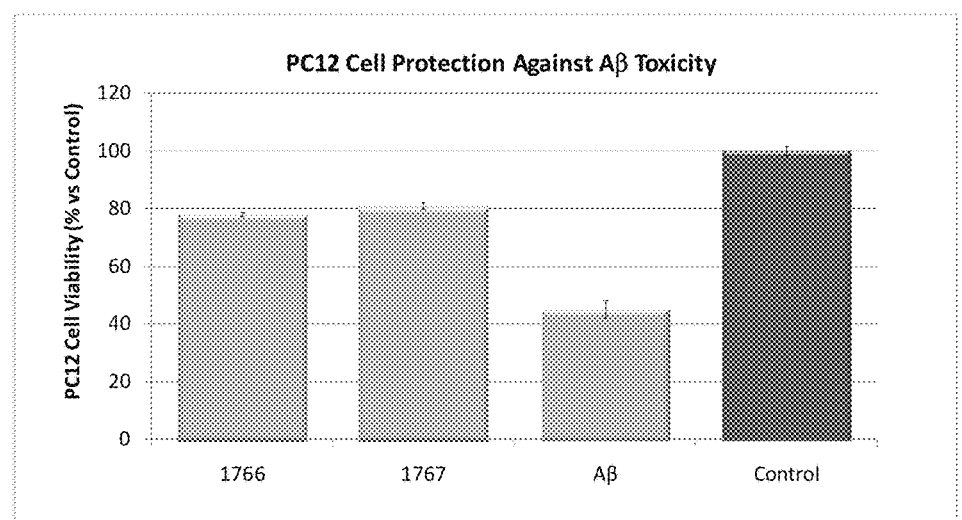
Figure 20:
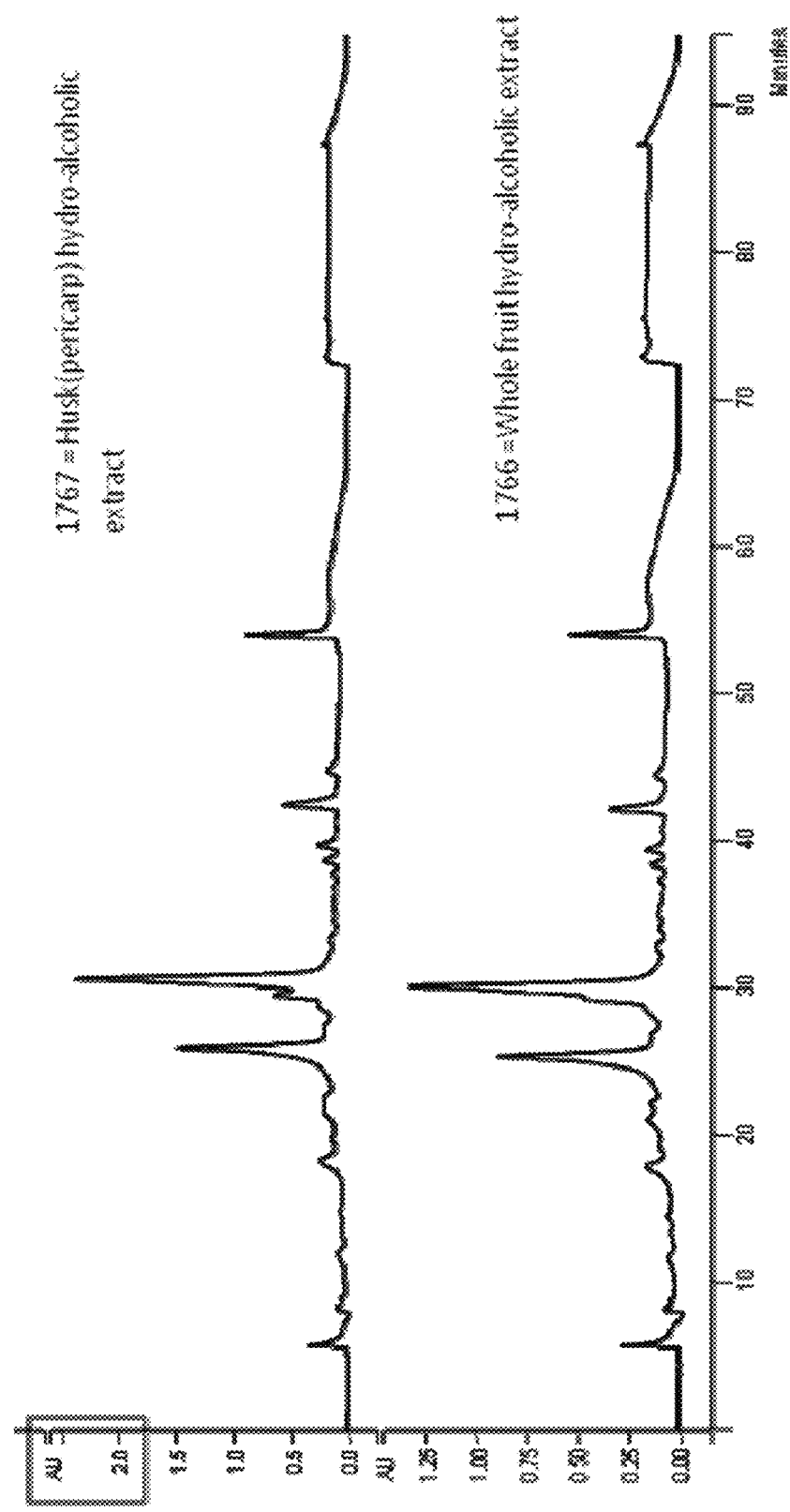
FIG. 20 depicts the HPLC (254 nm) profile of several pomegranate extracts of the invention.
Figure 21:
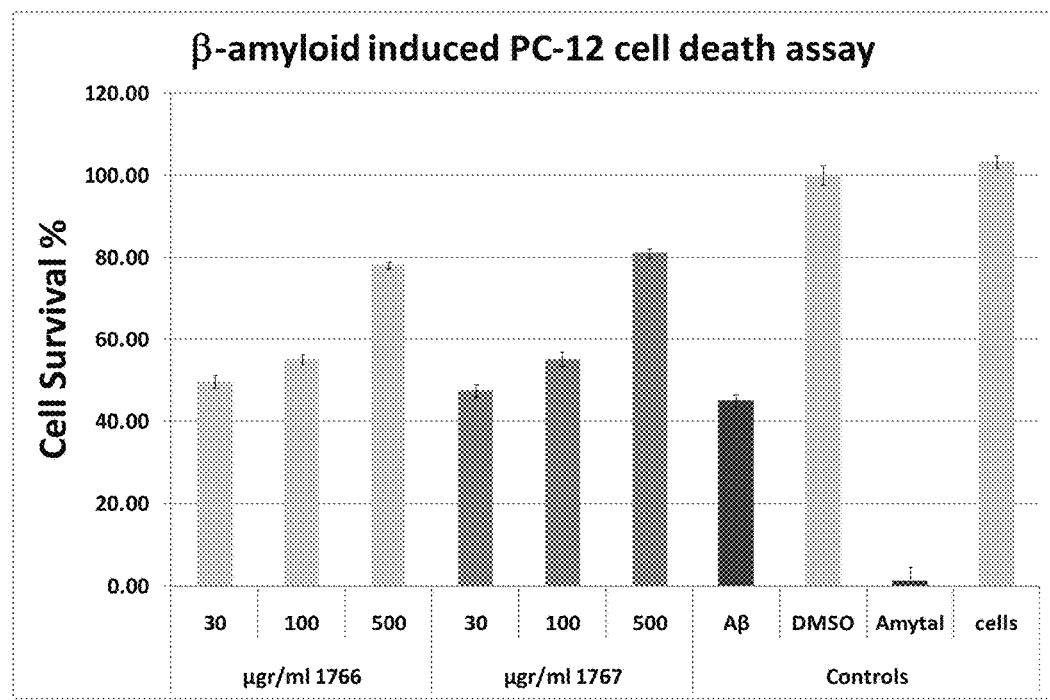
FIG. 21 depicts β-amyloid induced cell death assay in PC12 cells.
Figure 22:
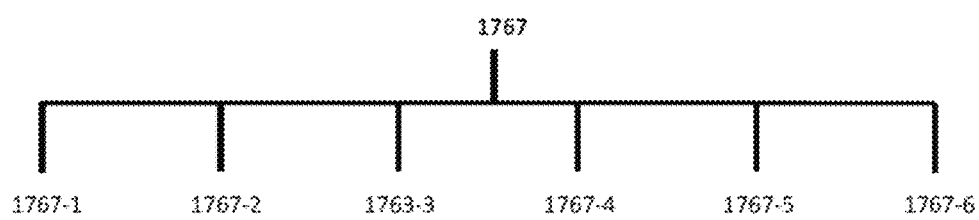
FIG. 22 depicts the HPLC profiles of several subfractions of Extract 1767. These profiles were obtained from a Varian analytic HPLC equipped with a Diode Array detector (DAD) using a 250 mm×4.6 mm Ø-0.5 μm Varian "XRS C18" column. The solvent and gradient used are shown in FIG. 23.
Figure 22:
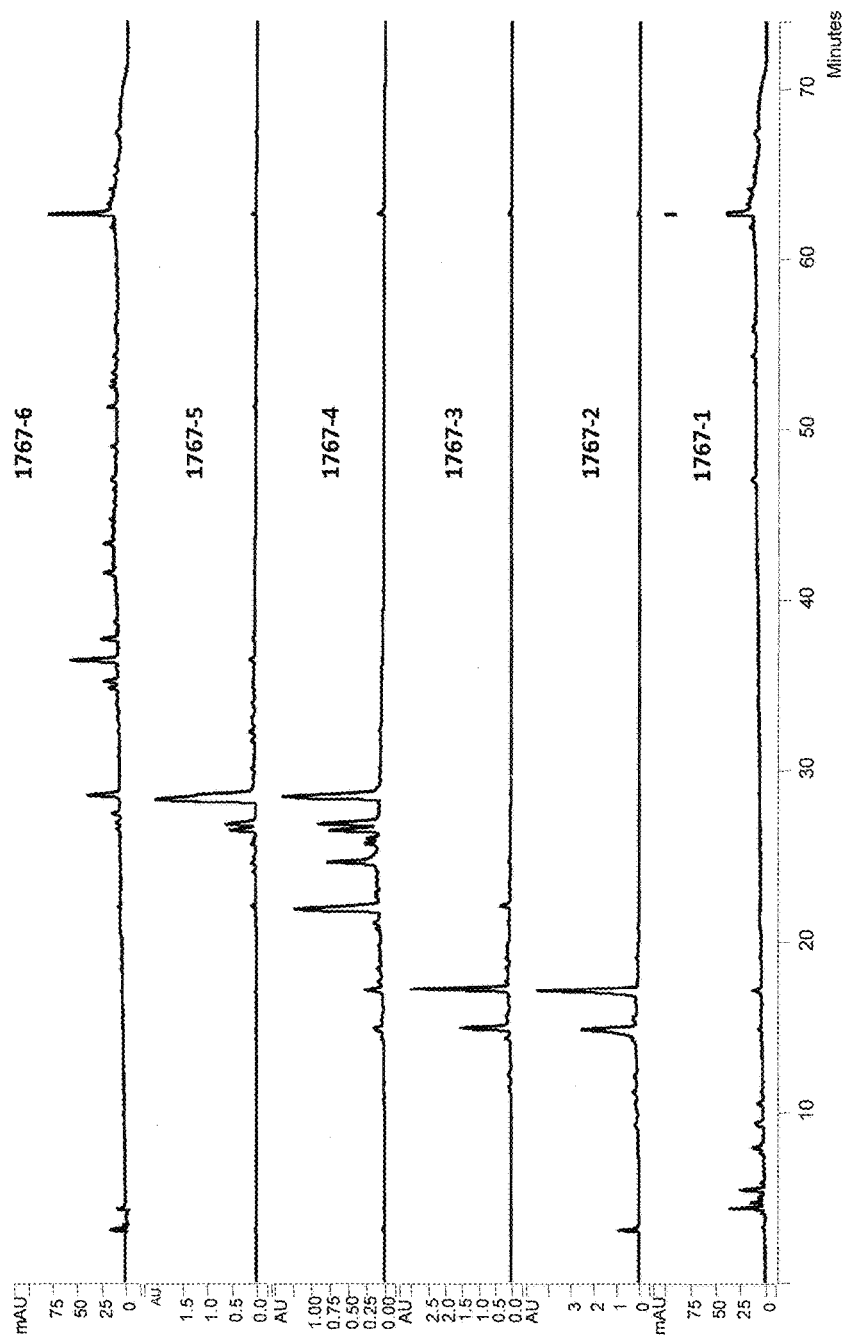
Figure 23:
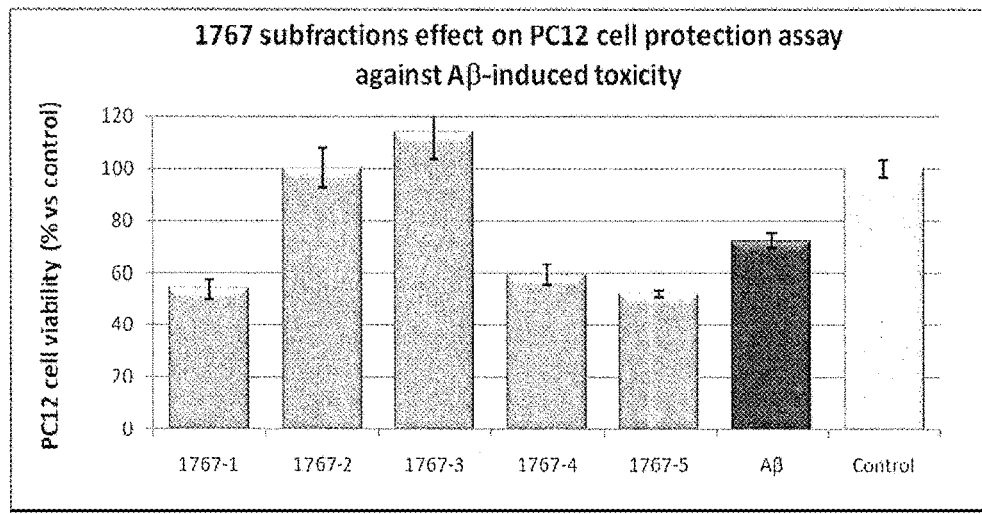
FIG. 23 depicts the solvent and gradient used in to obtain the HLPC traces; and a graph showing the bioactivity of 1767 subfractions on PC12 cell survival against Aβ toxicity.

Pomegranate (*Punica granatum*, Wonderful variety) was extracted using three different buffers to yield fractions enriched with molecules of increased polarity. The pomegranate was blended and extracted with water, butanol, and ethyl-acetate buffers. The three fractions were tested in the assay as described in Example 1 at 10 μg/mL each. The results showed that the ethyl acetate fraction contained the highest activity, being able to inhibit over 65% of the aggregation (FIG. 11).

The ethyl-acetate, butanol and water fraction were further sub-fractionated by centrifugal partition chromatography and pure compounds were isolated using standard HPLC methods. The molecules were identified using HPLC/MS and NMR studies. Each molecule was used at purity above 90% in the assay for aggregation described in Example 1. The results are depicted in FIGS. 12-18 and summarized below.

Fraction A3J inhibited aggregation with an $IC_{50}$ of 10 μM and NMR confirmed the identity of the molecule to be Punicalin; fraction A1D inhibited aggregation with an $IC_{50}$ of 11 μM. MS data confirmed the identity of the molecule to be Pedunculagin; fraction W12 inhibited aggregation with an $IC_{50}$ of 6 μM and was confirmed to be Punicalagin; and fraction A3I inhibited aggregation with an $IC_{50}$ of 9.3 μM. Finally, fraction A3G inhibited aggregation with an $IC_{50}$ of 6.8 μM and NMR and MS data confirmed the identity of the molecule to be Tellimagrandin. Corilagin inhibited aggregation with an $IC_{50}$ of 65 μM.

Example 2

Measuring Inhibition of Aβ-Oligomer Induced Neuronal Cell Death

The fractions that were able to inhibits oligomer formation were also tested for their ability to inhibit Aβ-oligomer induced neuronal cell death using P12 cells, a well known and accepted model of neuronal cell culture.

Beta Amyloid peptide (Aβ) 25-35 trifluoroacetate salt (ref H-1192, lot 2000718) was purchased from Bachem (Bubebdorf, Switzerland). Thiazolyl Blue Tetrazolium Bromide (MTT, ref. M2128) was purchased from Sigma-Aldrich (Saint-Quentin Fallvier, France). Albumin Bovine Fraction V (BSA, ref 160069) was purchased from MPBio (Irvine, USA).

Cells: Rat Pheochromocytoma cells (PC12) were maintained in DMEM (4.5 g/L glucose) supplemented with 10% Horse Serum (HS), 5% Fetal Bovine Serum (FCS) and 100 U/mL penicillin and 100 μg/mL Streptomycin at 37° C. under 5% $CO_2$.

Preparation of Aβ (25-35): It has been reported that Aβ oligomers are more toxic to neurons than monomers. Therefore, the Aβ (25-35) that was used for this study was pre-aggregated prior to use. Aβ was dissolve to 1 mM in water and stored at −20° C. Aβ (25-35) was incubated in 37° C. for 3 days to induce aggregation just prior to use.

Determination of Hydro-Alcoholic Pomegranate Extracts Ability to Protect PC12 Cells Against Aβ Insult: The ability of Pomegranate extracts to protect PC12 cells from Aβ (25-35) oligomer induced toxicity was determined by measuring reduction of MTT to MTT formazan, which reflects cell viability. PC12 cells were plated in 96 wells culture plates and once confluent, were pretreated with different concentrations of Pomegranate extracts (0.1% DMSO) for 1 h in DMEM 0.1% BSA. The cells were then incubated with or without pre-aggregated Aβ (25-35) at 10 μM for an additional 24 h. After the 24 h, MTT solution 300 μg/mL in cell culture medium (stock solution 3 μg/mL in PBS) was added for 2 h at 37° C. The medium was then removed and the formazan crystals are dissolved in 100 μL of DMSO. The level of MTT reduction and thus cell viability was determined by a colorimetric assay measuring the optical density at 595 nm using a microplate reader (BioTek EL808).

As shown in FIG. 24, Extracts 1766 and 1767 were able to protect PC12 neuronal cells from the toxicity of Aβ (25-35) oligomers. Extract 1766 is a hydro-alcoholic extract for the whole pomegranate fruit, Extract 1767 is a hydro-alcoholic extract of the pomegranate husk and For the extraction, whole fruit and husks were separated out and cut, crushed and placed into a blender. The resulting pieces were incubated in a hydro-alcoholic solution (EtOH/water), 80/20) and submitted to agitation at room temperature for 4 hours. After additional maceration in a light protected environment, the solutions were filtered and dried under vacuum (40° C. at 50 mbar) and then stored at −20° C. until use of further fractionation. Subfractions of Extract 1767 were made and tested for their ability to protect against Aβ-inducted cytotoxictiy in PC12 cells. Fractions 1767-2 and 1767-3 were shown to be the most active. Further analysis, concentration and testing of these two fractions led to the indentification of punicalagin as the natural compound responsible for the observed activity. DMSO was used as a carrier and showed no interference on the assay.

Example 4

Extraction Procedure

The pomegranate extract 31008 containing the specific molecules was prepared using an extraction procedure, based on adsorption of polyphenols in a standard polymer adsorption-based column as described. The pomegranates (e.g., Mollar variety) were juiced using a standard juicing and manufacturing process and clarified by centrifugation before being adsorbed into the polymeric chromatographic resin as pure juice. The resin Amberlite XAD-16 (Rohm & Haas) was packed into semi preparative columns and loaded with the extracted juice. The column was washed with water to remove the sugars until completion (Brix levels were below 0.1%). The polyphenols were eluted with 100% ethanol. The remaining ethanol was evaporated under vacuum to produce a concentrated extract containing 4.5 g of total polyphenol per liter as determined using the Folin assay for total polyphenol content.

Extract 31008 was shown to contain the molecules Punicalagins, Punicalin, Tellimagrandin, and Pedunculagin, using HPLC-MS identification for the compounds described above.

This technique is a modification of methods known in the art as described by several published method for purification of polyphenols form various plant and berry. Tuck, K. L. and P. J. Hayball (2002). "Major phenolic compounds in olive oil: metabolism and health effects." *J Nutr Biochem* 13(11): 636-644; and Schieber, A., P. Hilt, et al. (2003). "A new process for the combined recovery of pectin and phenolic compounds from apple pomace." *InnoVations Food Sci. Emerging Technol.* 4: 99-107.

Example 4

Animal Testing—Morris Water Maze

The extract 31008 was tested in an animal model of Alzheimer's disease expressing both the Amyloid mutant London mutations and the prenisilin-1 human mutation. Animals in this model develop plaques by 4 months of age and memory deficits by 6 months. Dense plaque load is visible after 7 months.

In one set of experiments, four-month old APP-PS1 transgenic mice were fed with a fixed dose of approximately 97 mg total polyphenols/kg/days of the extract via their drinking water. After 3 months of feeding, the mice (then 7 months old) were tested in the Morris-Water mazed spatial test.

The Morris Water Maze was performed during days 84-87 of treatment. The pool (a white, circular vessel 1 m in diameter) contained water at 20° C. with titanium-dioxide as an odorless, nontoxic additive to hide the escape platform (1 cm beneath the water level). Swimming of each mouse was videotaped and analyzed (Ethovision, Noldus information Technology, Wageningen, the Netherlands). Prior to training, each mouse was placed on top of the platform for 15 seconds. For place navigation tests, mice were trained to locate the hidden platform in five blocks of three trials over three consecutive days. Each trial consists of a forced swim test of maximum 120 seconds, followed by 60 seconds of rest. The time each mouse needed to locate the platform was measured during the five consecutive blocks of training to determine a learning curve for each mouse.

24 hours after the final training, each animal underwent a probe trial with the platform removed. Mice were allowed to search for the missing platform for 60 seconds and the search time spent in each quadrant of the pool, as well as the number of crossings of the original platform position was measured. As shown in FIG. 24, the mice fed with Extract 31008 showed an increase performance in the probe test as demonstrated by the increased frequency of crossings of the area were the platform was formally located.

Example 5

Animal Testing—Amyloid Plaque Load

As the level of amyloid plaque load has been shown to correlate with the progress of amyloid based diseases, the effects of treatment with the extract 31008 was examined Mice were sacrificed and their brains collected and prepared for immune histochemistry using standard methods. Sagital vibratome sections (40 μm) were cut for free floating incubations and stored at 4° C. until staining in PBS with 0.1% sodium azide. Thirty consecutive sections per brain in the region of the subiculum were selected for staining (laterale between 2.18 and 1.08 mm) Sections 1, 7, 13, 19, 25 were stained with IHC for Aβ (anti-amyloid). Sections of all animals used were randomized for staining and blind quantification.

Free floating sections were incubated in Nett-wells to stain all sections in one single assay and minimize intensity variation. Sections were washed twice in PBS and incubated for 15 minutes in hydrogen peroxide 1.5% in PBS and methanol (1:1) to remove endogenous peroxidase activity. After washing the sections three times in PBS containing 0.1% Triton X100 (PBST), the sections were blocked for 30 minutes in 10% Fetal Calf Serum (FCS) in PBST followed by an overnight incubation with the biotinylated primary antibody in PBST with 10% FCS (anti-amyloid against N-terminal end of Aβ, labeled with biotin, using a dilution of 1:2800). After rinsing, the sections were incubated in 0.01% trypsin in PBS for 15 minutes at 37° C., followed by an incubation with avidin-biotin peroxidase complex (Vectastain Elite ABC, Vector, Burlingame, Calif.). The signal was developed with 3,3'-diaminobenzidine tetrahydrochloride tablets (DAB, ICN, 1 tablet/10 mL Tris-HCl with 3 μL $H_2O_2$ per 10 mL). Sections were counterstained with Mayers hematoxylin, dehydrated in five steps (50, 70, 95 and 2×100%) in ethanol and xylene (Merck Eurolab) and mounted in Depex (Depex mounting medium, BDH Laboratory).

As shown in FIG. 25, the mice fed with the extract has a significant reduction in brain amyloid plaque load consistent with the effect of the identified molecules on aggregation.

In a second set of experiments, two-months-old APP-PS1 transgenic mice were fed with a fixed dose of approximately 90 mg (Extract 31008-L-) and 800 mg (Extract 31008-H-) total polyphenols/kg/days of a highly enriched Punicalagin extract, Extract 31008, via their drinking water. Another group was also fed with a highly enriched Punicalagin extract, Extract 61109 at a dose of 468 mg/kg/d. A final group was fed a pomegranate husk derived extract 71109 at a dose of 120 mg/kg/d. After 4 months of feeding, the mice (then about 6.5 months old) were tested in the Morris-Water Maze spatial memory test.

As shown in FIG. 26, the mice fed with the extract 31008 at a dose of 97 mg/day showed an increase performance during the probe test, as shown by the increase in the time spent in the platform zone. On the other hand, mice fed the extract 31008 at a dose of 828 mg/day showed no change in performance as compared to the control transgenic administered the isocaloric vehicle. This result illustrates a dose effect on the improvement of memory with the employed pomegranate extract. Mice receiving extracts 61109 and 71109 showed a significantly improved performance in the probe test (P<0.05 with Tukey's Multiple Comparison Test versus vehicle hAPP-Tg).

Example 6

Animal Testing—Aged Rats

The effect of oral administration of polyphenols from pomegranate extracts on the cognitive performance of aged rats was studied. This model system was selected to evaluate the effects of the treatment in animals displaying impaired brain function as a result of the ageing process in order to highlight potential benefits that may not be detectable in normal young adults. Treatments were initiated in male Sprague-Dawley rats at the age of 19 months, corresponding approximately to the onset of cognitive impairments (see Martinez-Serrano A, Björklund A. "Ex vivo nerve growth factor gene transfer to the basal forebrain in presymptomatic middle-aged rats prevents the development of cholinergic neuron atrophy and cognitive impairment during aging" Proc Natl Acad Sci USA. 1998 Feb. 17; 95(4):1858-63; and Bisson J F, Nejdi A, Rozan P, Hidalgo S, Lalonde R, Messaoudi M. "Effects of long-term administration of a cocoa polyphenolic extract (Acticoa powder) on cognitive performances in aged rats" Br J Nutr. 2008 July; 100(1):94-101, Epub 2008 Jan. 8). Animal performance was mainly monitored using behavioral tests for swim task learning and social recognition memory.

Polyphenols were administered orally, by dilution in the drinking water, to reproduce the ultimately targeted mode of delivery. Experiments compared two doses of polyphenol-enriched extracts from pomegranate.

a) Social Recognition. In the social recognition discrimination task, each aged rat was placed in its home cage together with a juvenile male Sprague-Dawley rat (<5 weeks old) for 5 minutes. Thirty minutes later, the same exact procedure was repeated with the same juvenile to determine a second time the degree of interaction between the two animals. In animals with a proper functioning memory, less contact is expected as the two animals have had previous interactions. Thirty minutes after the second exposure, a novel juvenile rat was placed for 5 minutes together with the aged rat, in order to measure whether the animal could discriminate between the two different juvenile individuals. During each period of interaction between the two animals, the total time of contact was measured to assess social recognition. This test was performed after 2.5 to 3 months of treatment.

As shown in FIG. 27, in the aged rats fed the low dose of extract 31008 (15 mg gallic acid equivalent/kg/day) the decrease observed in the time spent with juvenile #1 during second exposure indicated improved performance in recognition memory as a result of treatment. When subsequently exposed to the new juvenile rat #2, the interaction time increased in aged rats treated with extract at 15 mg gallic acid equivalent/kg/day, showing that the treated aged rats can distinguish between the two different juvenile rats and have a functioning memory. On the other hand, isocaloric control-treated aged rats have comparable interaction times for the $1^{st}$ and $2^{nd}$ exposure to juvenile rat #1, indicating an impairment in their recognition memory. Control aged rats exposed to juvenile #2 show a comparable interaction time with all prior exposures to juvenile #1, indicating the control animals are unable to distinguish between these interactions, a hallmark of reduced cognition and a decline in memory. (N=12 for isocaloric controls, N=14 for the extract-treated group). Aged rats treated with the extract at a dose of 75 mg gallic acid equivalent/kg/day (N=10), unlike rats treated with th 15 mg GAE, have a performance similar to the isocaloric control group, when exposed a second time to juvenile rat #1 or to a novel juvenile rat #2. Thus demonstrating the importance of dosing in this effect.

b) Morris Water Maze: Reversal Test. Aged rats were treated continuously with the extract 31008 (15 mg gallic acid equivalent/kg/day) or an isocaloric control for a period of 3 months starting at the age of 19 months. Aged rats were tested for their performance in the reversal task: following training and probe test, the platform was placed in the opposite quadrant (WEST→EAST) and the animal was subjected to three training sessions. In this test, the rapidity to re-adapt to a new platform location in a similar task further evaluates learning ability of the animals.

As shown in FIG. 28, aged rats treated with the extract at 15 mg gallic acid equivalent/kg/day were significantly more efficient at localizing the platform in the reversal test, as compared to the isocaloric control aged rats (one-way ANOVA, P<0.02; isocaloric control N=11; extract: N=14). This illustrates the beneficial effects of a low dose of extract (15 mg gallic acid equivalent/kg/day) on memory improvement and protection versus the natural memory decline observed in control, non-treated aged rats. The observed effects of the 15 mg gallic acid equivalent/kg/day dose is consistent with the observations in the social recognition memory evaluation and the importance of proper dosing to achieve memory improvements.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by this disclosure.

We claim:

1. A method for improving memory function, comprising administering to a human in need thereof a therapeutically effective amount of punicalin or punicalagin, or a pharmaceutically acceptable salt of either of them, wherein the therapeutically effective amount is between about 100 mg per day and about 2,500 mg per day, wherein the human does not suffer from cancer.

2. The method of claim 1, wherein the punicalin or punicalagin is administered as part of a nutraceutical composition, pharmaceutical composition, functional food, functional nutrition product, medical food, medical nutrition product, dietary supplement or botanical drug.

3. The method of claim 1, wherein punicalin or a pharmaceutically acceptable salt thereof is administered.

4. The method of claim 1, wherein punicalagin or a pharmaceutically acceptable salt thereof is administered.

5. The method of claim 1, wherein long-term memory is improved.

6. The method of claim 1, wherein short-term memory is improved.

7. The method of claim 3, wherein long-term memory is improved.

8. The method of claim 3, wherein short-term memory is improved.

9. The method of claim 4, wherein long-term memory is improved.

10. The method of claim 4, wherein short-term memory is improved.

11. The method of claim 1, wherein the therapeutically effective amount is between about 250 mg per day and about 1,000 mg per day.

12. The method of claim 11, wherein punicalin or a pharmaceutically acceptable salt thereof is administered.

13. The method of claim 11, wherein punicalagin or a pharmaceutically acceptable salt thereof is administered.

14. The method of claim 11, wherein long-term memory is improved.

15. The method of claim 11, wherein short-term memory is improved.

16. The method of claim 12, wherein long-term memory is improved.

17. The method of claim 12, wherein short-term memory is improved.

18. The method of claim 13, wherein long-term memory is improved.

19. The method of claim 13, wherein short-term memory is improved.

20. A method for decreasing memory loss, comprising administering to a human in need thereof a therapeutically effective amount of punicalin nr punicalagin, or a pharmaceutically acceptable salt of either of them, wherein the therapeutically effective amount is between about 100 mg per day and about 2,500 mg per day, wherein the human does not suffer from cancer.

21. The method of claim 20, wherein the punicalin or punicalagin is administered as part of a nutraceutical composition, pharmaceutical composition, functional food, functional nutrition product, medical food, medical nutrition product, dietary supplement or botanical drug.

22. The method of claim 20, wherein punicalin or a pharmaceutically acceptable salt thereof is administered.

23. The method of claim 20, wherein punicalagin or a pharmaceutically acceptable salt thereof is administered.

24. The method of claim 20, wherein the memory loss is age-related.

25. The method of claim 22, wherein the memory loss is age-related.

26. The method of claim 23, wherein the memory loss is age-related.

27. The method of claim 20, wherein the therapeutically effective amount is between about 250 mg per day and about 1,000 mg per day.

28. The method of claim 27, wherein punicalin or a pharmaceutically acceptable salt thereof is administered.

29. The method of claim 27, wherein punicalagin or a pharmaceutically acceptable salt thereof is administered.

30. The method of claim 27, wherein the memory loss is age-related.

31. The method of claim 28, wherein the memory loss is age-related.

32. The method of claim 29, wherein the memory loss is age-related.

\* \* \* \* \*